(12) United States Patent
Batycky et al.

(10) Patent No.: US 8,415,397 B2
(45) Date of Patent: *Apr. 9, 2013

(54) INHALABLE EPINEPHRINE

(75) Inventors: Richard P. Batycky, Newton, MA (US);
Giovanni Caponetti, Piacenza (IT);
Mariko Childs, Arlington, MA (US);
Elliot Ehrich, Lincoln, MA (US);
Karen Fu, Cambridge, MA (US);
Jeffrey S. Hrkach, Cambridge, MA (US); Wen-I Li, Lexington, MA (US);
Michael M. Lipp, Framingham, MA (US); Mei-Ling Pan, Cambridge, MA (US); Jason Summa, Arlington, MA (US)

(73) Assignee: Civitas Therapeutics, Inc., Chelsea, MA (US)

( * ) Notice: Subject to any disclaimer, the term of this patent is extended or adjusted under 35 U.S.C. 154(b) by 76 days.

This patent is subject to a terminal disclaimer.

(21) Appl. No.: 13/082,626

(22) Filed: Apr. 8, 2011

(65) Prior Publication Data

US 2011/0237681 A1 Sep. 29, 2011

Related U.S. Application Data

(62) Division of application No. 10/607,571, filed on Jun. 26, 2003, now Pat. No. 7,947, 742.

(60) Provisional application No. 60/425,349, filed on Nov. 8, 2002, provisional application No. 60/393,007, filed on Jun. 28, 2002, provisional application No. 60/393,716, filed on Jul. 2, 2002.

(51) Int. Cl.
*A61K 9/14* (2006.01)
*A61K 31/13* (2006.01)
*A61K 31/135* (2006.01)
*A61K 31/045* (2006.01)

(52) U.S. Cl. .......... 514/653; 514/669; 514/728; 424/46; 424/489

(58) Field of Classification Search .................. 514/653, 514/669, 728; 424/46, 489
See application file for complete search history.

(56) References Cited

U.S. PATENT DOCUMENTS

| 6,102,036 A * | 8/2000 | Slutsky et al. ........... 128/203.15 |
| 7,947,742 B2 * | 5/2011 | Batycky et al. ................ 514/653 |
| 2005/0074498 A1 * | 4/2005 | Tarara et al. .................. 424/489 |

FOREIGN PATENT DOCUMENTS

| WO | 9104011 A1 | 4/1991 |
| WO | 03080028 A2 | 10/2003 |

* cited by examiner

*Primary Examiner* — James H. Alstrum-Acevedo
(74) *Attorney, Agent, or Firm* — Elmore Patent Law Group, P.C.; Carolyn S. Elmore, Esq.; Darlene A. Vanstone, Esq.

(57) ABSTRACT

The present invention is directed toward particles for delivery of epinephrine to the respiratory system and methods for treating a patient in need of epinephrine. The particles and respirable compositions comprising the particles of the present invention described herein comprise the bioactive agent epinephrine, or a salt thereof, as a therapeutic agent. The particles are preferably formed by spray drying. Preferably, the particles and the respirable compositions are substantially dry and are substantially free of propellants. In a preferred embodiment, the particles have aerodynamic characteristics that permit targeted delivery of epinephrine to the site(s) of action.

24 Claims, 17 Drawing Sheets

INHALABLE EPINEPHRINE

RELATED APPLICATION(S)

This application is a divisional of U.S. application Ser. No. 10/607,571, filed Jun. 26, 2003, which claims the benefit of U.S. Provisional Application Nos. 60/425,349, filed Nov. 8, 2002; U.S. Provisional Application No. 60/393,007, filed on Jun. 28, 2002, and U.S. Provisional Application No. 60/393,716, filed on Jul. 2, 2002 The entire teachings of the above application(s) are incorporated herein by reference.

BACKGROUND OF THE INVENTION

Anaphylaxis is a serious, acute allergic reaction that often requires emergency room treatment. Pumphrey R. S. H., "Lessons for Management of Anaphylaxis from a Study of Fatal Reactions," *Clin. Exp. Allergy,* 30:1144-50 (2000). It contributes to, or complicates, the course of one out of every 2,700 hospitalized patients (Kemp S. F., et al., "Anaphylaxis. A Review of 266 Cases," *Arch. Intern. Med.,* 155:1749-54 (1995)) and, if not treated properly and promptly, can result in death. Because the number of allergic reactions in the United States and in many European countries is progressively increasing, the incidence of anaphylaxis is also expected to increase. Neugut A. I., et al., "Anaphylaxis in the United States: an Investigation into its Epidemiology," *Arch. Intern. Med.,* 161:15-21 (2001).

Epinephrine, also known as adrenaline, is the drug of choice for the initial treatment of anaphylaxis. See AAAAI Directors, "Position Statement: The Use of Epinephrine in the Treatment of Anaphylaxis," *J. Allergy Clin. Immunol.,* 94(4): 666-68 (1994). Indeed, the FDA has recognized epinephrine "as not only safe and effective, but essential for the treatment of anaphylaxis." NDA 19-430, 1985, Nicklas, Medical Officer Review. Failure to administer epinephrine promptly is considered a most important fact contributing to death of patients with anaphylaxis. Yunginger J. W., et al., "Fatal Food-Induced Anaphylaxis," *J. Am. Med. Assoc.,* 260:1450-52 (1988); Sampson H. A., et al., "Fatal and Near-fatal Anaphylactic Reactions to Food in Children and Adolescents," *New Engl. J. Med.,* 327:380-84 (1992).

Despite the beneficial role of epinephrine in treating anaphylaxis, significant problems with current administration methods greatly compromise treatment. Goldberg, et al., "Insect Sting-Inflicted Systemic Reactions: Attitudes of Patients with Insect Venom Allergy Regarding After-Sting Behavior and Proper Administration of Epinephrine," *J. Allergy Clin. Immunol.,* 106:1184-89 (2000). Numerous studies have emphasized problems with existing treatment options. See e.g., Korenblat P., et al., "A Retrospective Study of Epinephrine Administration for Anaphylaxis: How Many Doses are Needed?" *Allergy Asthma Proc.,* 20:383-86 (1999); Goldberg, et al. Because epinephrine is not orally active, it currently must be given by injection, with substantial variability existing in the plasma concentrations achieved within and between dosing modalities. For example, both the rate of absorption and the peak concentration of epinephrine vary widely with intramuscular (IM) injections with the coefficient of variance (CV) often approaching 50%. Simons F. E. R., et al., "Epinephrine Absorption in Children with a History of Anaphylaxis," *J. Allergy Clin. Immunol.,* 101:33-37 (1998); Gu X., et al., "Epinephrine Absorption after Different Routes of Administration in an Animal Model," *Biopharm. Drug Dispos.,* 20:401-5 (1999); Simons F. E., et al., "Epinephrine Absorption in Adults: Intramuscular versus Subcutaneous Injection," *J. Allergy Clin. Immunol.,* 108:871-73 (2001). With subcutaneous (SC) injections, the time to peak concentration is delayed relative to the IM route, and even greater variability is observed in both the peak concentration achieved and the time to achieve peak concentration. Simons, et al., (1998); Gu, et al. These delays in treatment and lack of predictability significantly compromise patients.

Epinephrine has been used safely with a pulmonary delivery method for years as an over-the-counter (OTC) product for the temporary relief of shortness of breath, tightness of chest and wheezing due to bronchial asthma. PRIMATENE® Mist, Physicians' Desk Reference (2000). A pulmonary form of epinephrine, no longer marketed, was a preferred treatment for anaphylaxis in certain European countries. Medihaler-Epi, Compendium of Data Sheets and Summaries of Product Characteristics, APBI, 693-94 (1998); Muller, et al., "Withdrawal of the MEDIHALER®-epi/ADRENALINE MEDIHALER®," *Allergy,* 53:619-20 (1998).

The EPIPEN® Auto-Injector is an example of a product currently approved in the United States for the self-administration of epinephrine for allergic emergencies. It is intended to provide sufficient arrest of an anaphylactic reaction to allow the patient sufficient time to seek further appropriate medical care. EPIPEN®, Physicians' Desk Reference, 56th ed. Montvale, N.J., Medical Economic Company, Inc., 1236 (2002). Although the EPIPEN® Auto-Injector is recognized as beneficial, it nonetheless has limitations widely acknowledged by the medical community. First, there exists a significant reluctance among patients to self-inject. Thus, they often wait long periods of time prior to administering the EPIPEN® or refrain from treating themselves altogether. Goldberg, et al. These delays greatly compromise their safety, for anaphylactic symptoms generally reach their peak within 30 minutes. Atkinson, et al., "Anaphylaxis," *Med. Clin. North Am.,* 76(4):841-55 (1992); Kemp, et al.; Korenblat, et al. Additionally, for the patients who die, time to death is on the order of 15 minutes following venom and 30 minutes following food exposure. See Pumphrey. Consequently, authorities stress the importance of rapid epinephrine intervention to reduce morbidity and mortality. Secondly, the wide variability in plasma concentrations generally achieved following injection is exacerbated by the patient's poor injection procedures, resulting from self-injection at unexpected and infrequent times, under panic-provoking circumstances. Goldberg, et al. Reliability problems associated with self-administration of epinephrine increase the danger of patients receiving inadequate treatment within the required time frame. R. A. Sabroe, et al., "An Audit of the Use of Self-Administered Adrenaline Syringes in Patients with Angio-Oedema," *British J. of Dermatology,* 146 (4):615-20 (2002). Thirdly, one survey reported that approximately 35% of patients required re-injection with a second EPIPEN®, with 20% of those patients exhibiting even the most mild reaction requiring at least two injections. Korenblat, et al. Thus, depending on the severity of a patient's symptoms, multiple EPIPEN® injections may be necessary.

Therefore, a need exists for more reliable, non-invasive, patient-friendly methods and means for patients to self-administer epinephrine.

SUMMARY OF THE INVENTION

The present invention is directed toward particles for delivery of epinephrine to the respiratory system and methods for treating a patient in need of epinephrine. The particles and respirable compositions comprising the particles of the present invention described herein comprise the bioactive agent epinephrine, or a salt thereof, as a therapeutic agent.

The particles are preferably formed by spray drying. Preferably, the particles and the respirable compositions are substantially dry and are substantially free of propellants. In a preferred embodiment, the particles have aerodynamic characteristics that permit targeted delivery of epinephrine to the site(s) of action.

The present invention is directed, in part, to a method for treating a patient in need of epinephrine, the method comprising administering an effective amount of substantially dry particles to the respiratory system of the patient, wherein the particles comprise (a) epinephrine, or a salt thereof; and (b) at least one pharmaceutically acceptable excipient. In one aspect, the effective amount of particles possess a fine particle fraction of less than 5.6 microns of at least about 45 percent. In another, the effective amount of particles possess a fine particle fraction of less than 3.4 microns of at least about 15 percent.

The invention is also directed, in part, to a method for treating a patient in need of epinephrine, the method comprising administering an effective amount of substantially dry particles to the respiratory system of the patient, the particles comprising epinephrine, or a salt thereof. For example, the invention comprises a method for treating a patient in need of epinephrine, the method comprising administering an effective amount of particles to the respiratory system of the patient, the particles comprising epinephrine, or a salt thereof wherein the effective amount of particles possess a fine particle fraction of less than 5.6 microns of at least about 45 percent. As an additional example, the invention also includes a method for treating a patient in need of epinephrine, the method comprising administering an effective amount of particles to the respiratory system of the patient, the particles comprising epinephrine, or a salt thereof wherein the effective amount of particles possess a fine particle fraction of less than 3.4 microns of at least about 15 percent. In another aspect of the invention, a method for treating a patient in need of rescue therapy for anaphylaxis is provided comprising administering particles to the respiratory system of the patient, the particles comprising a therapeutically effective amount of epinephrine, or a salt thereof; wherein the particles are delivered to the respiratory system and the epinephrine reaches its site of action within a time sufficiently short to provide said rescue therapy.

The claimed invention also includes a method for treating a patient in need of epinephrine, the method comprising administering an effective amount of substantially dry particles to the respiratory system of the patient, wherein the particles comprise epinephrine, or a salt thereof, and wherein a first portion of the particles is deposited in the airways of the respiratory system and a second portion of the particles is deposited to the alveoli region of the lungs.

Additionally, a method for treating a patient in need of rescue therapy for anaphylaxis is contemplated. The method comprises administering particles to the respiratory system of the patient, wherein the particles comprise (a) a therapeutically effective amount of epinephrine, or a salt thereof; and (b) at least one pharmaceutically acceptable excipient, wherein the particles are delivered to the respiratory system and the epinephrine reaches its site of action within a time sufficiently short to provide said rescue therapy. Furthermore, the instant invention comprises a method for treating a patient suffering from anaphylaxis, wherein the method comprises: (a) administering an effective amount of substantially dry particles to the respiratory system of the patient, the particles comprising epinephrine, or a salt thereof; (b) monitoring the patient; and (c) administering additional epinephrine to the patient.

The present invention also comprises a method for treating a patient in need of epinephrine, the method comprising: (a) administering an effective amount of a first mass of substantially dry particles to the respiratory system of the patient, the particles comprising epinephrine, or a salt thereof; and (b) subsequently, administering an effective amount of a second mass of substantially dry particles to the respiratory system of the patient, the particles comprising epinephrine, or a salt thereof. Further, the invention comprises a method for treating a patient suffering from anaphylaxis, comprising: (a) administering an effective amount of a first mass of substantially dry particles to the respiratory system of the patient, the particles comprising epinephrine, or a salt thereof; and (b) subsequently, administering an effective amount of a second mass of substantially dry particles to the respiratory system of the patient, the particles comprising epinephrine, or a salt thereof; wherein the first and second masses of substantially dry particles comprise about 11 to about 21 weight percent epinephrine bitartrate; about 62 to about 82 weight percent leucine; and about 7 to about 17 weight percent sodium tartrate.

In addition to the above mentioned methods for treating a patient, the instant invention is directed to particles for the delivery of epinephrine to the respiratory system, and methods for treating a patient in need of epinephrine comprising administering an effective amount of said particles to the respiratory system of a patient. The particles in various embodiments comprise: (i) epinephrine, or a salt thereof; a carboxylic acid, or a salt thereof; a salt comprising at least one multivalent cation or anion; and a phospholipid; (ii) epinephrine, or a salt thereof; an amino acid; and a sugar; (iii) epinephrine, or a salt thereof; and an amino acid; (iv) epinephrine, or a salt thereof; an amino acid; and a carboxylic acid, or a salt thereof; (v) about 11 to about 21 weight percent epinephrine bitartrate; about 62 to about 82 weight percent leucine; and about 7 to about 17 weight percent sodium tartrate; or (vi) about 12 to about 23 weight percent epinephrine bitartrate; and about 77 to about 88 weight percent leucine.

In one embodiment, the present invention is directed to spray dried particles for delivery of epinephrine to the respiratory system wherein the particles comprise (a) epinephrine, or a salt thereof; and (b) at least one pharmaceutically acceptable excipient and wherein the particles possess a fine particle fraction of less than 5.6 microns of at least about 45 percent. In another embodiment, the spray dried particles possess a fine particle fraction of less than 3.4 microns of at least about 15 percent.

In one aspect, the particles for delivery of epinephrine to the respiratory system are essentially dry and comprise: (a) epinephrine, or a salt thereof; and (b) at least one pharmaceutically acceptable excipient.

The instant invention also includes a propellent-free pharmaceutical composition comprising essentially dry particles for delivery of epinephrine to the respiratory system, wherein the particles comprise: (a) epinephrine, or a salt thereof; and (b) at least one pharmaceutically acceptable excipient. Advantageously, the scope of the instant invention additionally includes a substantially antioxidant-free pharmaceutical composition comprising dry particles for delivery of epinephrine to the respiratory system, wherein the particles comprise: (a) epinephrine, or a salt thereof; and (b) at least one pharmaceutically acceptable excipient.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1A, X-Ray Powder Diffraction (XRPD) data for bulk epinephrine bitartrate. Scans at (top to bottom) 200, 155, 145, and 25° C. (5° C./min heating rate). FIG. 1B, XRPD data for bulk leucine at 25° C. FIG. 1C, XRPD data for spray dried leucine/epinephrine bitartrate/sodium tartrate particles. Scans at (top to bottom) 200, 147, 140, 80, 52, and 25° C. (5° C./min heating rate).

FIG. 3A, Chromatogram of an epinephrine sample spiked with norepinephrine and 3,4-dihydroxybenzylamine (internal standard "IS"). FIG. 3B, Chromatogram of a single sample with high epinephrine concentration showing no additional peaks of impurities (entire epinephrine peak). FIG. 3C, Chromatogram of a single sample with high epinephrine concentration showing no additional peaks of impurities (epinephrine peak closeup).

FIG. 4A, Epinephrine standard chromatogram from the pharmacokinetic study showing the epinephrine peak and the internal standard peak. FIG. 4B, Chromatogram showing epinephrine levels in rat plasma at various times after insufflation with dry powder epinephrine powder.

DETAILED DESCRIPTION OF THE INVENTION

Figure 1A:
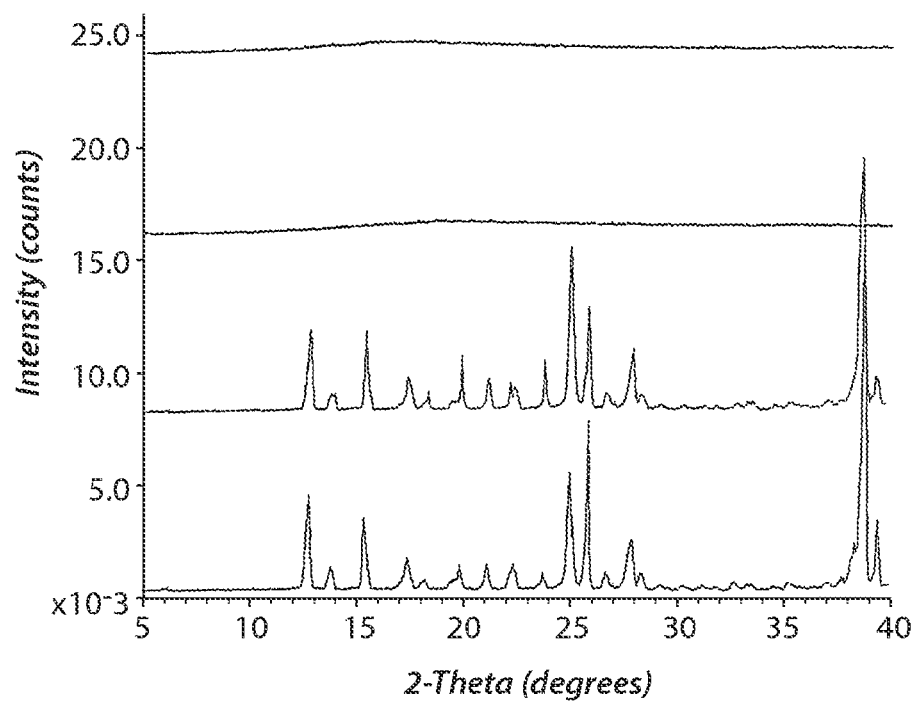
FIGS. 1A, 1B, and 1C.
Figure 1B:
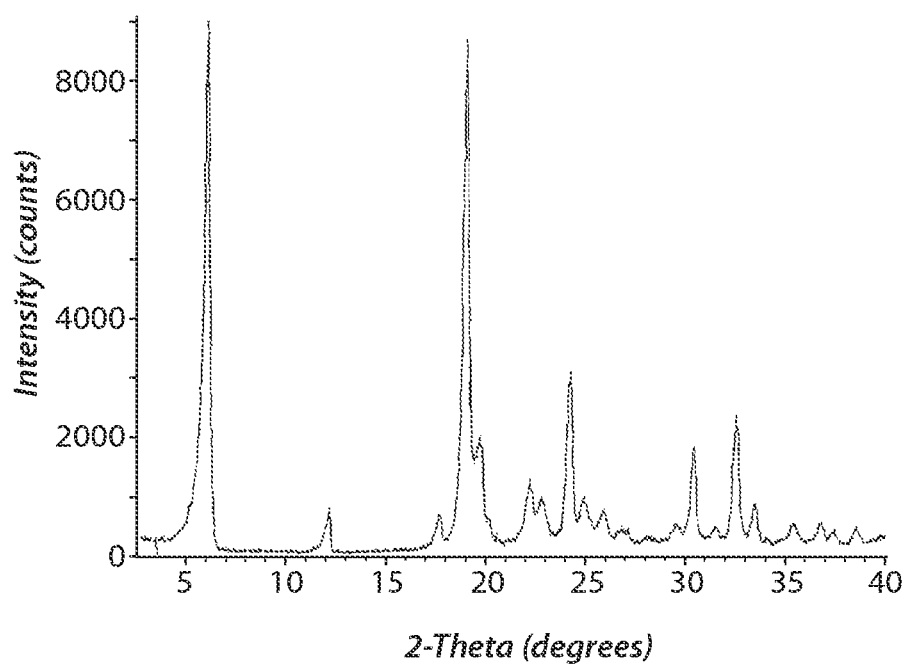
Figure 1C:
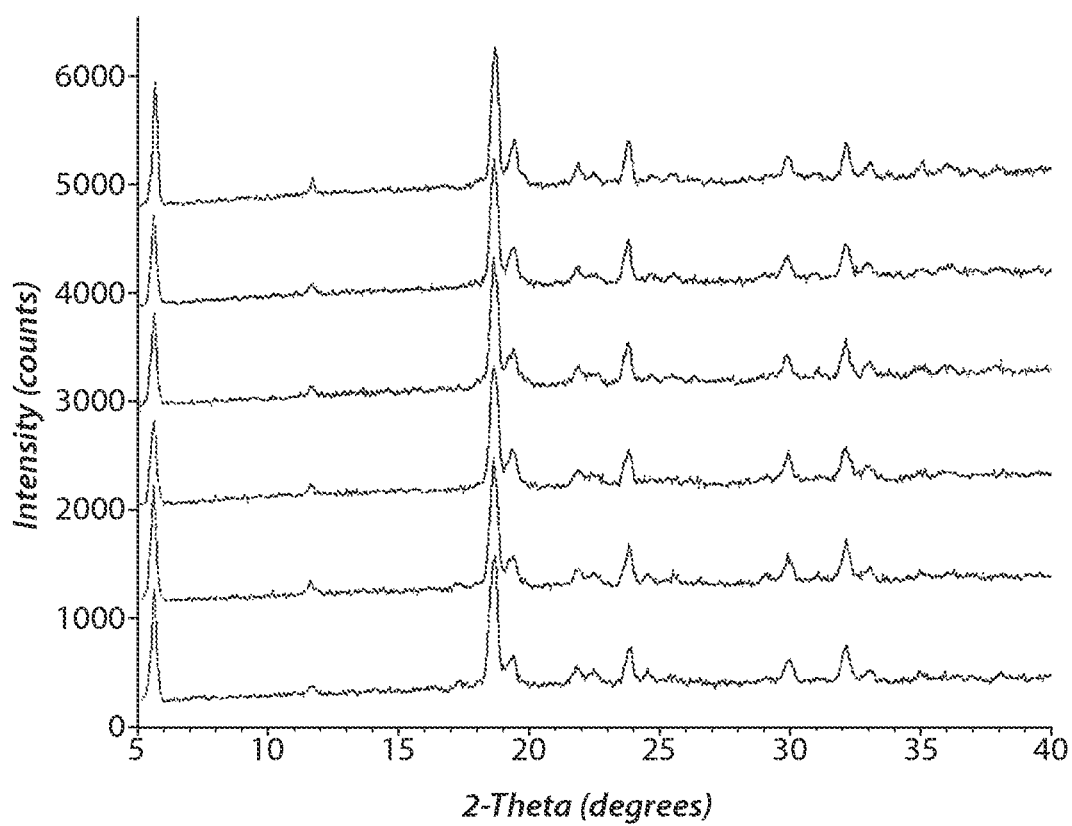

A description of preferred embodiments of the invention follows.

The present invention is directed toward particles for delivery of epinephrine to the respiratory system and methods for treating a patient in need of epinephrine. The particles and respirable compositions comprising the particles of the present invention described herein comprise the bioactive agent epinephrine, or a salt thereof, as a therapeutic agent. The particles are preferably formed by spray drying. Preferably, the particles and the respirable compositions are substantially dry and are substantially free of propellents. In one preferred embodiment, the particles have aerodynamic characteristics that permit targeted delivery of epinephrine to the site(s) of action.

The particles and respirable compositions comprising the particles of the invention, both hereinafter referred to as "particles" or "powders," are also preferably biocompatible, and optionally are capable of affecting the rate of delivery of epinephrine. In addition to epinephrine, the particles can further include a variety of pharmaceutically acceptable excipients. Both inorganic and organic materials can be used. Suitable materials can include, but are not limited to, lipids, phospholipids, fatty acids, inorganic salts, carboxylic acids, amino acids, carbohydrates, tartrate, and various sugars. Preferred particle compositions are further described below.

Practice of the instant invention provides numerous advantages over conventional epinephrine delivery systems. The respirable particles of the invention and the methods of their administration avoid the uncomfortable and often painful injections required by some conventional forms of epinephrine. The availability of a reliable inhaled form of epinephrine is expected to increase patient compliance and to reduce delays in treatment by, for example, providing a needle-free epinephrine delivery system. Epinephrine containing dry powder particles will allow patients to carry a convenient, compact inhaler and reliably self-administer epinephrine non-invasively.

The blood plasma concentrations of epinephrine achieved via dry powder particles of the instant invention have shown to be significantly less variable than current injections, offering another important improvement over existing therapies. Decreased variability, i.e., greater reliability, in peak and time to peak systemic epinephrine concentrations ($C_{MAX}$ and $T_{MAX}$, respectively) through administration of the dry powders of the present invention may result in greater consistency in therapeutic response and an improved safety profile over currently available epinephrine formulations. Moreover, epinephrine delivered via the lungs formulated as dry powder particles has demonstrated relatively rapid absorption and time to peak blood plasma concentrations, which should further improve the therapeutic benefits of epinephrine, for example, the ability of epinephrine to arrest a rapidly progressing anaphylactic reaction. The unique characteristics of aerodynamically light particles comprising epinephrine, or a salt thereof, provide for improved physiological effects such as, for example, increased therapeutic effect(s) or increased duration of therapeutic effect(s).

The epinephrine containing particles can be formulated to modify or control the release of epinephrine and/or the elimination of epinephrine from the patient. For example, the particles of the present invention can have quick elimination of epinephrine from the blood stream relative to conventional epinephrine therapies such as auto-injected epinephrine. A consistent pharmacokinetic profile demonstrating a relatively quick elimination of epinephrine from the blood stream can allow for more precise and predictable treatment of patients in need of epinephrine. Alternatively, particles may be formulated, as described herein, for sustained release and/or action of epinephrine. Particles may be formulated having both a quick onset of action by epinephrine as well as having a sustained release and/or action.

The disclosed respirable particles and methods of their administration allow for the delivery of epinephrine both locally and systemically. Administration of particles comprising epinephrine provides on-demand treatment without the inconvenience of injections. Selective delivery of epinephrine to the site(s) of action can be obtained in a time frame not available with intramuscular, subcutaneous, or auto-injected formulations. By practicing the invention, relief is available to symptomatic patients in a time frame during which the epinephrine of conventional therapies (i.e., intramuscular, subcutaneous, or auto-injected formulations) would still be traveling to the site of action. The particles of the invention are preferably aerodynamically light, as described herein, and are capable of depositing in the airways or in the alveoli, or deep lung, for delivery of epinephrine to the blood stream and subsequent systemic action. The particles of the invention are also capable of depositing locally at sites of obstruction or congestion in the respiratory system for topical delivery of epinephrine. For example, by depositing epinephrine containing particles directly into the airway passages and the lungs, respiratory complications of anaphylactic response (e.g., bronchospasm and laryngeal edema) should be more quickly and more effectively treated. By contrast, parenteral (e.g., intravenous, intramuscular, subcutaneous, and auto-injected) epinephrine administration does not achieve this local delivery component.

Advantageously, the particles of the invention are capable of delivering an effective amount of epinephrine to a patient in a single breath activated step. The dose of epinephrine delivered in a single inhalation can range from about 50 micrograms to several milligrams.

The particles of the present invention comprise epinephrine also referred to herein as the "bioactive agent," "therapeutic agent," "agent," "medicament," or "drug." Epinephrine, a catecholamine, is known chemically as 4-[1-hydroxy-2-(methylamino)ethyl]-1,2-benzenediol and is represented by Structural Formula I:

$$HO-C_6H_3(OH)-CH(OH)-CH_2-NH-CH_3 \quad (I)$$

Epinephrine used in the present invention can be obtained from natural sources, such as, for example, from the adrenal glands of animals, or can be synthetically produced, such as, for example, from pyrocatechol. Particles of the invention can comprise salts of epinephrine, including, but not limited to, epinephrine hydrochloride ($C_9H_{13}NO_3 \cdot HCl$) or epinephrine bitartrate ($C_9H_{13}NO_3 \cdot C_4H_6O_6$). Alternatively, the particles may comprise epinephrine free base ($C_9H_{13}NO_3$), i.e., epinephrine lacking salt or a counterion. The particles of the invention may also comprise a mixture of two or more forms of epinephrine. The particles may also comprise one or more derivatives or analogs of epinephrine. The derivatives or analogs may be obtained from natural sources or from synthetic routes. Examples of derivatives or analogs of epinephrine include, but are not limited to, phenyl epinephrine and norepinephrine.

Epinephrine is a chiral molecule. Particles may comprise the (L)- or (D)-stereoisomers of epinephrine, or a mixture thereof (e.g., an optically active mixture or a racemic mixture). Preferably, the particles contain epinephrine that substantially comprises the (L)-isomer, for example, at least about 70, 80, 90, or 95% of the epinephrine is the (L)-isomer.

The amount of epinephrine, or salt thereof, present in the particles can range from about 1 to about 95 percent by weight. Alternatively, a mixture of epinephrine forms is present in the particles at a concentration of about 1 to about 95 weight percent. The particles of the instant invention can comprise about 1 to about 60, about 1 to 55, about 1 to 50, about 1 to 45, about 1 to 40, or preferably, about 1 to about 30 weight percent epinephrine, or salt(s) thereof. The particles can comprise about 1 to about 20 weight percent epinephrine such as about 1 to about 10 weight percent epinephrine; about 1 to about 15 weight percent epinephrine free base, for example, about 1 to about 10 or about 5 weight percent epinephrine free base; about 1 to about 25 weight percent epinephrine bitartrate such as about 5 to about 20 or about 9 to about 18 weight percent epinephrine bitartrate; and/or about 1 to about 20 weight percent epinephrine hydrochloride such as about 5 to about 15, about 10 to about 15, or about 12 weight percent epinephrine hydrochloride.

In one aspect, the particles of the instant invention comprise epinephrine, or a salt thereof, and at least one pharmaceutically acceptable excipient. Examples of pharmaceutically acceptable excipients are described below. The particles of the invention are essentially, or substantially, free of liquid, that is, the particles are substantially dry. The term "substantially dry," as it is used herein, refers to containing no more than about 10% liquid by weight. Preferably, the particles contain no more than about 10% liquid by weight, for example, the particles can contain about 1 to about 8% liquid, about 2 to about 6% liquid, or about 2 to about 5% liquid (percentages by weight).

The term "substantially propellant-free," as used herein, refers to containing less than 1 percent by weight propellent(s). The particles described herein are preferably completely free of propellents (i.e., are propellent-free).

In one aspect, the particles and respirable compositions comprising the particles of the invention comprise a phospholipid or a combination of phospholipids. Examples of suitable phospholipids include, among others, those listed in U.S. Patent Application No. 60/150,742, entitled "Modulation of Release From Dry Powder Formulations by Controlling Matrix Transition," filed on Aug. 25, 1999, the contents of which are incorporated herein in their entirety. Other suitable phospholipids include phosphatidylcholines, phosphatidylethanolamines, phosphatidylglycerols, phosphatidylserines, phosphatidylinositols and combinations thereof. Specific examples of phospholipids include but are not limited to 1,2-dipalmitoyl-sn-glycero-3-phosphocholine (DPPC), 1,2-distearoyl-sn-glycero-3-phosphocholine (DSPC), 1-myristoyl,-2-stearoyl-sn-glycero-3-phosphocholine (MSPC), 1,2-dimyristoyl-sn-glycero-3-phosphoethanolamine (DMPE),1,2-distearoyl-sn-glycero-3-[phospho-rac-(1-glycerol)] (DSPG), 1,2-dipalmitoyl-sn-glycero-3-phosphoethanolamine (DPPE), or any combination thereof. Other phospholipids are known to those skilled in the art. In a preferred embodiment, the phospholipids are endogenous to the lung.

In one preferred embodiment, the particles of the instant invention comprise the phospholipid 1,2-dipalmitoyl-sn-glycero-3-phosphocholine (DPPC). DPPC may be present in the particles in a concentration of at least about 50 percent by weight, preferably at least about 55 percent by weight, or more preferably about 55 to about 70 percent by weight, for example, about 58 to about 65 percent by weight.

The phospholipids or combinations thereof can be selected to impart controlled release properties to the highly dispersible particles. The phase transition temperature of a specific phospholipid can be below, around, or above the physiological temperature of a patient. By selecting phospholipids or combinations of phospholipids according to their phase transition temperature, the particles can be tailored to have controlled epinephrine release properties. For example, by administering particles which include a phospholipid or combination of phospholipids which have a phase transition temperature higher than the patient's body temperature, the release of an agent, such as epinephrine, can be slowed down. On the other hand, rapid release can be obtained by including in the particles phospholipids having lower transition temperatures.

Particles having controlled release properties and methods of modulating release of a biologically active agent are described in U.S. Patent Application No. 60/150,742 entitled "Modulation of Release From Dry Powder Formulations by Controlling Matrix Transition," filed on Aug. 25, 1999, and in U.S. patent application Ser. No. 09/792,869 entitled "Modulation of Release From Dry Powder Formulations," filed on Feb. 23, 2001. The contents of these applications are incorporated by reference in their entirety.

The particles of the present invention can comprise a charged phospholipid. The term "charged phospholipid," as used herein, refers to phospholipids which are capable of possessing an overall net charge. The charge on the phospholipid can be negative or positive. The phospholipid can be chosen to have a charge opposite to that of epinephrine when the phospholipid and epinephrine are associated. Preferably, the phospholipid is endogenous to the lung or can be metabolized upon administration to a lung endogenous phospholipid. Combinations of charged phospholipids can be used. A combination of charged phospholipids can also have an overall net charge opposite to that of epinephrine.

In one embodiment, the association of epinephrine and an oppositely charged lipid can result from ionic complexation. In another embodiment, association of a therapeutic agent and an oppositely charged lipid can result from hydrogen bonding. In yet a further embodiment, the association of a therapeutic agent and an oppositely charged lipid can result from a combination of ionic complexation and hydrogen bonding.

The charged phospholipid can be a negatively charged lipid such as, a 1,2-diacyl-sn-glycero-3-[phospho-rac-(1-glycerol)].

The 1,2-diacyl-sn-glycero-3-[phospho-rac-(1-glycerol)] phospholipids can be represented by Structural Formula II:

(II)

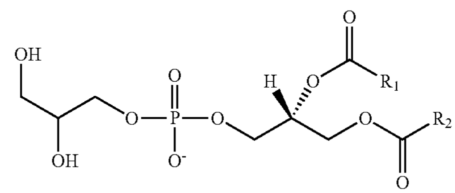

wherein $R_1$ and $R_2$ are each independently an aliphatic group having from about 3 to about 24 carbon atoms, preferably from about 10 to about 20 carbon atoms.

"Aliphatic group" as that term is used herein in reference to Structural Formulas II-V refers to substituted or unsubstituted straight chained, branched or cyclic $C_1$-$C_{24}$ hydrocarbons which can be completely saturated, which can contain one or more heteroatoms such as nitrogen, oxygen or sulfur and/or which can contain one or more units of unsaturation.

Suitable substituents on an aliphatic group include —OH, halogen (e.g., —Br, —Cl, —I and —F), —O(aliphatic, substituted), —CN, —$NO_2$, —COOH, —$NH_2$, —NH(aliphatic group, substituted aliphatic), —N(aliphatic group, substituted aliphatic group)$_2$, —COO(aliphatic group, substituted aliphatic group), —$CONH_2$, —CONH(aliphatic, substituted aliphatic group), —SH, —S(aliphatic, substituted aliphatic group) and —NH—C(═NH)—$NH_2$. A substituted aliphatic group can also have a benzyl, substituted benzyl, aryl (e.g., phenyl, naphthyl or pyridyl) or substituted aryl group as a substituent. A substituted aliphatic group can have one or more substituents.

Specific examples of this type of negatively charged phospholipid include, but are not limited to, 1,2-distearoyl-sn-glycero-3-[phospho-rac-(1-glycerol)] (DSPG); 1,2-dimyristoyl-sn-glycero-3-[phospho-rac-(1-glycerol)] (DMPG); 1,2-dipalmitoyl-sn-glycero-3-[phospho-rac-(1-glycerol)] (DPPG); 1,2-dilauroyl-sn-glycero-3-[phospho-rac-(1-glycerol)] (DLPG); and 1,2-dioleoyl-sn-glycero-3-[phospho-rac-(1-glycerol)] (DOPG).

The particles of the invention can also comprise phospholipids which are zwitterionic and therefore do not possess an overall net charge. Such lipids, can assist in providing particles with the proper characteristics for inhalation. Such phospholipids suitable for use in the invention include, but are not limited to, 1,2-diacyl-sn-glycero-3-phosphocholine, 1,2-diacyl-sn-glycero-3-phosphoethanolamine, and 1,2-diacyl-sn-glycero-3-phospho-[2-trialkylammonioethanol] phospholipids.

The 1,2-diacyl-sn-glycero-3-phosphocholine phospholipids can be represented by Structural Formula III:

$$\text{(III)}$$

$R_1$ and $R_2$ are each independently an aliphatic group having from about 3 to about 24 carbon atoms, preferably from about 10 to about 20 carbon atoms.

Specific examples of 1,2-diacyl-sn-glycero-3-phosphocholine phospholipids include, but are not limited to, 1,2-dipalmitoyl-sn-glycero-3-phosphocholine (DPPC); 1,2-distearoyl-sn-glycero-3-phosphocholine (DSPC); 1,2-dilaureoyl-sn-3-glycero-phosphocholine (DLPC); 1,2-dimyristoyl-sn-glycero-3-phosphocholine (DMPC); and 1,2-dioleoyl-sn-glycero-3-phosphocholine (DOPC).

The 1,2-diacyl-sn-glycero-3-phosphoethanolamine and 1,2-diacyl-sn-glycero-3-phospho-[2-trialkylammonioethanol] phospholipids can be represented by Structural Formula IV:

$$\text{(IV)}$$

wherein $R_1$ and $R_2$ are each independently an aliphatic group having from about 3 to about 24 carbon atoms, preferably, from about 10 to about 20 carbon atoms and $R_4$ is independently hydrogen or an aliphatic group having from about 1 to about 6 carbon atoms.

Specific examples of this type of phospholipid include, but are not limited to, 1,2-dipalmitoyl-sn-glycero-3-phosphoethanolamine (DPPE); 1,2-dimyristoyl-sn-glycero-3-phosphoethanolamine (DMPE); 1,2-distearoyl-sn-glycero-3-phosphoethanolamine (DSPE); 1,2-dilauroyl-sn-glycero-3-phosphoethanolamine (DLPE); and 1,2-dioleoyl-sn-glycero-3-phosphoethanolamine (DOPE).

The particles of the present invention can comprise an asymmetric phospholipid. "Asymmetric phospholipids" are also known to those experienced in the art as "mixed-chain" or "non-identical chain" phospholipids. Asymmetric phospholipids having headgroups such as phosphatidylcholine, phosphatidylethanolamine, phosphatidylglycerol, and phosphatidic acids may be used. Examples of asymmetric phospholipid include the 1-acyl, 2-acyl-sn-glycero-3-phosphocholines.

The 1-acyl,2-acyl-sn-glycero-3-phosphocholine phospholipids can be represented by Structural Formula V:

$$\text{(V)}$$

wherein $R_1$ and $R_2$ are each independently an aliphatic group having from about 3 to about 24 carbon atoms and wherein the aliphatic groups represented by $R_1$ and $R_2$ have differing carbon chain lengths. Preferably, $R_1$ and $R_2$ have from about 10 to about 20 carbon atoms.

Specific examples of this type of phospholipid include, but are not limited to, 1-palmitoyl-2-stearoyl-sn-glycero-3-phosphocholine (PSPC); 1-stearoyl-2-palmitoyl-sn-glycero-3-phosphocholine (SPPC); 1-stearoyl-2-myristoyl-sn-glycero-3-phosphocholine (SMPC); 1-myristoyl-2-stearoyl-sn-glycero-3-phosphocholine (MSPC); 1-myristoyl-2-palmitoyl-sn-glycero-3-phosphocholine (MPPC); and 1-palmitoyl-2-myristoyl-sn-glycero-3-phosphocholine (PMPC).

Particles of the present invention may comprise combinations of asymmetric phospholipids, combinations of symmetric phospholipids, or combinations of asymmetric and symmetric (i.e., identical chain) phospholipids.

In one embodiment of the present invention, particles comprise asymmetric phospholipids having individual acyl chains that are naturally present in the lung. Particles comprising disaturated phospholipids are preferred over particles comprising mono- or di-unsaturated phospholipids.

Without being held to any particular theory, Applicants believe that particles containing asymmetric phospholipids may possess unique packing and/or partition of constituent epinephrine molecules and result in entrapment or encapsulation of the drug. It is thought that drug release and subsequent uptake of the drug payload from the aerosol formulation will be slower if the drug is entrapped or encapsulated rather than simply surface-associated. Applicants believe that for entrapped or encapsulated epinephrine molecules, the availability of the agent in the dissolution media or physiological lining fluids is not only determined by drug solubility but also by particle dissolution and/or diffusion of drug molecules from the particle matrix. In contrast, it is believed that in particles in which drug molecules are primarily surface associated, the availability of drug molecules is primarily drug solubility limited. Consequently, entrapment or encapsulation of the drug in the particle matrix may slow release and subsequent uptake of the drug.

Particles comprising asymmetric phospholipids are described in U.S. Patent Application No. 60/359,466, entitled "Sustained Release Formulations Utilizing Asymmetric Phospholipids," filed on Feb. 22, 2002, the contents of which are incorporated herein in their entirety.

In one embodiment of the invention, particles comprise one or more amino acids. Hydrophobic amino acids are preferred. In a preferred embodiment, the particles comprise the amino acid leucine. In another preferred embodiment, the particles comprise an analog of leucine. Other suitable amino acids include naturally occurring and non-naturally occurring hydrophobic amino acids. Non-naturally occurring amino acids include, for example, beta-amino acids. Both D, L and racemic configurations of hydrophobic amino acids can be employed. Suitable hydrophobic amino acids can also include amino acid analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic $C_1$-$C_8$ hydrocarbons which are completely saturated, which contain one or two heteroatoms such as nitrogen, oxygen or sulfur and/or which contain one or more units of desaturation. Aromatic groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include —OH, halogen (e.g., —Br, —Cl, —I and —F), —O(aliphatic, substituted aliphatic, benzyl, substituted benzyl, aryl or substituted aryl group), —CN, —NO$_2$, —COOH, —NH$_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO(aliphatic group, substituted aliphatic, benzyl, substituted benzyl, aryl or substituted aryl group), —CONH$_2$, —CONH(aliphatic, substituted aliphatic group, benzyl, substituted benzyl, aryl or substituted aryl group), —SH, —S(aliphatic, substituted aliphatic, benzyl, substituted benzyl, aromatic or substituted aromatic group) and —NH—C(=NH)—NH$_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lypophilicity or hydrophobicity of natural amino acids which are hydrophilic.

A number of the suitable amino acids, amino acids analogs and salts thereof can be obtained commercially. Others can be synthesized by methods known in the art. Synthetic techniques are described, for example, in Greene and Wuts, "Protecting Groups in Organic Synthesis," John Wiley and Sons, Chapters 5 and 7 (1991).

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term "hydrophobic amino acid" refers to an amino acid that, on the hydrophobicity scale, has a value greater or equal to 0.5, or in other words, has a tendency to partition in the nonpolar acid which is at least equal to that of glycine.

Examples of amino acids which can be employed include, but are not limited to: glycine, proline, alanine, cysteine, methionine, valine, leucine, tyrosine, isoleucine, phenylalanine and tryptophan. Preferred hydrophobic amino acids include leucine, isoleucine, alanine, valine, phenylalanine and glycine. Combinations of hydrophobic amino acids can also be employed. Furthermore, combinations of hydrophobic and hydrophilic (preferentially partitioning in water) amino acids, where the overall combination is hydrophobic, can also be employed.

Leucine is the most preferred amino acid. The particles of the instant invention can comprise leucine in a concentration of at least about 40 weight percent. Preferably, the particles comprise at least about 50, 60, or 70 weight percent leucine. For example, the particles can comprise about 60 to about 95, about 70 to about 95, or about 72 to about 91 weight percent leucine.

In one preferred embodiment, particles are spray dried and comprise the hydrophobic amino acid leucine. Without being held to any particular theory, it is believed that due to their hydrophobicity and low water solubility, hydrophobic amino acids, such as leucine, facilitate the formation of a shell during the drying process when an ethanol/water co-solvent mixture is employed. It is also believed that the amino acids may alter the phase behavior of any phospholipids present in such a way as to facilitate the formation of a shell during the drying process.

The particles can additionally comprise a material having a carboxylate moiety. In one embodiment of the invention, the carboxylate moiety includes at least two carboxyl groups. Carboxylate moieties can be provided by carboxylic acids, salts thereof, as well as by combinations of two or more carboxylic acids and/or salts thereof. In a preferred embodiment, the carboxylate moiety is a hydrophilic carboxylic acid or a salt thereof. Suitable carboxylic acids include but are not limited to hydroxydicarboxylic acids (e.g., monohydroxydicarboxylic and dihydroxydicarboxylic acids), hydroxytricarboxilic acids (e.g., monohydroxytri-carboxylic and dihydroxytricarboxylic acids), and the like. Citric acid and citrates such as, for example, sodium citrate and tartaric acid and tartrates such as, for example, sodium tartrate are preferred.

The material having a carboxylate moiety can be present in the particles in an amount ranging from about 5 to about 80 percent by weight or about 5 to about 50 weight percent. Preferably, the material having a carboxylate moiety is present in the particles in an amount of about 10 to about 30 percent by weight. In one embodiment, the material having a carboxylate moiety is a salt of a carboxylic acid, preferably sodium citrate. Sodium citrate can be present in the particles at a concentration of about 5 to about 50, about 5 to about 40, about 10 to about 30, or about 15 to about 25 weight percent. Preferably, sodium citrate is present in the particles at a concentration of about 18 to about 22 weight percent, for example, about 20 weight percent. In another preferred embodiment, the salt of a carboxylic acid is sodium tartrate. Sodium tartrate can be present in the particles at a concentration of about 2 to about 50, about 5 to about 40, about 10 to about 30, or about 10 to about 20 weight percent. Preferably, sodium tartrate is present in the particles at a concentration of about 15 to about 20 weight percent, for example, about 16 weight percent. In another preferred embodiment, sodium tartrate is present in the particles in a concentration sufficient to adjust the pH of the solution from which the particles are formed to between about pH 4 and about pH 5, for example, to between about pH 4 and about pH 4.5. For example, if the epinephrine content of the particles is low (e.g., about 5 weight percent or less), the sodium tartrate concentration needed would also be low (e.g., about 2 or 3 weight percent); if the epinephrine content of the particles is higher, the sodium tartrate concentration needed would also be higher.

The particles also can include a salt comprising at least one multivalent cation or anion. As used herein, a "multivalent" cation or anion includes divalent ions. In a preferred embodiment, the salt comprises at least one divalent cation or anion.

The salt is preferably a salt of an alkaline-earth metal, such as, for example, calcium chloride. The particles of the invention can also include mixtures or combinations of salts.

The salt comprising at least one multivalent cation or anion can be present in the particles in an amount ranging from about 1 to about 40, about 5 to about 30, or about 5 to about 20 percent by weight. Preferably, the salt comprising at least one multivalent cation or anion is calcium chloride and is present in the particles in a concentration of about 1 to about 40, about 5 to about 30, about 5 to about 20, or, preferably, about 5 to about 15 weight percent. For example, the salt comprising at least one multivalent cation or anion is calcium chloride and is present in the particles in a concentration of about 10 weight percent.

The particles can also comprise a non-reducing sugar, e.g., sucrose, trehalose, or fructose. Sucrose is preferred. Combinations of non-reducing sugars also can be employed. The amount of non-reducing sugar(s), e.g., sucrose, present in the particles of the invention generally is less than about 40 weight percent, preferably less than about 30 weight percent and most preferably less than about 20 weight percent, for example, about 15 weight percent. In one embodiment, sucrose is present in the particles in a concentration of about 1 to about 30 weight percent, preferably about 10 to about 20 weight percent, for example, about 15 weight percent.

Without wishing to be held to a particular interpretation of the invention, it is believed that non-reducing sugars enhance the stability of a drug, such as epinephrine, that has chemical groups, e.g., an amine group, that can potentially react with a sugar that is reducing, e.g., lactose. It is further believed the presence of non-reducing sugars rather than reducing sugars also can benefit compositions that include other bioactive agents or drugs, such as, for example, Carbidopa, Levodopa, and other catecholamines.

The particles of the instant invention can further comprise components such as antioxidants to further stabilize the epinephrine active agent. The particles may comprise one or more antioxidants. Preferred antioxidants include, but are not limited to, oxygen scavengers or reducing agents such as sodium metabisulfite; metal chelators such as ethylenediamine tetra-acetic acid (EDTA) or salts thereof (e.g., disodium EDTA); phenolic antioxidants such as Vitamin E (alpha tocopherol); or any combination thereof. Other suitable antioxidants include cysteine, cysteamine, butylated hydroxytoluene (BHT), and ascorbic acid (Vitamin C). In one embodiment, the particles contain up to about 25 percent by weight antioxidant(s). In other embodiments, the particles contain up to about 15, up to about 10, up to about 5, or up to about 2 percent by weight antioxidant(s).

In one advantageous embodiment, the particles are substantially antioxidant-free. The term "substantially antioxidant-free," as that term is used herein, refers to containing no more than about 2 percent antioxidant(s) by weight, for example, no more than about 1, no more than about 0.5, no more than about 0.25, or no more than about 0.05 percent antioxidant(s) by weight. In one embodiment, the substantially antioxidant-free particles contain no antioxidant(s).

The particles can also include other materials such as, for example, buffer salts, sugars, cholesterol, dextran, polysaccharides, lactose, mannitol, maltodextrin, cyclodextrins, proteins, peptides, polypeptides, fatty acids, fatty acid esters, inorganic compounds, phosphates, and lipids.

In one embodiment of the invention, the particles include a material which enhances the release kinetics of the medicament. Examples of suitable such materials include, but are not limited to, certain phospholipids, amino acids, and carboxylate moieties combined with salts of multivalent metals.

The particles and respirable compositions comprising the particles of the invention may optionally include a surfactant, such as a surfactant which is endogenous to the lung. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration. Both naturally-occurring and synthetic lung surfactants are encompassed in the scope of the invention.

In addition to lung surfactants such as, for example, phospholipids discussed above, suitable surfactants include, but are not limited to, hexadecanol; fatty alcohols, such as polyethylene glycol (PEG); polyoxyethylene-9-lauryl ether; a surface active fatty acid, such as palmitic acid or oleic acid; glycocholate; surfactin; a poloxomer; a sorbitan fatty acid ester, such as sorbitan trioleate (Span 85); and tyloxapol.

A surfactant can be present in the particles in an amount ranging from more than about 1 to about 70 weight percent. In one embodiment, at least about 40 weight percent surfactant is present in the particles, for example, about 50 to about 70 weight percent surfactant.

In one aspect, the present invention is directed to particles for delivery of epinephrine to the respiratory system and methods for treating a patient in need of epinephrine, wherein the method comprises administering an effective amount of the particles to the respiratory system of a patient. Preferred particle formulations exhibiting acceptable chemical and physical characteristics and suitable for the purposes of the instant invention include (1) particles comprising epinephrine, or a salt thereof; a carboxylic acid, or a salt thereof; a salt comprising at least one multivalent cation or anion; and a phospholipid; (2) particles comprising epinephrine, or a salt thereof; an amino acid; and a sugar; (3) particles comprising epinephrine, or a salt thereof; and an amino acid; (4) particles comprising epinephrine, or a salt thereof; an amino acid; and a carboxylic acid, or a salt thereof.

Preferred particles for delivery of epinephrine to the respiratory system comprise: (a) about 6 to about 25 weight percent epinephrine bitartrate; (b) about 62 to about 82 weight percent leucine; and (c) about 2 to about 22 weight percent sodium tartrate. For example, the particles can comprise (a) about 11 to about 21 weight percent epinephrine bitartrate; (b) about 62 to about 82 weight percent leucine; and (c) about 7 to about 17 weight percent sodium tartrate. Other preferred particles for delivery of epinephrine to the respiratory system comprise (a) about 7 to about 28 weight percent epinephrine bitartrate; and (b) about 72 to about 92 weight percent leucine. For example, the particles can comprise (a) about 12 to about 23 weight percent epinephrine bitartrate; and (b) about 77 to about 88 weight percent leucine.

A preferred method for treating a patient in need of epinephrine comprises administering an effective amount of particles to the respiratory system of a patient wherein the particles comprise (a) about 6 to about 25 weight percent epinephrine bitartrate; (b) about 62 to about 82 weight percent leucine; and (c) about 2 to about 22 weight percent sodium tartrate. For example, the particles can comprise (a) about 11 to about 21 weight percent epinephrine bitartrate; (b) about 67 to about 77 weight percent leucine; and (c) about 7 to about 17 weight percent sodium tartrate. Another preferred method for treating a patient in need of epinephrine comprises administering an effective amount of particles to the respiratory system of a patient wherein the particles comprise (a) about 7 to about 28 weight percent epinephrine bitartrate; and (b) about 72 to about 92 weight percent leucine. For example, the particles can comprise (a) about 12 to about 23 weight percent epinephrine bitartrate; and (b) about 77 to about 87 weight percent leucine.

In one embodiment, the particles possess rapid epinephrine release properties. Rapid release properties allow the particles of the present invention to be used in rescue therapy as described herein.

In another embodiment, particles of the present invention are capable of releasing epinephrine in a sustained fashion. As such, the particles can be said to possess sustained release properties. "Sustained release" as that term is used herein, refers to an increase in the time period over which an agent is released from a particle of the present invention as compared to an appropriate control, such as for example, as compared to the time period over which an agent is released from an particle that does not comprise epinephrine, or a salt thereof, and a phospholipid or combination of phospholipids. "Sustained release," as that term is used herein, may also refer to a reduction in the availability, or burst, of agent typically seen soon after administration. For example, "sustained release" can refer to a reduction in the availability of epinephrine in the first half-hour or the first hour following administration, that is, a reduction in the initial burst of epinephrine.

"Sustained release," as that term is used herein, may also refer to a higher amount of epinephrine retained or remaining in the particles after the initial burst as compared to an appropriate control. "Sustained release" is also known to those experienced in the art as "modified release," "prolonged release," or "extended release." "Sustained release," as used herein, also encompasses "sustained action" or "sustained effect." "Sustained action" and "sustained effect," as those terms are used herein, can refer to an increase in the time period over which epinephrine performs its therapeutic activity as compared to an appropriate control. "Sustained action" is also known to those experienced in the art as "prolonged action" or "extended action."

Particles for inhalation possessing sustained drug release properties, and methods for their administration, are also described in U.S. patent application Ser. No. 09/644,736, entitled "Modulation Of Release From Dry Powder Formulations," filed on Aug. 23, 2000; U.S. patent application Ser. No. 09/792,869, entitled "Modulation Of Release From Dry Powder Formulations," filed on Feb. 23, 2001; and U.S. Patent Application No. 60/366,497, entitled "Inhalable Sustained Therapeutic Formulations," filed on Mar. 20, 2002. The contents of each of these three applications are incorporated herein in their entirety.

Without being held to any particular theory, Applicants believe that the advantages provided by particles of the instant invention may be influenced, among other factors, by the rate of epinephrine release from the particles. Drug release rates can be described in terms of the half-time of release of a bioactive agent from a formulation. As used herein the term "half-time" refers to the time required to release 50% of the initial epinephrine payload contained in the particles. In one embodiment, the particles of the present invention have a half-time of release of epinephrine from the particles of about 1 to about 20 minutes. In another embodiment, the particles are formulated for extended release of epinephrine and have a longer half-time of release such as, for example, about an hour or more.

Drug release rates can also be described in terms of release constants. The first order release constant can be expressed using one of the following equations:

$$M_{pw(t)} = M_{(\infty)} * e^{-k*t} \tag{1}$$

or, $$M_{(t)} = M_{(\infty)} * (1 - e^{-k*t}) \tag{2}$$

Where k is the first order release constant. $M_{(\infty)}$ is the total mass of drug in the drug delivery system, e.g. the dry powder, and $M_{pw(t)}$ is drug mass remaining in the dry powders at time t. $M_{(t)}$ is the amount of drug mass released from dry powders at time t. The relationship can be expressed as:

$$M_{(\infty)} = M_{pw(t)} + M_{(t)} \tag{3}$$

Equations (1), (2) and (3) may be expressed either in amount (i.e., mass) of drug released or concentration of drug released in a specified volume of release medium.

For example, Equation (2) may be expressed as:

$$C_{(t)} C_{(\infty)} * (1 - e^{-k*t}) \tag{4}$$

Where k is the first order release constant. $C_{(\infty)}$ is the maximum theoretical concentration of drug in the release medium, and $C_{(t)}$ is the concentration of drug being released from dry powders to the release medium at time t.

The 'half-time' or $t_{50\%}$ for a first order release kinetics is given by the well-known equation, $$t_{50\%} = 0.693/k \tag{5}$$

Drug release rates in terms of first order release constant and $t_{50}\%$ may be calculated using the following equations:

$$k = -\ln(M_{pw(t)}/M_{(\infty)})/t \tag{6}$$

or, $$k = -\ln(M_{(\infty)} - M_{(t)}/M_{(\infty)})/t \tag{7}$$

In one embodiment, the particles of the invention have extended epinephrine release properties in comparison to the pharmacokinetic/pharmacodynamic profile of epinephrine administered as conventional formulations, such as by intravenous injection (IV), intramuscular injection (IM), subcutaneous injection, auto-injection, or liquid aerosol inhalation routes.

In a preferred embodiment, the particles possess aerosol characteristics that permit effective delivery of the particles to the respiratory system without the use of propellents.

The particles of the present invention have a preferred size, e.g., a volumetric median geometric diameter (VMGD) of at least about 5 microns. In one embodiment of the invention, the VMGD of the particles is about 5 to about 30 microns. Preferably, the particles have a VMGD of about 5 to about 15 microns or, alternatively, about 15 to about 30 microns. The particles can have a median diameter, mass median diameter (MMD), a mass median envelope diameter (MMED) or a mass median geometric diameter (MMGD) of at least about 5 microns, for example about 5 to about 30 microns such as about 5 to about 15 microns.

The diameter of the particles, for example, their VMGD, can be measured using an electrical zone sensing instrument such as a Multisizer He, (Coulter Electronic, Luton, Beds, England), or a laser diffraction instrument such as HELOS (Sympatec, Princeton, N.J.). Other instruments for measuring particle geometric diameter are well known in the art. The diameter of particles in a sample will range depending upon factors such as particle composition and methods of synthesis. The distribution of size of particles in a sample can be selected to permit optimal deposition within targeted sites within the respiratory system.

Particles suitable for use in the present invention may be fabricated and then separated, for example, by filtration or centrifugation, to provide a particle sample with a preselected size distribution. For example, greater than about 30, 50, 70, or 80% of the particles in a sample can have a diameter within a selected range of at least about 5 microns. The selected range within which a certain percentage of the particles must fall may be, for example, between about 5 and about 30 microns or, optionally, between about 5 and about 15 microns. The particle sample also can be fabricated wherein at least about 90% or, optionally, about 95 to about 99% of the particles, have a diameter within the selected range.

In one embodiment, the interquartile range of the particle sample may be 2 microns, with a mean diameter for example, between about 7.5 and about 13.5 microns. Thus, for example, at least about 30 to about 40% of the particles may have diameters within the selected range. The said percentages of particles can have diameters within a 1 micron range, for example, between 5 and 6; 6 and 7; 7 and 8; 8 and 9; 9 and 10; 10 and 11; 11 and 12; 12 and 13; 13 and 14; or 14 and 15 microns.

Particle aerodynamic diameter can also be used to characterize the aerosol performance of a composition. In one embodiment, the particles have a mass median aerodynamic diameter (MMAD) of about 1 to about 5 microns. In preferred embodiments, the particles have a MMAD of about 1 to about 3 microns, about 2 to about 4 microns, or about 3 to about 5 microns.

Experimentally, aerodynamic diameter can be determined using time of flight (TOF) measurements. For example, an instrument such as the Model 3225 Aerosizer DSP Particle Size Analyzer (Amherst Process Instrument, Inc., Amherst, Mass.) can be used to measure aerodynamic diameter. The Aerosizer measures the time taken for individual particles to pass between two fixed laser beams. The instrument subsequently uses this TOF data to solve a force balance on the particles and aerodynamic diameter is determined based on the relationship $$d_{aer} = d\sqrt{\rho} \tag{8}$$

where $d_{aer}$ is the aerodynamic diameter of the particle; d is the diameter of the particle; and _ is the particle density.

Aerodynamic diameter also can be experimentally determined by employing a gravitational settling method, whereby the time for an ensemble of particles to settle a certain distance is used to infer directly the aerodynamic diameter of the particles. Indirect methods for measuring the mass median aerodynamic diameter are the Andersen Cascade Impactor and the multi-stage liquid impinger (MSLI). The methods and instruments for measuring particle aerodynamic diameter are well known in the art.

In a preferred embodiment of the invention, particles administered to a subject's respiratory system have a tap density of less than about 0.4 g/cm$^3$. Particles having a tap density of less than about 0.4 g/cm$^3$ are referred to herein as "aerodynamically light." In other preferred embodiments, the particles have a tap density less than or equal to about 0.3 g/cm$^3$ or less than or equal to about 0.2 g/cm$^3$. In other embodiments, the particles have a tap density less than or equal to about 0.1 g/cm$^3$, or less than or equal to about 0.05 g/cm$^3$. Tap density is a measure of the envelope mass density characterizing a particle. The envelope mass density of a particle of a statistically isotropic shape is defined as the mass of the particle divided by the minimum sphere envelope volume within which it can be enclosed. Features which can contribute to low tap density include irregular surface texture and porous structure.

Tap density can be measured by using instruments known to those skilled in the art such as the Dual Platform Microprocessor Controlled Tap Density Tester (Vankel, N.C.) or a GeoPyc™ instrument (Micrometrics Instrument Corp., Norcross, Ga.). Tap density can be determined using the method of USP Bulk Density and Tapped Density, United States Pharmacopia convention, Rockville, Md., 10$^{th}$ Supplement, 4950-4951, 1999.

In a preferred embodiment, particles of the present invention can be characterized as aerodynamically light. Aerodynamically light particles have a preferred size, e.g., a volume median geometric diameter (VMGD) of at least about 5 microns. In a preferred embodiment of the invention, the VMGD of the particles is about 5 to about 30 microns. Aerodynamically light particles also preferably have a mass median aerodynamic diameter (MMAD), also referred to herein as "aerodynamic diameter," of about 1 to about 5 microns. In one preferred embodiment of the invention, the MMAD of the particles is about 1 to about 5 microns.

Process conditions as well as inhaler efficiency, in particular with respect to dispersibility, can contribute to the size of particles that can be delivered to the respiratory system. Aerodynamically light particles may be fabricated or separated, for example, by filtration or centrifugation to provide a particle sample with a preselected size distribution.

Aerodynamically light particles with a tap density less than about 0.4 g/cm$^3$, median diameters of at least about 5 microns, and an aerodynamic diameter of between about 1 and about 5 microns, preferably between about 1 and about 3 microns, are more capable of escaping inertial and gravitational deposition in the oropharyngeal region, and are targeted to the airways or the deep lung. The use of larger, more porous particles is advantageous since they are able to aerosolize more efficiently than smaller, denser aerosol particles such as those conventionally used for inhalation therapies.

In comparison to smaller, relatively dense particles, the larger aerodynamically light particles, preferably having a median diameter of at least about 5 microns, also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond about 3 microns. Kawaguchi, H., et al., *Biomaterials* 7:61-66 (1986); Krenis, L. J. and Strauss, B., *Proc. Soc. Exp. Med.*, 107:748-750 (1961); and Rudt, S, and Muller, R. H., *J. Contr. Rel.*, 22:263-272 (1992). For particles of statistically isotropic shape, such as spheres with rough surfaces, the particle envelope volume is approximately equivalent to the volume of cytosolic space required within a macrophage for complete particle phagocytosis.

Aerodynamically light particles thus are capable of a longer term release of an entrapped agent to the lungs. Following inhalation, aerodynamically light biodegradable particles can deposit in the lungs and subsequently undergo sustained degradation and drug release without the majority of the particles being phagocytosed by alveolar macrophages. Epinephrine can be delivered relatively slowly into the alveolar fluid and at a controlled rate into the blood stream, minimizing possible toxic responses of exposed cells to an excessively high concentration of the drug. The aerodynamically light particles thus are highly suitable for inhalation therapies, particularly in controlled release applications.

The particles may be fabricated with the appropriate material, surface roughness, diameter and tap density for localized delivery to selected regions of the respiratory system such as the deep lung or upper or central airways. For example, higher density or larger particles may be used for upper airway delivery, or a mixture of varying size particles in a sample, provided with the same or a different therapeutic agent, may be administered to target different regions of the lung in one administration. Particles having an aerodynamic diameter ranging from about 3 to about 5 microns are preferred for delivery to the central and upper airways. Particles having an aerodynamic diameter ranging from about 1 to about 3 microns are preferred for delivery to the deep lung.

Inertial impaction and gravitational settling of aerosols are predominant deposition mechanisms in the airways and acini of the lungs during normal breathing conditions. Edwards, D. A., *J. Aerosol Sci.*, 26: 293-317 (1995). The importance of both deposition mechanisms increases in proportion to the mass of aerosols and not to particle (or envelope) volume. Since the site of aerosol deposition in the lungs is determined by the mass of the aerosol (i.e., at least for particles of mean aerodynamic diameter greater than approximately 1 micron), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," in *Topics in Pharmaceutical Sciences* 1991 (eds. D. J. A. Crommelin and K. K. Midha), pp. 95-117, Stuttgart: Medpharm Scientific Publishers, 1992)), by the formula:

$$d_{aer}=d\sqrt{\rho} \tag{9}$$

where the envelope mass density, _ is in units of g/cm³. Maximal deposition of monodispersed aerosol particles in the alveolar region of the human lung (~60%) occurs for an aerodynamic diameter of approximately $d_{aer}=3$ microns. Heyder, J. et al., *J. Aerosol Sci.*, 17:811-825 (1986).

Due to their small envelope mass density, the actual diameter, d, of aerodynamically light particles comprising a monodisperse inhaled powder that will exhibit maximum deep-lung deposition is:

$$d=3/\sqrt{\rho} \mu m \text{ (where } \rho<1 \text{ g/cm}^3\text{)}; \tag{10}$$

where d is always greater than 3 microns. For example, aerodynamically light particles that display an envelope mass density, _=0.1 g/cm³, will exhibit a maximum deposition for particles having envelope diameters as large as 9.5 microns. The increased particle size diminishes interparticle adhesion forces. Visser, J., *Powder Technology*, 58:1-10. Thus, large particle size increases efficiency of aerosolization to the deep lung for particles of low envelope mass density, in addition to contributing to lower phagocytic losses.

The aerodynamic diameter is calculated to provide for maximum deposition within the lungs, previously achieved by the use of very small particles of less than about 5 microns in diameter, preferably between about 1 and about 3 microns, which are then subject to phagocytosis. Selection of particles which have a larger diameter, but which are sufficiently light (hence the characterization "aerodynamically light"), results in an equivalent delivery to the lungs, but the larger size particles are not phagocytosed. Improved delivery can be obtained by using particles with a rough or uneven surface relative to those with a smooth surface.

Mass density and the relationship between mass density, mean diameter and aerodynamic diameter are discussed in U.S. application Ser. No. 08/655,570, filed on May 24, 1996, which is incorporated herein by reference in its entirety.

Fine particle fraction can be used as one way to characterize the aerosol performance of a dispersed powder. Fine particle fraction describes the size distribution of airborne particles. Gravimetric analysis, using Cascade impactors, is one method of measuring the size distribution, or fine particle fraction, of airborne particles. The Andersen Cascade Impactor (ACI) is an eight-stage impactor that can separate aerosols into nine distinct fractions based on aerodynamic size. The size cutoffs of each stage are dependent upon the flow rate at which the ACI is operated.

A two-stage collapsed ACI also can be used to measure fine particle fraction. The two-stage collapsed ACI consists of only the top two stages of the eight-stage ACI and allows for the collection of two separate powder fractions. The ACI is made up of multiple stages consisting of a series of nozzles (i.e., a jet plate) and an impaction surface (i.e., an impaction disc). At each stage an aerosol stream passes through the nozzles and impinges upon the surface. Particles in the aerosol stream with a large enough inertia will impact upon the plate. Smaller particles that do not have enough inertia to impact on the plate will remain in the aerosol stream and be carried to the next stage. Each successive stage of the ACI has a higher aerosol velocity in the nozzles so that smaller particles can be collected at each successive stage.

In one embodiment, the particles of the invention are characterized by fine particle fraction. A two-stage collapsed Andersen Cascade Impactor is used to determine fine particle fraction. Specifically, a two-stage collapsed ACI is calibrated so that the fraction of powder that is collected on stage one is composed of particles that have an aerodynamic diameter of less than 5.6 microns and greater than 3.4 microns. The fraction of powder passing stage one and depositing on a collection filter is thus composed of particles having an aerodynamic diameter of less than 3.4 microns. The airflow at such a calibration is approximately 60 L/min.

The terms "FPF(<5.6)," "FPF(<5.6 microns)," and "fine particle fraction of less than 5.6 microns" as used herein, refer to the fraction of a sample of particles that have an aerodynamic diameter of less than 5.6 microns. FPF(<5.6) can be determined by dividing the mass of particles deposited on the stage one and on the collection filter of a two-stage collapsed ACI by the mass of particles weighed into a capsule for delivery to the instrument.

The terms "FPF(<3.4)," "FPF(<3.4 microns)," and "fine particle fraction of less than 3.4 microns" as used herein, refer to the fraction of a mass of particles that have an aerodynamic diameter of less than 3.4 microns. FPF(<3.4) can be determined by dividing the mass of particles deposited on the collection filter of a two-stage collapsed ACI by the mass of particles weighed into a capsule for delivery to the instrument.

The FPF(<5.6) has been demonstrated to correlate to the fraction of the powder that is able to make it into the lung of the patient, while the FPF(<3.4) has been demonstrated to correlate to the fraction of the powder that reaches the deep lung of a patient. These correlations provide a quantitative indicator that can be used for particle optimization.

A three-stage collapsed Andersen Cascade Impactor can also be used to determine fine particle fraction. Optionally, the three-stage collapsed ACI comprises wetted screens that are used to help diminish particle bounce and re-entrainment. The three-stage collapsed ACI is calibrated so that the fraction of powder that is collected on a collection filter is composed of particles having an aerodynamic diameter of less than 3.3 microns. The airflow at such a calibration is approximately 28 L/min. The terms "FPF(<3.3)," "FPF(<3.3 microns)," and "fine particle fraction of less than 3.3 microns" as used herein, refer to the fraction of a mass of particles that have an aerodynamic diameter of less than 3.3 microns. FPF (<3.3) can be determined by dividing the mass of particles deposited on the collection filter of a three-stage collapsed ACI by the mass of particles weighed into a capsule for delivery to the instrument.

A Multi-Stage Liquid Impinger (MSLI) is another device that can be used to measure fine particle fraction. The Multi-stage liquid Impinger operates on the same principles as the Anderson Cascade Impactor, although instead of eight stages, MSLI has five. Additionally, each MSLI stage consists of an ethanol-wetted glass frit instead of a solid plate. The wetted stage is used to prevent particle bounce and re-entrainment, which can occur when using the ACI.

In one embodiment, a mass of particles of the invention has an FPF(<5.6) of at least about 30%, 35%, 40%, 45% or 50%. In another embodiment, a mass of particles has an FPF (<3.4) of at least about 5%, 10%, 15%, or 20%.

In one aspect the present invention is directed to spray dried particles for delivery of epinephrine to the respiratory system wherein the particles comprise epinephrine, or a salt thereof; and at least one pharmaceutically acceptable excipient; wherein the particles possess a fine particle fraction of less than 5.6 microns of at least about 45 percent. In another aspect the invention is directed to spray dried particles for delivery of epinephrine to the respiratory system wherein the particles comprise epinephrine, or a salt thereof; and at least one pharmaceutically acceptable excipient; wherein the particles possess a fine particle fraction of less than 3.4 microns of at least about 15 percent.

The particles of the invention can be characterized by the chemical stability of the epinephrine that the particles comprise. Without being held to any particular theory, it is believed that several factors can influence the chemical stability of the epinephrine. These factors can include the materials comprising the particles, the stability of the agent itself, interactions between the agent and excipients, and interactions between agents. The chemical stability of the constituent epinephrine can effect important characteristics of a pharmaceutical composition including shelf-life, proper storage conditions, acceptable environments for administration, biological compatibility, and effectiveness of the epinephrine. Chemical stability can be assessed using techniques well known in the art. One example of a technique that can be used to assess chemical stability is reverse phase high performance liquid chromatography (RP-HPLC).

Particles of the invention include epinephrine that is generally stable over a period of at least about 1 year. In one embodiment, at least about 90%, e.g., about 95%, of epinephrine contained in the particles is not degraded as measured by HPLC over a period of at least about 1 year.

The epinephrine, or salt thereof, contained in the particles can be substantially crystalline, semi-crystalline, or substantially amorphous. Without being held to any particular theory, Applicants believe that the epinephrine, or salt thereof, as found in the particles is semi-crystalline or substantially amorphous or in a dispersed form. The pharmaceutically acceptable excipient contained in the particles can be substantially crystalline, semi-crystalline, or substantially amorphous depending upon such factors as spray drying conditions and upon the characteristics of the particular excipient.

In one embodiment, the particles comprise epinephrine in a substantially amorphous or dispersed form in a semi-crystalline excipient matrix (e.g., a leucine matrix). The dispersed form of epinephrine can range from nano-scale domains (i.e., sizes less than about 0.1 microns in characteristic width) of amorphous epinephrine in a semi-crystalline excipient matrix to a solid solution of epinephrine and semi-crystalline excipient.

FIG. 1A shows X-Ray Powder Diffraction (XRPD) data for bulk epinephrine bitartrate. The well resolved peaks and reproducible scans demonstrate crystalline, thermally stable behavior up to 145° C. FIG. 1B shows XRPD data for bulk leucine at 25° C. The well resolved peaks are characteristic of crystalline material. FIG. 1C shows XRPD data for spray dried particles containing leucine, epinephrine bitartrate, and sodium bitartrate. The observable peaks in this data are characteristic of leucine only, indicating that epinephrine is present in an amorphous or dispersed form.

Applicants believe that improved physical stability results from the semi-crystalline or amorphous state of epinephrine in the instant particles and that this physical stability of the epinephrine phase may provide improved epinephrine chemical stability. Furthermore, improved dissolution properties seem to result from particles that comprise a semi-crystalline or amorphous phase of epinephrine in a semi-crystalline excipient matrix.

Methods of preparing and administering particles which are aerodynamically light and include surfactants, and, in particular phospholipids, are disclosed in U.S. Pat. No. 5,855,913, issued on Jan. 5, 1999 to Hanes, et al., and in U.S. Pat. No. 5,985,309, issued on Nov. 16, 1999 to Edwards, et al. The teachings of both are incorporated herein by reference and in their entirety.

Highly dispersible particles suitable for use in the methods of the invention may be prepared using single and double emulsion solvent evaporation, spray drying, solvent extraction, solvent evaporation, phase separation, simple and complex coacervation, interfacial polymerization, supercritical carbon dioxide ($CO_2$) and other methods well known to those of ordinary skill in the art. Particles may be made using methods for making microspheres or microcapsules known in the art, provided that the conditions are optimized for forming particles with the desired aerodynamic properties (e.g., aerodynamic diameter and geometric diameter) or additional steps are performed to select particles with the density and diameter sufficient to provide the particles with an aerodynamic diameter between about 1 and about 5 microns, preferably between about 1 and about 3 microns, or alternatively between about 3 and about 5 microns.

If the particles prepared by any of the above methods have a size range outside of the desired range, particles can be sized, for example, using a sieve, and further separated according to density using techniques known to those of skill in the art. The particles are preferably spray dried. Suitable spray-drying techniques are described, for example, by K. Masters in "Spray Drying Handbook", John Wiley & Sons, New York (1984). Generally, during spray-drying, heat from a hot gas such as heated air or nitrogen is used to evaporate a solvent from droplets formed by atomizing a continuous liquid feed.

An organic solvent or an aqueous-organic solvent can be employed to form a feed for spray drying the particles of the present invention. Suitable organic solvents that can be employed include but are not limited to alcohols such as, for example, ethanol, methanol, propanol, isopropanol, butanols, and others. Other organic solvents include but are not limited to perfluorocarbons, dichloromethane, chloroform, ether, ethyl acetate, methyl tert-butyl ether and others. Co-solvents that can be employed include an aqueous solvent and an organic solvent, such as, but not limited to, the organic solvents as described above. Aqueous solvents include water and buffered solutions. In one embodiment, an ethanol/water solvent is preferred with the ethanol solution to water solution ratio ranging from about 70:30 to about 30:70 by volume.

The mixture can have a neutral, acidic or alkaline pH. Optionally, a pH buffer can be added to the solvent or co-solvent or to the formed mixture. The pH of the mixture can range from about 3 to about 8. An acidic pH is preferred in mixtures that comprise epinephrine, or a salt thereof. In one embodiment, the pH of the mixture is between about 4 and about 5, for example, between about 4.0 and about 4.5 or between about 4.1 and about 4.4. For example, a mixture can be formed that comprises leucine, epinephrine bitartrate and sodium tartrate wherein sodium tartrate is present in an amount such that the pH of the resulting solution is between about 4.1 and about 4.4.

In one aspect, organic soluble particle components are dissolved in an organic phase and water soluble particle components are dissolved in an aqueous phase. The solutions are heated as necessary to assure solubility. In a preferred embodiment, ethanol soluble particle components are dissolved in an ethanol phase and water soluble particle components are dissolved in an aqueous phase.

Solutions containing particle components are combined or mixed prior to spray drying. For example, in one aspect of the present invention the solutions are bulk mixed prior to being fed to the spray dryer. In one embodiment, the solutions are combined or mixed such that the resulting solution has a total dissolved solids concentration of about 1 g/L. Preferably, the dissolved solids concentration is greater than about 1 g/L, for example about 5, 10, or 15 g/L. Solutions containing particle components can be combined or mixed using a static mixing device prior to spray drying.

In one aspect of the present invention, a hydrophillic component and a hydrophobic component are prepared. The hydrophobic and hydrophilic components are then combined in a static mixer to form a combination. The combination is atomized to produce droplets, which are dried to form dry particles. In a preferred aspect of this method, the atomizing step is performed immediately after the components are combined in the static mixer.

A method for preparing a dry powder composition also is disclosed herein. In such a method, first and second components are prepared, one or both of which comprise epinephrine or a salt thereof. The first and second components are combined in a static mixer to form a combination. In one embodiment, the first and second components are physically and/or chemically incompatible with each other. The first and second components can be such that combining them causes degradation in one of the components. In another aspect, a material present in the first component is incompatible with a material present in the second component. The combination is atomized to produce droplets that are dried to form dry particles. Preferably the first component comprises epinephrine, or a salt thereof, and one or more excipients dissolved in an aqueous solvent, and the second component comprises one or more excipients dissolved in an organic solvent.

For example, in one method for preparing a dry powder composition, a first phase is prepared by combining a solution that comprises water, sodium citrate, and calcium chloride with a solution that comprises water, epinephrine free base, and hydrochloric acid. A second phase is prepared that comprises ethanol and one or more phospholipids. One or both solutions may be separately heated as needed to assure solubility of their components. The first and second phases are combined in a static mixer to form a combination. The combination is atomized to produce droplets that are dried to form dry particles.

In one embodiment, the apparatus used for practice of the present invention includes a static mixer (e.g., a static mixer as more fully described in U.S. Pat. No. 4,511,258, the entirety of which is incorporated herein by reference, or other suitable static mixers such as, but not limited to, Model 1/4-21, made by Koflo Corporation.) having an inlet end and an outlet end. The static mixer is operative to combine an aqueous component with an organic component to form a combination. Means are provided for transporting the aqueous component and the organic component to the inlet end of the static mixer. In a preferred aspect of this method, the aqueous and organic components are transported to the static mixer at substantially the same rate. An atomizer is in fluid communication with the outlet end of the static mixer to atomize the combination into droplets. The droplets are dried to form dry particles.

The apparatus used to practice the present invention also can include a geometric particle sizer that determines a geometric diameter of the dry particles, and an aerodynamic particle sizer that determines an aerodynamic diameter of the dry particles.

Methods and apparatus for producing dry particles are discussed in co-pending U.S. application Ser. No. 10/101, 563, entitled "Method and Apparatus for Producing Dry Particles," filed on Mar. 20, 2002, the entirety of which is incorporated herein by reference.

Spray drying solutions prepared as described above are distributed to a drying vessel via an atomization device. For example, a nozzle or a rotary atomizer may be used to distribute the solutions to the drying vessel. In a preferred embodiment, a rotary atomizer is employed, such as a vaned rotary atomizer. For example, a rotary atomizer having a 4- or 24-vaned wheel may be used. Examples of suitable spray dryers using rotary atomization the Mobile Minor Spray Dryer or the Model PSD-1, both manufactured by Niro, Inc. (Denmark).

Actual spray drying conditions will vary depending in part on the composition of the spray drying solution and material flow rates. In some embodiments, the inlet temperature to the spray dryer is about 100 to about 200° C. Preferably, the inlet temperature is about 105 to about 190° C.

The spray dryer outlet temperature will vary depending upon such factors as the feed temperature and the properties of the materials being dried. In one embodiment, the outlet temperature is about 35 to about 80° C. In another embodiment, the outlet temperature is about 40 to about 70° C.

Optionally, the particles include, a small amount of a strong electrolyte salt such as the preferred salt, sodium chloride (NaCl). Other salts that can be employed include sodium phosphate, sodium fluoride, sodium sulfate and calcium carbonate. Generally, the amount of salt present in the particles is less than 10 weight percent, preferably less than 5 weight percent.

Particles that comprise, by weight, greater than 90% of an agent, e.g., epinephrine, can have local areas of charges on the surface of the particles. This electrostatic charge on the surface of the particles causes the particles to behave in undesirable ways. For example, the presence of the electrostatic charge will cause the particles to stick to the walls of the spray drying chamber or to the pipe leading from the spray dryer or to stick within the baghouse thereby significantly reducing the percent yield obtained. Additionally, the electrostatic charge can tend to cause the particles to agglomerate when placed in a capsule based system. Dispersing these agglomerates can be difficult and that can manifest itself by either poor emitted doses, poor fine particle fractions, or both. Moreover, particle packing can also be affected by the presence of an electrostatic charge. Particles with like charges in close proximity will repel each other, leaving void spaces in the powder bed. This results in a given mass of particles with an electrostatic charge taking up more space than a given mass of the same powder without an electrostatic charge. Consequently, this limits the upper dose that can be delivered in a single receptacle.

Without wishing to be held to a particular interpretation of the invention, it is believed that a salt, such as NaCl, provides a source of mobile counterions and that the counterions associate with charged regions on the surface of the particles. It is believed that the addition of a small salt to particles that have local areas of charge on their surface will reduce the amount of static present in the final powder by providing a source of mobile counterions that would associate with the charged regions on the surface. Thereby the yield of the powder produced is improved by reducing powder agglomeration, improving the Fine Particle Fraction (FPF) and emitted dose of the particles and allowing for a larger mass of particles to be packed into a single receptacle.

Dry powder particles comprising a catecholamine and methods for their administration are further described in co-pending U.S. Provisional Application No. 60/366,471, entitled "Pulmonary Delivery for Levodopa," filed on Mar. 20, 2002, the entire contents of which are incorporated herein by reference.

The present invention provides methods for treating a patient in need of epinephrine. In various embodiments the methods comprise administering an effective amount of particles to the respiratory system wherein the particles comprise epinephrine, or a salt thereof. Epinephrine containing particles can be administered for a variety of reasons including, but not limited to, to stimulate the contraction of some smooth muscles and/or to relax other smooth muscles; to stimulate heart rate; to increase blood pressure; to stimulate glycogenolysis in the liver and/or muscle tissue; to stimulate lipolysis in adipose tissue; to treat bronchoconstriction, bronchospasm, airway constriction, and/or edema; and to treat anaphylaxis, shock, emphysema, chronic obstructive pulmonary disease (COPD), bronchitis, croup (e.g., postintubation and infectious), asthma, and/or allergic conditions.

The term "anaphylaxis," as that term is used herein, refers to a broad class of immediate-type hypersensitivity and anaphylactic conditions well known to those skilled in the art including, but not limited to, anaphylactoid reactions, anaphylactic shock, idiopathic anaphylaxis, allergen induced anaphylaxis, exercise induced anaphylaxis, exercise-induced food-dependent anaphylaxis, active anaphylaxis, aggregate anaphylaxis, antiserum anaphylaxis, generalized anaphylaxis, inverse anaphylaxis, local anaphylaxis, passive anaphylaxis, reverse anaphylaxis, and systemic anaphylaxis. An "episode" of anaphylaxis, as that term is used herein, refers to a continuous manifestation of anaphylaxis in a patient.

The term "respiratory system," as used herein, refers to the anatomical system that performs the respiration function, e.g., the airways, the lungs and their associated structures. The respiratory system includes the "respiratory tract," as it is known in the art. The respiratory system encompasses the upper airways, including the oropharynx and larynx, followed by the lower airways, which include the trachea followed by bifurcations into the bronchi and bronchioli. The upper and lower airways are called the conducting airways.

The terminal bronchioli then divide into respiratory bronchioli which then lead to the ultimate respiratory zone, the alveoli, or deep lung.

The present invention is directed, in part, to a method for treating a patient in need of epinephrine wherein the method comprises administering an effective amount of dry powder particles to the respiratory system of the patient. The particles of the invention can be used to provide controlled systemic and/or local delivery of epinephrine to the respiratory system via aerosolization. Administration of the particles to the lung by aerosolization permits delivery of relatively large diameter therapeutic aerosols, for example, greater than about 5 microns in median diameter. Porous or aerodynamically light particles, having a geometric size (or mean diameter) in the range of about 5 to about 30 microns, and tap density less than about 0.4 g/cm$^3$, such that they possess an aerodynamic diameter of about 1 to about 3 microns, have been shown to display ideal properties for delivery to the deep lung. Larger aerodynamic diameters, ranging, for example, from about 3 to about 5 microns are generally preferred, however, for delivery to the central and upper airways. Particles having a range of aerodynamic diameters may be co-administered to deliver epinephrine to a variety of sites in the respiratory system, for example, to deliver epinephrine to both the airways and to the deep lung.

The present invention also provides a method for treating a patient in need of epinephrine, wherein the method comprises administering an effective amount of substantially dry powder particles to the respiratory system of the patient and wherein the particles comprise epinephrine, or a salt thereof, and at least one pharmaceutically acceptable excipient. Suitable pharmaceutically acceptable excipient are described herein. Administration of particles to the respiratory system can be by means such as are known in the art. For example, the particles are delivered by inhalation. Preferably, the methods comprise administering an effective amount of particles that are substantially solvent-free and substantially propellent-free.

In one embodiment, the method for treating a patient in need of epinephrine comprises administering an effective amount of particles to the respiratory system of the patient, wherein the particles comprise epinephrine, or a salt thereof, and at least one pharmaceutically acceptable excipient and wherein the effective amount of particles possess a fine particle fraction of less than 5.6 microns of at least about 45 percent. In another, the method for treating a patient in need of epinephrine comprises administering an effective amount of particles to the respiratory system of the patient, wherein the particles comprise epinephrine, or a salt thereof, and at least one pharmaceutically acceptable excipient and wherein the effective amount of particles possess a fine particle fraction of less than 3.4 microns of at least about 15 percent.

The present invention also comprises a method for treating a patient in need of epinephrine wherein an effective amount of substantially dry particles is administered to the respiratory system of the patient, wherein the particles comprise epinephrine, or a salt thereof, and wherein a first portion of the particles is deposited in the airways of the respiratory system and a second portion of the particles is deposited to the alveoli region of the lungs. In one embodiment, the first portion of particles is deposited at a site or at sites of constriction or obstruction of the respiratory system. Examples of sites of constriction or obstruction include, but are not limited to, upper, lower, or both upper and lower airway constrictions; sites of airway smooth muscle constriction; bronchial obstructions, areas of inflammation or edema; and constrictions due to muscle spasm. Airways, as described herein, also include the upper oropharangeal and laryngeal regions. Without being held to any particular theory, Applicants believe that epinephrine released from the first portion of particles, deposited at a site or sites of constriction or obstruction of the respiratory system, may enter into systemic circulation but is generally thought to act locally (i.e., topically at the site of constriction or obstruction, or in the local circulation). Epinephrine released from the second portion of the particles, deposited to the alveoli region of the lungs, may act locally (i.e., topically at the site or in the local circulation) but is generally thought to enter the systemic circulation. Applicants believe that the particles' effectiveness in treating a patient in need of epinephrine is due, in part, to the systemic as well as local distribution of epinephrine that is obtained by practicing the present invention. Moreover, it is thought that the quantity of particles deposited will increase with the severity of the obstruction or constriction at the site of obstruction or constriction, thus effectively increasing the local dose where a higher dose of epinephrine is needed. Applicants also believe that by depositing epinephrine containing particles directly into the airway passages and the lungs, respiratory complications of anaphylactic response (e.g., bronchospasm and laryngeal edema) should be more quickly and more effectively treated. By contrast, parenteral (e.g., intraveneous, intramuscular, subcutaneous, and auto-injected) epinephrine administration does not achieve this local delivery component.

Systemic epinephrine concentrations following either subcutaneous, intramuscular, or auto-injector administration have been shown to be quite variable. (See above Simons, et al., 2001). This variability may be an underlying reason for inconsistent clinical response to epinephrine therapy. The coefficient of variation for the maximum epinephrine concentration ($C_{MAX}$) and for the time for maximum epinephrine concentration ($T_{MAX}$) in the patient's blood plasma are substantially lower upon administration of the particles of the present invention than with intramuscularly injected epinephrine.

In one embodiment, the coefficient of variation (CV) for the maximum epinephrine concentration, $C_{MAX}$, in the patient's blood plasma of a dose of epinephrine is lower than for a non-intravenous injection (e.g. subcutaneous, intramuscular, or auto-injector administration) of the same dose of epinephrine. In another embodiment, the coefficient of variation (CV) for the time for maximum epinephrine concentration, $T_{MAX}$, in the patient's blood plasma of a dose of epinephrine is lower than for a non-intravenous injection (e.g. subcutaneous, intramuscular, or auto-injector administration) of the same dose of epinephrine. A lower CV of plasma $T_{MAX}$ and $C_{MAX}$ may translate into an important therapeutic advantage for dry powder epinephrine. Decreased variability, i.e., greater reliability, in peak and time to peak systemic epinephrine concentrations may result in greater consistency in therapeutic response and an improved safety profile.

In one aspect of the instant invention, a method is provided for treating a patient in need of epinephrine, wherein the method comprises administering an effective amount of substantially dry powder particles to the respiratory system of the patient, the particles comprising epinephrine, or a salt thereof, and wherein the resulting epinephrine $C_{MAX}$ in the patient's blood plasma is about 2 to about 3 times greater than epinephrine $C_{MAX}$ in the patient's blood plasma provided by administration of a liquid-based aerosol, such as Medihaler for example. In one embodiment, $C_{MAX}$ of epinephrine in a patient's blood plasma provided by administration of a liquid-based aerosol, such as Medihaler, is determined, for example, using the methods described in Warren, J. B., et al., "Systemic Adsorption of Inhaled Epinephrine," *Clin. Pharmacol. Ther.*, 40(6):673-78 (1986) and also in Dahlof, C., et al., "Systemic Adsorption of Adrenaline after Aerosol, Eyedrop and Subcutaneous Administration to Healthy Volunteers," *Allergy*, 42:215-21 (1987).

The aerodynamic properties of a population of particles can be tailored to generally target deposition sites within the respiratory system. For example, particles can be produced or can be separated so that the particles of a population have a high fine particle fraction, less than 3.4 microns. As is discussed herein, particles having a fine particle fraction of less than 3.4 microns are able to reach the deep lung, or alveoli region of the lung. Alternately, particles can be produced or separated so that a particle population has a low fine particle fraction, less than 3.4 microns. Without being held to any particular theory, Applicants believe that particles having a lower fine particle fraction of less than 3.4 microns are more likely to deposit on surfaces of the respiratory system before the particles reach the deep lung.

In another aspect, the present invention includes a method for treating a patient in need of rescue therapy for anaphylaxis comprising administering particles to the respiratory system of the patient, wherein the particles comprise a therapeutically effective amount of epinephrine, or a salt thereof; and at least one pharmaceutically acceptable excipient, and wherein the particles are delivered to the respiratory system and the epinephrine reaches its site of action within a time sufficiently short to provide said rescue therapy. The method includes administering to the respiratory system of a patient in need of rapid onset or rescue therapy particles comprising an effective amount of epinephrine. The particles are administered to the respiratory system and the epinephrine is released into the patient's blood stream and reaches the epinephrine's site(s) of action in a time interval which is sufficiently short to provide the rescue therapy. As used herein, "rescue therapy" means on demand, rapid delivery of a drug to a patient to help reduce or control disease symptoms.

Rapid release, preferred in the delivery of a rescue therapy medicament, can be obtained for example, by including in the particles materials, such as some phospholipids, characterized by low phase transition temperatures. In another embodiment, a combination of rapid release particles and controlled release particles would allow a rescue therapy coupled with a more sustained release in a single course of therapy.

Rapid delivery of epinephrine to the site(s) of action also is generally preferred. Preferably, the effective amount is delivered on the "first pass" of the blood to the site of action. The "first pass" is the first time the blood carries the drug to and within the target organ or tissue from the point at which the drug passes from the lung to the vascular system. Generally, the medicament is released in the blood stream and delivered to its site(s) of action within a time period which is sufficiently short to provide rescue therapy to the patient being treated. In many cases, the epinephrine can reach the target organ or tissue in less than about 10 minutes. Preferably, the patient's symptoms abate or improve within minutes, for example, within about 5 minutes.

In one embodiment of the invention, the release kinetics of the medicament are substantially similar to the drug's release kinetics achieved via the intravenous route. In another embodiment of the invention, the median $T_{MAX}$ of epinephrine in the blood stream ranges from about 1 to about 10 minutes, preferably the median $T_{MAX}$ of epinephrine in the blood stream is less than about 5 minutes. As used herein, the term "$T_{MAX}$" refers to the timepoint at which blood levels reach a maximum concentration, for example, the time for maximum epinephrine concentration in the patient's blood plasma. In one embodiment, the average time for maximum epinephrine concentration in the patient's blood plasma of a dose of epinephrine is lower than for a non-intravenous injection (e.g., subcutaneous injection, an intramuscular injection, and an auto-injection, for example, EPIPEN®) of the same dose of epinephrine.

Preferably, the patient's symptoms begin to improve within minutes and generally no later than about 15 minutes. In many cases, the average onset of epinephrine effect obtained by using the methods of the invention, for example, the average onset of effect obtained by local action of epinephrine, is at least about 2 times faster than the average onset of epinephrine effect obtained with intramuscular, subcutaneous or auto-injector administration. Average onset of epinephrine effect obtained by using the methods of the invention can range from about 2 to about 5 times faster than that observed with intramuscular, subcutaneous or auto-injector administration. In one example the average onset of epinephrine effect obtained by using the methods of the invention is about 4 to about 5 times faster than that observed with intramuscular, subcutaneous or auto-injector administration.

A method for treating a patient suffering from anaphylaxis is also disclosed, the method comprising: (a) administering an effective amount of substantially dry particles to the respiratory system of the patient, the particles comprising epinephrine, or a salt thereof; (b) monitoring the patient; and (c) administering additional epinephrine to the patient. The effective amount of substantially dry particles are preferably administered via inhalation. Generally, the patient is monitored for abatement of anaphylaxis, e.g., restored ease of breathing, reduced constriction, etc. The additional epinephrine can be administered by intramuscular injection, subcutaneous injection, or auto-injection or can be administered by inhalation of substantially dry particles. In one embodiment, the particles or additional epinephrine are self-administered, i.e., administered by the patient. In another embodiment, the particles or the additional epinephrine is administered outside the direct supervision of a health care professional, for example, a doctor or nurse. For example, the particles or the additional epinephrine may be administered by the patient or by someone other than the patient. In one embodiment, the additional epinephrine is administered to the patient if symptoms of anaphylaxis continue substantially unabated for at least about 5 to about 30 minutes.

The term "substantially abated," as applied to clinical symptoms herein, refers to the reduction of clinical symptoms such that further treatment is typically unnecessary to achieve the desired therapeutic effect(s). The term "substantially unabated," as applied to clinical symptoms herein, refers to the lack of reduction of clinical symptoms such that further treatment is typically necessary to achieve the desired therapeutic effect(s).

In another embodiment, the present invention is directed to a method for treating a patient in need of epinephrine, the method comprising: (a) administering an effective amount of a first mass of substantially dry particles to the respiratory system of the patient, the particles comprising epinephrine, or a salt thereof; and (b) subsequently, administering an effective amount of a second mass of substantially dry particles to the respiratory system of the patient, the particles comprising epinephrine, or a salt thereof. In some aspects, the methods described herein further comprise the administration of at least one more additional effective amount of substantially dry particles to the respiratory system of a patient. For example, a second, third, fourth, fifth, sixth, or seventh amount of substantially dry particles are administered to the respiratory system of a patient as necessary to achieve the desired therapeutic effect(s).

In one embodiment, the patient in need of epinephrine is experiencing anaphylaxis. Preferably, the effective amount of substantially dry particles is administered while the patient experiences symptoms of anaphylaxis, for example, before the symptoms of anaphylaxis have substantially abated. In one aspect, the effective amount(s) of substantially dry particles are administered during a single episode of anaphylaxis. In another aspect, the effective amount of substantially dry particles is administered while the patient experiences at least one of the conditions selected from the group consisting of bronchoconstriction, bronchospasm, airway constriction, and edema. In some embodiments, the effective amount(s) of substantially dry particles are administered within about 72, 48, 36, 24, 12, or about 6 hours of administration of the effective amount of the first mass of substantially dry particles, for example, within about 5, 4, 3, 2, 1, 0.5, or about 0.25 hour(s) of administration of the effective amount of the first mass of substantially dry particles, for example, the effective amount of the second mass of substantially dry particles is administered within about 30 minutes of the administration of the effective amount of the first mass of substantially dry particles. In yet other embodiments, the effective amount(s) of substantially dry particles are administered at least about 0.5, 1, 2, 3, 4, or about 5 minutes after the immediately prior administration of substantially dry particles, for example, the effective amount of the second mass of substantially dry particles are administered at least about 5 minutes after the administration of the effective amount of the first mass of substantially dry particles. In other embodiments, the effective amount(s) of substantially dry particles are administered at least about 10, 15, 20, 25, or about 30 minutes after the immediately prior administration of substantially dry particles.

For example, in one embodiment, the present invention provides a method for treating a patient suffering from anaphylaxis, comprising: (a) administering an effective amount of a first mass of substantially dry particles to the respiratory system of the patient, the particles comprising epinephrine, or a salt thereof; and (b) subsequently, administering an effective amount of a second mass of substantially dry particles to the respiratory system of the patient, the particles comprising epinephrine, or a salt thereof; wherein the first and second masses of substantially dry particles comprise (a) about 11 to about 21 weight percent epinephrine bitartrate; (b) about 62 to about 82 weight percent leucine; and (c) about 7 to about 17 weight percent sodium tartrate. Alternatively, only one of the first and second masses of substantially dry particles comprises (a) about 11 to about 21 weight percent epinephrine bitartrate; (b) about 62 to about 82 weight percent leucine; and (c) about 7 to about 17 weight percent sodium tartrate.

In one embodiment, the effective amount of the first mass of substantially dry particles comprises about 250 to about 750 about 350 to about 650, about 450 to about 550, or about 500 micrograms of epinephrine. In another embodiment, the effective amount of the second mass of substantially dry particles comprises about 250 to about 750 about 350 to about 650, about 450 to about 550, or about 500 micrograms of epinephrine. In yet another embodiment, both the first and second mass of substantially dry particles comprises about 250 to about 750 about 350 to about 650, about 450 to about 550, or about 500 micrograms of epinephrine. For example, in one embodiment, the effective amount of the first mass of substantially dry particles comprises about 500 micrograms of epinephrine, the effective amount of the second mass of substantially dry particles comprises about 500 micrograms of epinephrine, and the effective amount of the second mass of substantially dry particles is administered about 10 to about 20 minutes after administration of the effective amount of the first mass of substantially dry particles.

In some embodiments, either the first or second mass of substantially dry particles further comprises a pharmaceutically acceptable excipient. Alternatively, both the first and second masses of substantially dry particles further comprise a pharmaceutically acceptable excipient. In other embodiments, either or both of the first and second mass of substantially dry particles comprise epinephrine, or a salt thereof, and leucine. In another aspect, either or both of the first and second masses of substantially dry particles further comprise a carboxylic acid, or a salt thereof such as, for example, tartrate, or a salt thereof. For example, either of both of the first or second masses of substantially dry particles comprises (a) about 11 to about 21 weight percent epinephrine bitartrate; (b) about 62 to about 82 weight percent leucine; and (c) about 7 to about 17 weight percent sodium tartrate.

As described herein, administration of particles to the respiratory system are by means such as those known in the art. For example, either or both of the first and second masses of substantially dry particles are delivered via a breath activated inhaler. The invention further comprises delivery of either or both the first and second masses of substantially dry particles in single breath activated steps. In one embodiment, an effective amount of a first mass of substantially dry particles and subsequent effective amounts of substantially dry particles are delivered via separate inhalation devices. For example, the effective amount of the first mass of substantially dry particles and an effective amount of a second mass of substantially dry particles are delivered via separate inhalation devices. Alternatively, the effective amount of the first mass of substantially dry particles and subsequent effective amounts of substantially dry particles are delivered via a single inhalation device. In another embodiment, the mass(es) of substantially dry particles are delivered via a multi-dose inhalation device, such as when either or both of the first and second masses of substantially dry particles are delivered via a multi-dose inhalation device. For example, the effective amount of the first mass of substantially dry particles and the effective amount of the second mass of substantially dry particles are delivered via a multi-dose inhalation device.

In preferred embodiments, administration of the particles of the present invention result in therapeutic effectiveness that approximates or exceeds the duration and/or magnitude of that observed upon administration of other epinephrine formulations such as, for example, formulations for intravenous injection (IV), intramuscular injection (IM), subcutaneous injection, auto-injection (e.g., EPIPEN®), or liquid aerosol inhalation. In one embodiment, dry powder epinephrine is at least as effective for the delivery of epinephrine (e.g., delivery for the treatment of anaphylaxis) as are epinephrine formulations for intravenous injection (IV), intramuscular injection (IM), subcutaneous injection, auto-injection (e.g., EPIPEN®), or liquid aerosol inhalation.

The particles can be fabricated to reduce particle agglomeration and improve flowability of the powder. The spray-dried particles have improved aerosolization properties. Spray-dried particles can be fabricated with features which enhance aerosolization via dry powder inhaler devices and lead to decreased deposition in the mouth, throat and inhaler device. Alternatively, spray-dried particles can be fabricated with features which enhance aerosolization via dry powder inhaler devices and lead to deposition at sites of obstruction or congestion as well as deposition in the alveoli region of the lungs.

The term "effective amount," as used herein, refers to the amount of agent needed to achieve the desired effect or efficacy. The actual effective amounts of drug can vary according to the particular composition formulated, the mode of administration, and the age, weight, condition of the patient, and severity of the symptoms or condition being treated. Dosages for a particular patient can be determined by one of ordinary skill in the art using conventional considerations, for example, by means of an appropriate pharmacological protocol.

The particles of the invention can be employed in compositions suitable for drug delivery via the respiratory system. For example, such compositions can include the particles and a pharmaceutically acceptable carrier for administration to a patient, preferably for administration via inhalation. The particles can be co-delivered with larger carrier particles, not including a therapeutic agent, the latter possessing mass median diameters for example in the range between about 50 and about 100 microns. The particles can be administered alone or in any appropriate pharmaceutically acceptable carrier, for example, a powder, for administration to the respiratory system.

Particles comprising epinephrine are administered to the respiratory system of a patient in need of epinephrine, for example, a patient suffering from anaphylaxis. Administration of particles to the respiratory system can be by means such as those known in the art. For example, particles can be delivered from an inhalation device. In a preferred embodiment, particles are administered as a dry powder via a dry powder inhaler (DPI). Metered-dose-inhalers (MDI), nebulizers or instillation techniques also can be employed.

The methods of the invention also relate to administering to the respiratory system of a subject, particles and/or compositions comprising the particles of the invention, which can be enclosed in a receptacle. As described herein, in certain embodiments, the invention is drawn to methods of delivering the particles of the invention, while in other embodiments, the invention is drawn to methods of delivering respirable compositions comprising the particles of the invention. As used herein, the term "receptacle" includes but is not limited to, for example, a capsule, blister, film covered container well, chamber and other suitable means of storing particles, a powder or a respirable composition in an inhalation device known to those skilled in the art.

In a preferred embodiment, the receptacle is used in a dry powder inhaler. Examples of dry powder inhalers that can be employed in the methods of the invention include but are not limited to, the inhalers disclosed is U.S. Pat. Nos. 4,995,385 and 4,069,819, SPINHALER® (Fisons, Loughborough, U.K.), ROTAHALER® (GlaxoSmithKline, Research Triangle Technology Park, N.C.), FLOWCAPS® (Hovione, Loures, Portugal), INHALATOR® (Boehringer-Ingelheim, Germany), AEROLIZER® (Novartis, Switzerland), DISKHALER® (GlaxoSmithKline, RTP, NC), DISKUS® (GlaxoSmithKline, RTP, NC) and others known to those skilled in the art. In one embodiment, the inhaler employed is described in U.S. patent application Ser. No. 09/835,302, entitled "Inhalation Device and Method," filed on Apr. 16, 2001. The entire contents of this application are incorporated herein by reference.

The invention is also drawn to receptacles which are capsules, for example, capsules designated with a particular capsule size, such as size 2. Suitable capsules can be obtained, for example, from Shionogi (Rockville, Md.). The invention is also drawn to receptacles which are blisters. Blisters can be obtained, for example, from Hueck Foils, (Wall, N.J.). Other receptacles and other volumes thereof suitable for use in the present invention are known to those skilled in the art.

The receptacle encloses or stores particles and/or respirable compositions comprising particles. In one embodiment, the particles and/or respirable compositions comprising particles are in the form of a powder. The receptacle is filled with particles and/or compositions comprising particles. For example, vacuum filling or tamping technologies may be used. Generally, filling the receptacle with powder can be carried out by methods known in the art. In one embodiment of the invention, the particles, powder or respirable composition which is enclosed or stored in a receptacle has a mass of at least about 1.0 mg. Preferably, the mass of the particles or respirable compositions stored or enclosed in the receptacle is at least about 5.0 milligrams or, alternatively, the mass of the particles or respirable compositions stored or enclosed in the receptacle is up to about 10, 20, 25, 30, or 50 milligrams. Generally, the receptacle and the inhalers are used in a temperature range of about 5 to about 35° C. and at about 15 to about 85% relative humidity.

In one embodiment of the invention, the receptacle encloses a mass of particles, especially a mass of highly dispersible particles as described herein. The mass of particles comprises a nominal dose of an epinephrine. As used herein, the phrase "nominal dose" means the total mass of epinephrine which is present in the mass of particles in the receptacle and represents the maximum amount of epinephrine available for administration in a single breath. In some embodiments, the dry powder particles administered to a patient in a single inhalation comprise at least about 50, 100, 150, 200, or 250 micrograms of epinephrine. In other embodiments, the dry powder particles administered to a patient in a single inhalation comprise about 50 micrograms to about 5 milligrams or about 250 micrograms to about 5 milligrams of epinephrine. Preferably, the dry powder particles administered to a patient in a single inhalation comprise about 200 micrograms to about 3 milligrams or about 250 micrograms to about 1 milligram of epinephrine.

Particles and/or respirable compositions comprising particles are stored or enclosed in the receptacles and are administered to the respiratory system of a subject. As used herein, the terms "administration" or "administering" of particles and/or respirable compositions refer to introducing particles to the respiratory system of a subject.

As described herein, in one embodiment, the invention is drawn to a respirable composition comprising carrier particles and epinephrine. Alternatively, the invention is drawn to a method of administering a respirable composition comprising carrier particles and epinephrine. As used herein, the term "carrier particle" refers to particles which may or may not comprise an agent and which aid in the delivery of epinephrine to a subject's respiratory system, for example, by increasing the stability, dispersibility, aerosolization, consistency and/or bulking characteristics of the epinephrine.

It is understood that the particles and/or respirable compositions comprising the particles of the invention which can be administered to the respiratory system of a subject can also optionally include pharmaceutically-acceptable carriers, as are well known in the art. The term "pharmaceutically-acceptable carrier" as used herein, refers to a carrier which can be administered to a patient's respiratory system without any significant adverse toxicological effects. Appropriate pharmaceutically-acceptable carriers, include those typically used for inhalation therapy (e.g., lactose) and include pharmaceutically-acceptable carriers in the form of a liquid (e.g., saline) or a powder (e.g., a particulate powder). In one embodiment, the pharmaceutically-acceptable carrier comprises particles which have a mean diameter ranging from about 50 to about 100 microns, and in particular lactose particles in this size range. It is understood that those of skill in the art can readily determine appropriate pharmaceutically-acceptable carriers for use in administering, accompanying and or co-delivering the particles of the invention.

The particles and/or respirable compositions comprising particles, are preferably administered in a single, breath-activated step. As used herein, the phrases "breath-activated" and "breath-actuated" are used interchangeably. As used herein, "a single, breath-activated step" means that particles are dispersed and inhaled in one step. For example, in single, breath-activated inhalation devices, the energy of the subject's inhalation both disperses particles and draws them into the oral or nasopharyngeal cavity. Suitable inhalers which are single, breath-actuated inhalers that can be employed in the methods of the invention include but are not limited to simple, dry powder inhalers disclosed in U.S. Pat. Nos. 4,995,385 and 4,069,819, SPINHALER® (Fisons, Loughborough, U.K.), ROTAHALER® (GlaxoSmithKline, Research Triangle Technology Park, N.C.), FLOWCAPS® (Hovione, Loures, Portugal), INHALATOR® (Boehringer-Ingelheim, Germany), AEROLIZER® (Novartis, Switzerland), DISKHALER® (GlaxoSmithKline, RTP, NC), DISKUS® (GlaxoSmithKline, RTP, NC) and others, such as known to those skilled in the art. In one embodiment, the inhaler employed is described in U.S. patent application Ser. No. 09/835,302, entitled "Inhalation Device and Method," filed on Apr. 16, 2001. The entire contents of this application are incorporated by reference herein. In another embodiment, a dose of epinephrine is contained in a one-time use (e.g., a disposable) inhaler.

"Single breath" administration can include single, breath-activated administration, but also administration during which the particles, respirable compositions or powders are first dispersed, followed by the inhalation or inspiration of the dispersed particles, respirable compositions or powders. In the latter mode of administration, additional energy other than the energy supplied by the subject's inhalation disperses the particles. An example of a single breath inhaler which employs energy other than the energy generated by the patient's inhalation is the device described in U.S. Pat. No. 5,997,848 issued to Patton, et al., on Dec. 7, 1999, the entire teachings of which are incorporated herein by reference.

In a preferred embodiment, the receptacle enclosing the particles, respirable compositions comprising particles or powder is emptied in a single, breath-activated step. In another preferred embodiment, the receptacle enclosing the particles is emptied in a single inhalation. As used herein, the term "emptied" means that at least about 50% of the particle mass enclosed in the receptacle is emitted from the inhaler during administration of the particles to a subject's respiratory system. This is also called an "emitted dose." In one embodiment, the mass of particles emitted is greater than about 60% of the particle mass enclosed in the receptacle. Alternatively, greater than about 70 or about 80% of the particle mass enclosed in the receptacle is emitted. In another embodiment, about 50 to about 90% of the particle mass enclosed in the receptacle is emitted, such as for example, about 80 to about 90% of the particle mass enclosed in the receptacle.

Delivery to the pulmonary system of particles in a single, breath-actuated step is enhanced by employing particles which are dispersed at relatively low energies such as, for example, at energies typically supplied by a subject's inhalation. Such energies are referred to herein as "low." As used herein, "low energy administration" refers to administration wherein the energy applied to disperse and inhale the particles is in the range typically supplied by a subject during inhaling.

The particles of the instant invention are preferably highly dispersible. As used herein, the phrase "highly dispersible" particles or powders refers to particles or powders which can be dispersed by a RODOS dry powder disperser (or equivalent technique) such that at about 1 bar, particles of the dry powder emit from the RODOS orifice with geometric diameters, as measured by a HELOS or other laser diffraction system, that are less than about 1.5 times the geometric particle size as measured at 4 bar. Highly dispersible powders have a low tendency to agglomerate, aggregate or clump together and/or, if agglomerated, aggregated or clumped together, are easily dispersed or de-agglomerated as they emit from an inhaler and are breathed in by the subject. Typically, the highly dispersible particles suitable in the methods of the invention display very low aggregation compared to standard micronized powders which have similar aerodynamic diameters and which are suitable for delivery to the pulmonary system. Properties that enhance dispersibility include, for example, particle charge, surface roughness, surface chemistry and relatively large geometric diameters. In one embodiment, because the attractive forces between particles of a powder varies (for constant powder mass) inversely with the square of the geometric diameter and the shear force seen by a particle increases with the square of the geometric diameter, the ease of dispersibility of a powder is on the order of the inverse of the geometric diameter raised to the fourth power. The increased particle size diminishes interparticle adhesion forces. (Visser, J., *Powder Technology*, 58:1-10 (1989)). Thus, large particle size, all other things equivalent, increases efficiency of aerosolization to the lungs for particles of low envelope mass density. Increased surface irregularities, and roughness also can enhance particle dispersibility. Surface roughness can be expressed, for example, by rugosity.

Particles suitable for use in the methods of the invention can travel through the upper airways (i.e., the oropharynx and larynx), the lower airways, which include the trachea followed by bifurcations into the bronchi and bronchioli, and through the terminal bronchioli which in turn divide into respiratory bronchioli leading then to the ultimate respiratory zone, the alveoli or the deep lung. In one embodiment of the invention, most of the mass of particles deposit in the deep lung. In another embodiment of the invention, delivery is primarily to the central airways. In another embodiment, delivery is to the upper airways.

The term "dose" of agent refers to that amount that provides therapeutic, prophylactic or diagnostic effect in an administration regimen. A dose may consist of more than one actuation of an inhaler device. In one embodiment, a dose of epinephrine is contained in a one-time use (e.g., a disposable) inhaler. The number of actuations of an inhaler device by a patient are not critical to the invention and may be varied by the physician supervising the administration.

A preferred dosing regimen will elicit an adrenergic response that is similar in magnitude to that observed with injected epinephrine but has a similar or more rapid onset of action and lower variability (e.g., a lower coefficient of variation). Intramuscular epinephrine (300 micrograms) is preferably selected as a reference as it is 1) the most commonly used dose for outpatient treatment for emergency anaphylaxis treatment in Europe and the United States, 2) supported by empiric data, and 3) within current anaphylaxis treatment guidelines.

Models describing the relationship between dose and response provide clinically useful information regarding drug effect and the change of this effect with time. Mathematical models can be constructed to describe the dose-response relationship for key pharmacodynamic (PD) parameters (e.g., blood pressure, serum potassium, pulmonary function, heart rate) following inhaled and injected epinephrine. Modeling approaches include direct (e.g., linear, sigmoid $E_{MAX}$) and indirect response models. For some parameters, the model may be expanded to include concentration-response relationships depending on the level of information available.

Aerosol dosage, formulations and delivery systems may be selected for a particular therapeutic application, as described, for example, in Gonda, I. "Aerosols for delivery of therapeutic and diagnostic agents to the respiratory tract," in *Critical Reviews in Therapeutic Drug Carrier Systems*, 6:273-313 (1990); and in Moren, "Aerosol Dosage Forms and Formulations," in *Aerosols in Medicine, Principles, Diagnosis and Therapy*, Moren, et al., Eds., Esevier, Amsterdam (1985).

Exemplification

Materials used in the following Exemplification and their sources are listed below. Epinephrine Bitartrate, Epinephrine Hydrochloride and Epinephrine Free Base (each USP grade) were obtained from Boehringer Ingelheim (Petersburg, Va.). Leucine, sodium citrate dihydrate, calcium chloride dihydrate, and sodium tartrate dihydrate were acquired from Spectrum Quality Products, Inc. (Gardena, Calif.). 1,2-Dipalmitoyl-sn-glycero-3-phosphocholine (DPPC) (dipalmitoyl phosphatidylcholine) was obtained from Avanti Polar Lipids, Inc. (Alabaster, Ala.).

Methods used in the following Examples are outlined below under appropriate titles.

Aerodynamic Diameter. Mass median aerodynamic diameter (MMAD) was determined using an API AeroDisperser, Model 3230, and Aerosizer, Model 3225 (TSI, Inc., St. Paul, Minn.) using the following procedures. Approximately 0.5 milligrams of sample powder was introduced and dispersed in the AeroDisperser at a shear force of 0.5 psi and then accelerated through a nozzle in the Aerosizer. A direct time-of-flight measurement was made for each particle in the Aerosizer, which was dependent on the inertia of each particle. A time-of-flight distribution was obtained and then translated into a mass-based aerodynamic particle size distribution using a force balance based on Stokes law.

Geometric Diameter. Volumetric median geometric diameter (VMGD) was determined using a laser diffraction technique. The equipment consisted of a HELOS diffractometer and a RODOS disperser (Sympatec, Inc., Princeton, N.J.).

The RODOS disperser applies a shear force to a sample of particles, controlled by the regulator pressure (set at 1.0 bar with orifice ring pressure set at 7 mbar) of the incoming compressed dry powder. Powder sample is dispensed from a microspatule into the RODOS funnel. The dispersed particles travel through a laser beam where the resulting diffracted light pattern produced is collected by a series of detectors. The ensemble diffraction pattern is then translated into a volume-based particle size distribution using the Fraunhofer diffraction model, on the basis that smaller particles diffract light at larger angles.

Fine Particle Fraction. The aerodynamic properties of the powders dispersed from an inhaler device were assessed with a 2-stage MkII Andersen Cascade Impactor (Andersen Instruments, Inc., Smyrna, Ga.). The instrument was run in controlled environmental conditions of 18 to 25° C. and relative humidity (RH) between 20 and 40%. The instrument consists of two stages that separate aerosol particles based on aerodynamic diameter. At each stage, the aerosol stream passes through a set of nozzles and impinges on a corresponding impaction plate. Particles having small enough inertia will continue with the aerosol stream to the next stage, while the remaining particles will impact upon the plate. At each successive stage, the aerosol passes through nozzles at a higher velocity and aerodynamically smaller particles are collected on the plate. After the aerosol passes through the final stage, a filter collects the smallest particles that remain.

This impaction technique allowed for the collection of two separate powder fractions. The capsules were filled with 10 mg of powder and placed inside an inhaler device. The flowrate of dry powder was set to 60 L/min, at which the calibrated cut-off diameters for the two stages are 5.6 microns and 3.4 microns. The instrument was run for 2 seconds. The fractions were collected by placing two filters in the apparatus and determining the amount of powder that impinged on them by gravimetric measurements. Results are reported as the fine particle fraction of less than 5.6 microns (FPF <5.6 microns) and the fine particle fraction of less than 3.4 microns (FPF <3.4 microns).

Alternatively, a 3-stage Andersen Cascade Impactor (ACI) (Andersen Instruments, Inc., Smyrna, Ga.) with screens was assembled and used to determine fine particle fraction. ACI stages 0, 2 and 3 with effective cutoff diameters of 9.0, 4.7, and 3.3 microns (at a flow rate of 28.3±2 L/min) were used in the apparatus. Each stage comprised an impaction plate, a screen, and a jet plate. The screens used were stainless steel 150 micron pore, 5-layer sintered Dynapore laminate (Martin Kurz & Co, Inc., Mineola, N.Y.). Screens were rinsed with methanol, allowed to dry, and then immersed in HPLC grade water and immediately placed on the solid impaction plates of the instrument. A pre-weighted 81 mm glass fiber filter (Anderson Instruments, Inc., Symyrna, Ga.) was used as the instrument's filter medium. Three-stage Andersen Cascade Impactor experiments were conducted at 18 to 25° C. and 20 to 40% RH. The air flow rate through the instrument was calibrated to 28.3±2 L/min. A capsule was filled with powder and placed inside an inhaler device. The capsule was then punctured using the inhaler and placed in a mouthpiece adaptor on the ACI. An air pump was activated for about 4.2 seconds to draw the powder from the capsule. The ACI was dissembled and the glass fiber filter was weighed. Fine particle fraction (FPF) of less than 3.3 microns was determined by dividing the mass of powder deposited on the filter by the total mass of powder loaded into the capsule.

Table A describes the composition and weight percentages of dry powder epinephrine formulations described herein.

TABLE A

| Formulation | Particle Composition | Weight Ratio |
|---|---|---|
| | Composition | |
| I | DPPC:Sodium citrate:Calcium chloride:Epinephrine freebase | 60:20:10:10 |
| II | DPPC:Sodium citrate:Calcium chloride:Epinephrine free base | 65:20:10:5 |
| III | DPPC:Sodium citrate:Calcium chloride:Epinephrine bitartrate | 61:20:10:9 |
| IV | DPPC:Sodium citrate:Calcium chloride:Epinephrine hydrochloride | 58:20:10:12 |
| V | Leucine:Sucrose:Epinephrine free base | 84:15:1 |
| VI | Leucine:Sucrose:Epinephrine bitartrate | 76:15:9 |
| VII | DPPC:Sodium Citrate:Calcium chloride:Epinephrine freebase | 69:20:10:1 |
| IX | Leucine:Epinephrine bitartate | 82:18 |
| X | Leucine:Epinephrine bitartrate | 91:9 |
| XI | Leucine:Epinephrine bitartrate:Sodium tartrate | 72:16:12 |

EXAMPLE 1

This example describes the preparation of particles having the composition of Formulation I, 60 weight percent DPPC, 20 weight percent sodium citrate, 10 weight percent calcium chloride, and 10 weight percent epinephrine freebase.

An aqueous phase was prepared by adding 0.23 g sodium citrate dihydrate, 0.13 g calcium chloride dihydrate, and 0.1 g of epinephrine freebase to 300 mL of water. An organic phase was prepared by adding 0.6 g DPPC to 700 mL of ethanol. The aqueous and organic phases were combined to produce a pre-spray drying solution of 1 liter total volume of 70/30 (v/v) ethanol solution/aqueous solution with a 1 g/L solute concentration. The batch mixed solution was then spray dried. The process gas, heated nitrogen, was introduced at a controlled rate of 38 mm of water (approximately equal to 98 kg/hr) into the top of a Niro Model PSD-1 spray dryer. The spray dryer inlet temperature was 115° C. and the outlet temperature was 45° C. The dew point was controlled and set to −25° C. The solution was atomized with a V24 rotary atomizer spinning at a rate of 20,000 rpm. The particles exited the drying chamber with the process gas and entered a cyclone downstream. The process gas exited from the top of the cyclone and was directed to the exhaust system. The porous particles were recovered from a powder collection vessel at the bottom of the cyclone as dry powder particles.

EXAMPLE 2

This example describes the characterization of two separate batches of Formulation I dry powders, prepared as described in Example 1.

Figure 2:
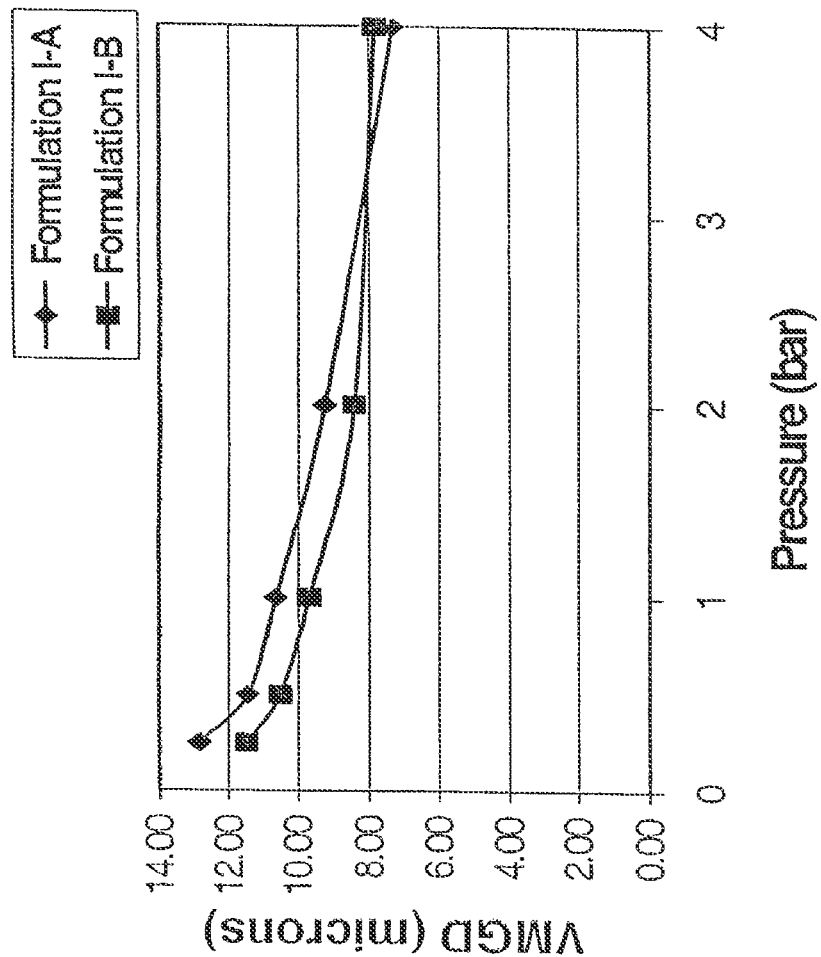
FIG. 2. Volume median geometric diameter (VMGD) curves for two separate batches of epinephrine dry powders (Formulations IA and IB) showing VMGD as a function of pressure.

The physical properties of the particles obtained in two separate batches (Formulation I-A and I-B) are summarized in Table B. The fine particle fraction (FPF) as measured by a 2-stage Andersen Cascade Impactor, an in vitro aerodynamic sizing technique, was on average 56.3% for FPF less than 5.6 microns and 27.1% for FPF less than 3.4 microns. The aerodynamic size was also measured with an Aerosizer. The average value for the mass median aerodynamic diameter (MMAD) was 2.408 microns. The geometric size was determined by laser diffraction and the average value for the volume median geometric diameter (VMGD) at a pressure of 1 bar was 10.2 microns. In addition, the powder displayed relatively flowrate independent behavior as can be seen in FIG. 2 and from the ratio of VMGD measured at 0.5 bar to VMGD measured at 4.0 bar as shown in Table B.

TABLE B

Summary of physical properties of two batches of particles

| Formulation: | I-A | I-B |
|---|---|---|
| FPF less than 5.6 microns | 55.3 | 57.3 |
| FPF less than 3.4 microns | 24.4 | 31.7 |
| VMGD at 1 bar (microns) | 9.7 | 10.7 |
| VMGD ratio at 0.5 bar/4 bar | 1.34 | 1.57 |
| MMAD (microns) | 2.594 | 2.222 |

Chemical Properties. Reverse phase high performance liquid chromatography (RP-HPLC) was utilized to obtain epinephrine content of the powder and an impurity profile. In addition, water content was measured by coulometric Karl-Fischer. Measurements for the two batches of particles are summarized in Table C.

TABLE C

Summary of chemical properties of two batches of particles

| Formulation | % load | % water content | Impurities |
|---|---|---|---|
| I-A | 8.3 | 7.0 | None |
| I-B | 6.2 | 5.6 | None |

All percentages by weight

HPLC Method. The internal standard stock solution was prepared by weighing 200 mg of 3,4-dihydroxybenzylamine and dissolving it in 100 mL of the HPLC mobile phase (2.5% methanol and 97.5% aqueous solution of 10.5 g/L citric acid, 20 mg/L EDTA and 20 mg/L 1-octanesulfonic acid sodium salt monohydrate). The epinephrine stock standard was prepared by weighing 100 mg of epinephrine and dissolving it in 100 mL of the HPLC mobile phase. The epinephrine stock standard was then diluted in methanol to obtain eight dilutions ranging from 1 to 100 mg/mL. Each diluted standard was spiked with equal volume of the stock internal standard.

The samples were prepared by dissolving 5 mg of the dry powder epinephrine samples in 2 mL of methanol. 1 mL of the internal standard stock solution was added and the volume was brought up to 10 mL with methanol.

Alternatively, the epinephrine stock standard was prepared by weighing 100 mg of epinephrine and dissolving it in 100 mL of acidified methanol. The epinephrine stock standard was then diluted in methanol to obtain dilutions ranging from 1 to 100 mg/mL.

Samples were prepared by dissolving 10-20 mg of the dry powder epinephrine samples in 900 mL of methanol and 10 mL of concentrated HCl. The volume was brought up to 1 mL with methanol. A blank was prepared by mixing 990 mL of methanol with 10 mL of concentrated HCl.

The samples were assayed by reverse-phase high performance liquid chromatography (RP-HPLC) using a Waters Symmetry C18 5-mm column (150-mm×4.6-mm ID). The column was kept at 30° C. while the samples were kept at 25° C. in the autosampler. Injection volume was 10 microliters and the samples were passed through the column at a flowrate of 1 mL/min. The mobile phase was stirred continuously during the run and degassed through a Waters in-line degassing system. Detection was performed using an ultraviolet detector set at a wavelength of 254 nm. The concentration of the epinephrine was quantitated against an eight-point standard curve.

Results. The expected load of the powders was 8.6 weight percent epinephrine (based on starting material that was 86% pure, as determined by the RP-HPLC protocol). The actual load was relatively close to this number for powder I-A, but 25% lower for powder I-B (See Table C). This discrepancy may have arisen from the use of the alternative dissolution protocol used to solubilize the powders (see above). The change was made in order to improve the solubility, but it wasn't determined whether 100% recovery was achieved after this change.

Figure 3A:
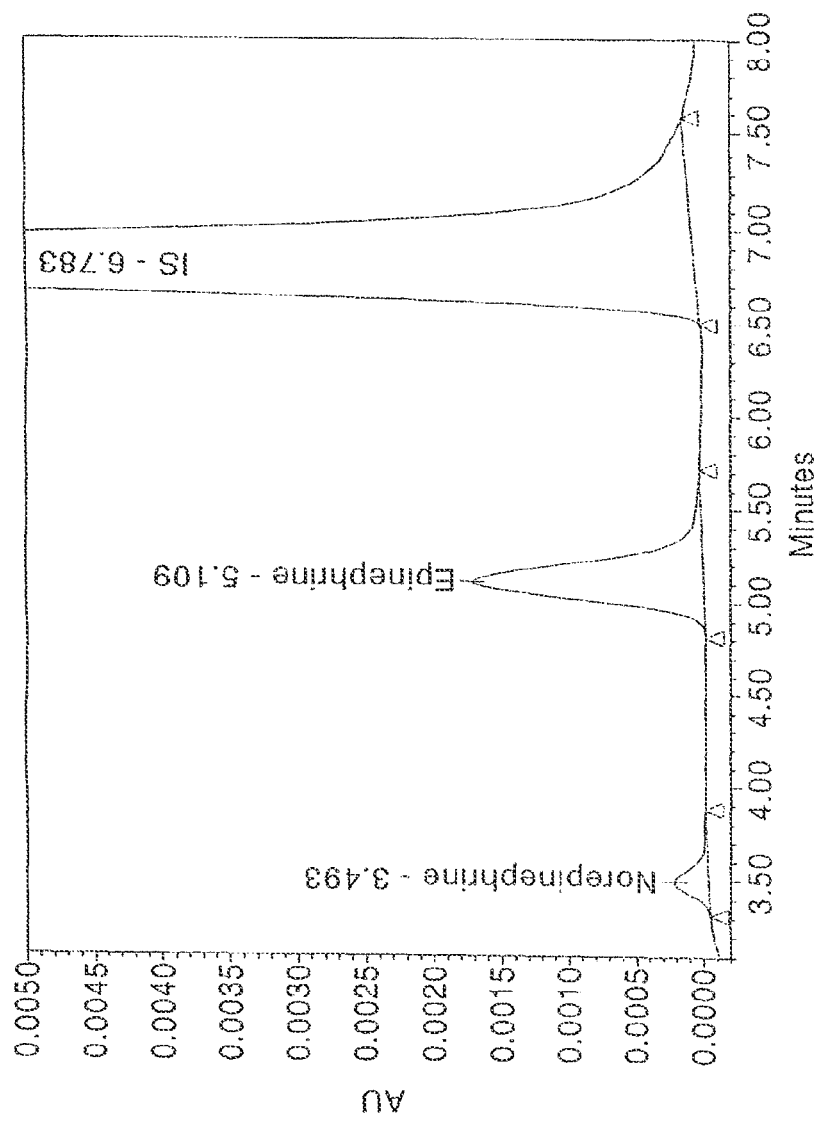
FIGS. 3A, 3B and 3C.
Figure 3B:
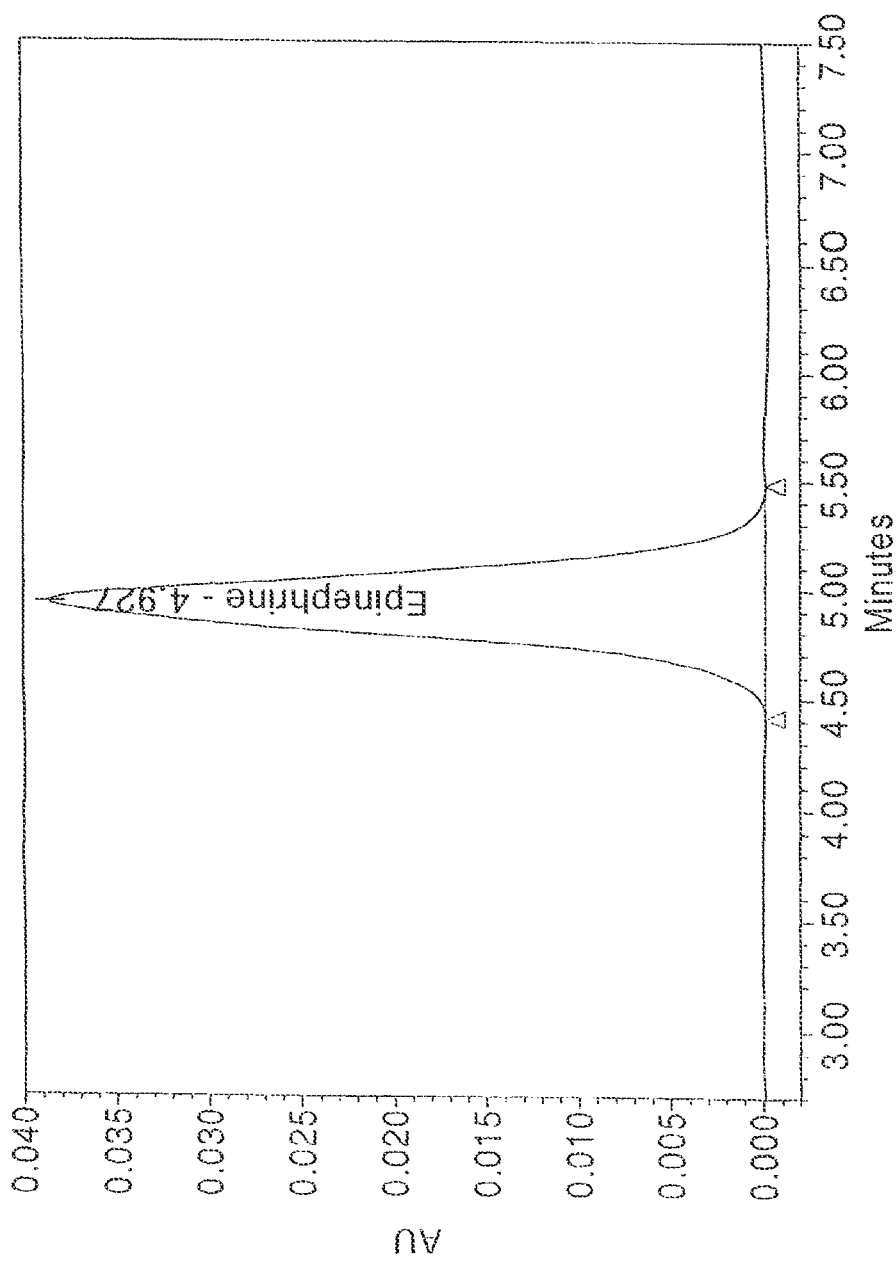
Figure 3C:
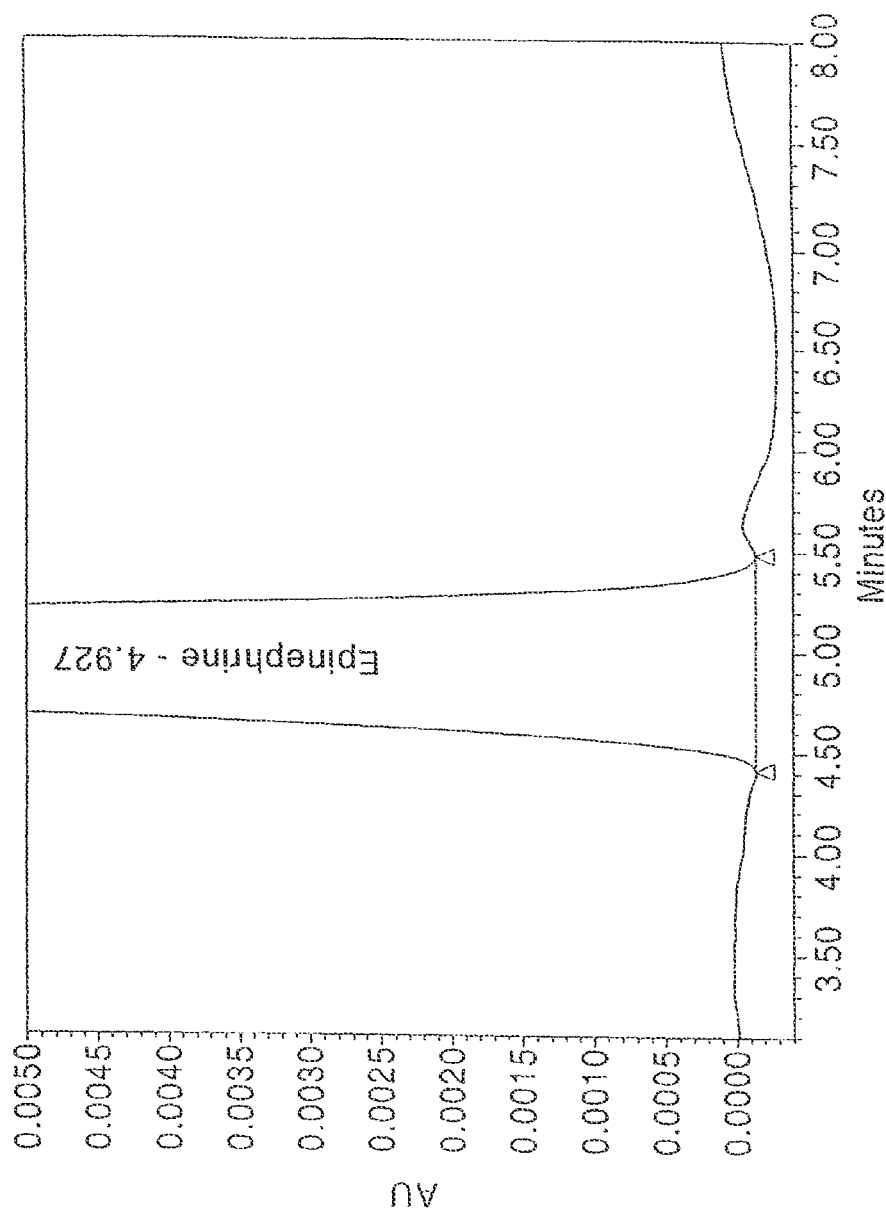

In terms of purity, no impurities were seen in either of the two powders. The chromatograms were undistinguishable from the starting material. The HPLC method was developed to distinguish between catecholamines. This was achieved successfully as can be seen in FIG. 3A, which shows clear separation between epinephrine, norepinephrine and the internal standard 3,4-dihydroxybenzylamine. Furthermore, FIGS. 3B and 3C demonstrate that even at high concentrations of epinephrine, no additional peaks appear in the spectrum.

EXAMPLE 3

This example describes the preparation of particles having the composition of Formulation VII, 69 weight percent DPPC, 20 weight percent sodium citrate, 10 weight percent calcium chloride, and 1 weight percent epinephrine freebase.

228 mg of sodium citrate and 132.5 mg of calcium chloride was added to 294 mL of water. A stock epinephrine solution was prepared by adding 68 microliters of 1N HCl to 6 mL of water, and then adding 10 mg of epinephrine free base. The stock epinephrine solution was then added to the sodium citrate and calcium chloride solution to form an aqueous solution. The pH of the aqueous solution was then adjusted to 5.0 with 1N HCl. An organic solution was prepared by adding 690 mg DPPC to 700 mL of ethanol.

The spray-drying feed solution was prepared by in-line static mixing of the aqueous solution with the organic solution at room temperature, and resulted in a 70/30 (v/v) organic solution/water solution with 1 g/L total solutes. The resulting combined aqueous/organic feed solution was pumped at a controlled rate of 70 mL/min into the top of the spray-drying chamber. Upon entering the spray-drying chamber, the solution was atomized into small droplets of liquid using a V24 rotary atomizer spinning at 20,000 rpm. The process gas, heated nitrogen, was introduced at a controlled rate of 100 kg/hr into the top of the drying chamber of Niro Model PSD-1 spray dryer. The temperature of the inlet was 110° C. and the outlet temp was 47° C. The particles exited the drying chamber with the process gas and entered a cyclone downstream. The process gas exited from the top of the cyclone and was directed to the exhaust system. The porous particles were recovered from a powder collection vessel at the bottom of the cyclone as dry powder particles. The resulting particles had a VMGD of 8.2 microns at 1 bar as determined by RODOS and FPF(<5.6) of 62.1% and FPF(<3.4) of 32% as determined using a two stage ACI. Dry powder epinephrine was filled into size 2 hydroxypropylmethyl cellulose (HPMC) capsules and then packaged.

Particles having the compositions of Formulation II were prepared as described above with weight ratios as shown in Table A.

EXAMPLE 4

This example describes the production of particles having the composition of Formulation III, 61 weight percent DPPC, 20 weight percent sodium citrate, 10 weight percent calcium chloride, and 9 weight percent epinephrine bitartrate.

91 mg of epinephrine bitartrate was added to 300 mL of water to form an aqueous solution. 229 mg of sodium citrate and 132.5 mg of calcium chloride were then added to the aqueous solution. An organic solution was prepared by adding 609 mg of DPPC to 700 mL of ethanol. The aqueous and organic solutions were combined to form a pre-spray drying solution with 1 L total volume of 70/30 (v/v) organic solution/aqueous solution with a 1 g/L total solute concentration. This batch mixed solution was then spray dried. The solution was fed to the spray drying chamber at a rate of 70 mL/min. The solution was atomized with V24 rotary atomizer spinning at 20,000 rpm. Process gas (heated nitrogen) at a rate of 100 kg/hr was introduced to the top of Niro Model PSD-1 spray dryer. The inlet temperature was 120° C. and the outlet temperature was 50° C. The particles exited the drying chamber with the process gas and entered a powder product filter downstream. The product filter separated the porous particles from the process gas stream, including the evaporated solvents. The process gas then exited from the top of the collector and was directed to the exhaust system. The porous particles exited from the bottom of the product filter and were recovered in a powder collection vessel as a dry powder.

The particles were characterized as follows. The VMGD at 1 bar was measured as 12.1 microns. MMAD was measured as 1.6 microns. FPF(<5.6) was 74.8% and FPF(<3.4) was 57.6% as determined using a two stage ACI.

EXAMPLE 5

This example describes the preparation of particles having the composition of Formulation V, 84 weight percent leucine, 15 weight percent sucrose, and 1 weight percent epinephrine free base.

An aqueous solution was prepared by adding 840 mg of leucine and 150 mg of sucrose to 694 mL of water. A stock epinephrine solution was prepared by adding 68 microliters of 1N HCl to 6 mL of water, and then adding 10 mg of epinephrine free base. The approximately 6 mL of stock epinephrine solution was then added to the 694 ml of aqueous solution. The spray drying feed solution was prepared by adding 300 mL of ethanol to the 700 mL of aqueous solution as prepared above, producing a 30/70 (v/v) ethanol solution/aqueous solution with a total solutes concentration of 1 g/L.

The aqueous/organic feed solution was pumped at a controlled rate of 75 mL/min into the top of the spray-drying chamber. Upon entering the spray-drying chamber, the solution was atomized into small droplets of liquid using a V24 rotary atomizer spinning at 24,000 rpm. The process gas, heated nitrogen, was also introduced at a controlled rate of 95 kg/hr into the top of the drying chamber of Model PSD-1 Niro spray dryer. The temperature of the inlet was 190° C. and the outlet temperature was 70° C. The particles exited the drying chamber with the process gas and entered a powder product filter downstream. The product filter separated the porous particles from the process gas stream, including the evaporated solvents. The process gas exited from the top of the collector and was directed to the exhaust system. The porous particles exited from the bottom of the product filter and were recovered in a powder collection vessel as dry powder particles.

The resulting particles had a VMGD of 5.9 microns at 1 bar as determined by RODOS and FPF(<5.6) of 54.5% and FPF (<3.4) of 30% as determined using a two stage ACI. The dry powder was filled into size 2 hydroxypropylmethyl cellulose (HPMC) capsules and then packaged.

Particles having the composition of Formulation VI, 76 weight percent leucine, 15 weight percent sucrose, and 9 weight percent epinephrine bitartrate, also were prepared as described above.

EXAMPLE 6

This example describes the preparation of particles having the composition of Formulation IV, 58 weight percent DPPC, 20 weight percent sodium citrate, 10 weight percent calcium chloride, and 12 weight percent epinephrine hydrochloride.

120 mg of epinephrine hydrochloride was added to 300 mL of water. To this solution, 229 mg of sodium citrate and 132.5 mg of calcium chloride were added. An organic solution was prepared by adding 580 mg of DPPC to 700 mL of ethanol. The aqueous and organic solutions were then combined to produce a pre-spray drying solution of 1 L total volume with 70/30 (v/v) ethanol solution/aqueous solution with a 1 g/L total solute concentration.

This batch mixed pre-spray drying solution was then spray dried in a Niro spray drying chamber. The mixed solution was fed to the top of the spray drying chamber at a rate of 70 mL/min were the solution was atomized with V24 rotary atomizer spinning at 20,000 rpm. The process gas (heated nitrogen) was also introduced to the top of the spray drying chamber at a rate of 100 kg/hr. The inlet temperature was 110° C. and the outlet temperature was 50° C. The particles exited the drying chamber with the process gas and entered a cyclone downstream. The process gas exited from the top of the cyclone and was directed to the exhaust system. Porous particles were recovered from a powder collection vessel at the bottom of the cyclone as dry powder particles.

The resulting particles had a VMGD of 10.1 microns at 1 bar as determined by RODOS and a MMAD of 2.6 microns. The FPF(<5.6) of the particles was 56.2% and the FPF(<3.4) was 25.6%.

EXAMPLE 7

This example describes the preparation of particles having the composition of Formulation IX, 82 weight percent leucine and 18 weight percent epinephrine bitartrate.

300 mL of an aqueous solution containing 0.9 g epinephrine bitartrate and 4.1 g leucine in water (Sterile Water for Irrigation, USP) was prepared. A spray-drying feed solution was prepared by in-line static mixing the aqueous solution with 700 mL of ethanol solution (200 proof, USP), while maintaining both solutions at room temperature. The resulting combined aqueous solution and ethanol solution was pumped at a controlled rate of 65 mL/min into the top of the spray-drying chamber. Upon entering the spray-drying chamber, the solution was atomized into small droplets of liquid using a 2 fluid atomizer at a rate of 23.5 g/min (CPS,PD), 19.5 g/min (RD). The process gas, heated nitrogen, was also introduced at a controlled rate of 100 kg/hr into the top of the drying chamber of Model PSD-1 Niro spray dryer. As the liquid droplets contacted the heated nitrogen, the liquid evaporated and porous particles were formed. The inlet temperature was 107° C. and the outlet temperature was 47° C. The particles exited the drying chamber with the process gas and entered a powder product filter downstream. The product filter separated the porous particles from the process gas stream, including the evaporated solvents. The process gas exited from the top of the collector and was directed to the exhaust system. The porous particles exited from the bottom of the product filter and were recovered in a powder collection vessel as the dry powder particles.

The resulting particles had a VMGD of 6.2 microns at 1 bar as determined by RODOS and an FPF(<5.6) of 54.4% and FPF(<3.4) of 39.1% as determined using a two stage ACI. The dry powder particles had an FPF(<3.3) of 25 to 32% as determined by ACI-3 with wet screens. The dry powder was filled into size 2 hydroxypropylmethyl cellulose (HPMC) capsules and then packaged.

Formulation X was also prepared as described above by adjusting the amounts of leucine and epinephrine to give the desired weight percentages as shown in Table A.

EXAMPLE 8

This example describes the preparation of particles having the composition of Formulation XI, 72 weight percent leucine, 16 weight percent epinephrine bitartrate, and 12 weight percent sodium tartrate.

300 mL of an aqueous solution containing 0.9 g epinephrine bitartrate and 4.1 g leucine in water (Sterile Water for Irrigation, USP) was prepared. The pH of the aqueous solution was adjusted to 4.3 by the addition of sodium tartrate. A spray-drying feed solution was prepared by in-line static mixing the aqueous solution with 700 mL of ethanol solution (200 proof, USP), while maintaining both solutions at room temperature.

The resulting combined aqueous/organic feed solution was pumped at a controlled rate of 65 mL/min into the top of the spray-drying chamber. Upon entering the spray-drying chamber, the solution was atomized into small droplets of liquid using a 2 fluid atomizer at a rate of 23.5 g/min (CPS,PD), 19.5 g/min (RD). The process gas, heated nitrogen, was also introduced at a controlled rate of 100 kg/hr into the top of the drying chamber of Niro spray dryer (Model PSD-1). As the liquid droplets contacted the heated nitrogen, the liquid evaporated and porous particles were formed. The temperature of the inlet was 107° C. and the outlet temperature was 47° C. The particles exited the drying chamber with the process gas and entered a powder product filter downstream. The product filter separated the porous particles from the process gas stream, including the evaporated solvents. The process gas exited from the top of the collector and was directed to the exhaust system. The porous particles exited from the bottom of the product filter and were recovered in a powder collection vessel as dry powder particles. The resulting particles have a VMGD of 5.3 microns at 1 bar as determined by RODOS and an FPF(<3.3) of 25 to 30% using ACI-3 with wet screens. The dry powder was filled into size 2 hydroxypropylmethyl cellulose (HPMC) capsules and then packaged.

EXAMPLE 9

Table D summarizes the physical characteristics of dry powder particles produced as described in Examples 1 and 3 through 8 above.

TABLE D

Physical Characteristics of Dry Powder Particles

| Formulation | VMGD (microns) | MMAD (microns) | FPF(<5.6) (%) | FPF(<3.4) (%) |
|---|---|---|---|---|
| I-A | 9.7 | 2.59 | 55.3 | 24.4 |
| I-B | 10.7 | 2.22 | 57.3 | 31.7 |
| II | 11.0 | 2.4 | 65.3 | 39.7 |
| III | 12.1 | 1.6 | 74.8 | 57.6 |
| IV | 10.1 | 2.6 | 56.2 | 25.6 |
| V | 5.9 | 2.1 | 54.4 | 30 |
| VI | 6.2 | 2.3 | 62.7 | 37.4 |
| VII | 8.2 | 2.9 | 60 | 30 |
| IX | 6.2 | ND | 54.4 | 39.1 |
| X | 12.8 | ND | ND | ND |
| XI | 5.3 | 1.7 | ND | ND |

ND: not determined

EXAMPLE 10

The following example describes experiments to assess the stability of epinephrine in dry powders of the present invention as well as the affect of antioxidants on the stability of epinephrine in dry powders. The 6 antioxidants studied were the following: sodium metabisulfite, disodium EDTA, Vitamin C (ascorbic acid), Vitamin E (alpha tocopherol), cysteamine, and butylated hydroxytoluene (BHT). For each antioxidant different loading levels were chosen as shown in Table E.

TABLE E

Summary of Dry Particle Antioxidant Concentrations.

| Antioxidant | Loading (weight %) | | |
|---|---|---|---|
| Sodium Metabisulfite | 0.6 | 0.9 | 2.0 |
| Vitamin E | 0.1 | 0.3 | 0.9 |
| Vitamin C | 0.6 | 0.9 | 2.0 |
| Cysteamine | 0.03 | 0.1 | 0.3 |
| EDTA | 0.6 | 0.9 | 2.0 |
| BHT | 0.6 | 0.9 | 2.0 |

Solution preparation. For this study, the epinephrine containing particles were spray dried from a solution mixture of 70% organic phase (Pharmco ethyl alcohol) and 30% aqueous phase (McGaw sterile water). The two phases were prepared separately with a total solute concentration of 5 g/L. Leucine, epinephrine bitartrate, and an antioxidant were dissolved consecutively into the aqueous phase. The epinephrine bitartrate was present at 18% of the total solids concentration. The leucine and the antioxidant were present at a combined 82% of the total solids concentration. The two phases were static-mixed immediately prior to being spray dried. Particles containing 82 weight percent leucine and 18 weight percent epinephrine bitartrate (Formulation IX) were prepared as a control.

Solutions containing BHT, Vitamin E and Vitamin C were made using a slightly different procedure as follows. Since BHT and Vitamin E are only soluble in ethanol, the antioxidant was dissolved in ethanol first and then added to an aqueous leucine solution to form a 50/50 (v/v) ethanol/water solution, after which epinephrine was added. Additional ethanol pure solvent was static-mixed with the 50/50 ethanol/water solution to form a 70/30 (v/v) ethanol/water solution. The Vitamin E formulation at the 0.3% and 0.9% loadings were prepared as follows. The Vitamin E at these levels was dissolved in the complete organic phase and static-mixed with the aqueous phase which prevented the Vitamin E from precipitating out of solution. Vitamin C was only dissolved in the aqueous phase at 0.9% and the three other powders containing vitamin C at 0.6, 0.9 and 2.0% was prepared with Vitamin C dissolved in the organic phase. Spray drying of all of the powders was performed as described for Formulation IX using the procedure of Example 7.

Stability conditions and analysis. 50 mg of powder was placed into a 7 mL scintillation vial. The vial was loosely capped and placed inside an oven at 40° C. and approximately 15% relative humidity (RH). Samples were analyzed immediately ($T_0$) and after 1, 2, 4 and 8 weeks of such storage. Controls containing no antioxidants (i.e., Formulation IX) were also placed at 45° C. and 50° C. loosely capped. Chromatographic conditions used to assess epinephrine content are shown in Table F.

TABLE F

Summary of Chromatographic Conditions

| | |
|---|---|
| Column: | Alltech Alltima C18, 4.6 × 250 mm, 5 um |
| Flow Rate: | 1 mL/min |
| Column Temperature: | 30 ± 2° C. |
| Detection: | UV, 280 nm |
| Run Time: | 60 minutes |
| Mobile Phase A: | 0.05% TFA in 20 mM Na2SO4 (aq) |
| Mobile Phase B: | Methanol |
| Dissolving Solvent: | 90% 0.05N HCl 10% Methanol |
| Epinephrine Retention Time: | Approximately 6.2 minutes |

Dry powder epinephrine formulations containing either no antioxidants, or disodium EDTA, sodium metabisulfite, ascorbic acid, vitamin E, cysteamine and BHT at various concentrations were analyzed as a function of time and storage condition. Table G contains the stability data of epinephrine in powders stored at 40° C./15% RH immediately following preparation (i.e., at $T_0$) and after 1, 2, 4 and 8 weeks.

TABLE G

Summary of the total content of epinephrine in powders stored at 40° C./15% RH.

| Antioxidant | Level (%) | Epinephrine Content (%) | | | | |
|---|---|---|---|---|---|---|
| | | Time 0 | 1 Week | 2 Weeks | 4 Weeks | 8 Weeks |
| Control | 0.00 | 99.73 | 99.06 | 98.74 | 97.70 | 95.56 |
| Sodium Metabisulfite | 0.60 | 99.76 | 99.32 | 98.66 | 98.18 | 96.20 |
| Sodium Metabisulfite | 0.90 | 99.74 | 99.42 | 98.92 | 98.58 | 97.02 |
| Sodium Metabisulfite | 2.00 | 99.76 | 99.56 | 99.30 | 99.27 | 98.69 |
| Ascorbic Acid | 0.60 | 99.63 | 98.83 | 98.16 | 97.19 | 93.94 |
| Ascorbic Acid | 0.90 | 99.74 | 99.13 | 98.49 | 97.93 | 95.37 |
| Ascorbic Acid | 0.9% to H$_2$O | 99.70 | 98.86 | 98.18 | 97.11 | 93.65 |
| Ascorbic Acid | 2.00 | 99.73 | 98.99 | 98.49 | 97.78 | 94.74 |
| EDTA | 0.60 | 99.75 | 99.17 | 98.78 | 98.05 | 96.21 |
| EDTA | 0.90 | 99.77 | 99.20 | 99.04 | 98.48 | 96.90 |
| EDTA | 2.00 | 99.77 | 99.43 | 99.24 | 98.92 | 98.19 |
| Cysteamine | 0.03 | 99.77 | 98.73 | 98.33 | 96.79 | 93.94 |
| Cysteamine | 0.10 | 99.76 | 98.67 | 98.28 | 96.85 | 94.19 |
| Cysteamine | 0.30 | 99.74 | 98.82 | 98.17 | 96.74 | 93.71 |
| BHT | 0.60 | 99.73 | 98.95 | 98.56 | 97.37 | 94.78 |
| BHT | 0.90 | 99.76 | 99.08 | 98.71 | 97.52 | 95.15 |
| BHT | 2.00 | 99.73 | 99.08 | 98.80 | 97.80 | 95.42 |
| Vitamin E | 0.10 | 99.66 | 99.00 | 98.58 | 97.16 | 94.49 |
| Vitamin E | 0.30 | 99.73 | 99.04 | 98.64 | 97.40 | 94.84 |
| Vitamin E | 0.90 | 99.74 | 99.12 | 98.62 | 97.46 | 94.83 |
| Vitamin E | 0.30 | 99.63 | 99.13 | 98.76 | 97.94 | 96.32 |

The data demonstrate good spray drying reproducibility with epinephrine levels around 99.72% with a very low deviation at TO for all the powders tested.

Sodium metabisulfite and EDTA provided good protection against degradation of epinephrine at 40° C. and 15% RH; they both provided added stability when compared to the control containing no antioxidants. As the level of sodium metabisulfite increased, the level of protection at this accelerated condition increased. The same trend was noticed for EDTA containing powders. Vitamin E at 0.3% loading, when added to the ethanol phase during spray drying, also showed favorable results.

Disodium EDTA had an increased effect on total impurities as the levels were increased from 0.6% to 2%. Sodium Metabisulfite had an increased effect on total impurities as the levels are increased from 0.6% to 2%. Ascorbic acid, BHT, and cysteamine generally were not effective antioxidants for this epinephrine formulation at this accelerated condition. Vitamin E provided the favorable protection when it was added to the ethanol phase at a concentration of 0.3%.

EXAMPLE 11

Particles containing either sodium metabisulfite, EDTA, or Vitamin E were spray dried at a variety of levels with the total antioxidant content of the formulation never exceeding 2%. For this study, dry powder epinephrine formulations based on Formulation XI, as is described in Table A, were spray dried from a mixture of 70% organic phase (Pharmco ethyl alcohol) and 30% aqueous phase (McGaw sterile water) as described in Example 8. The two phases were prepared separately with a total solids concentration of 5 g/L prior to the pH adjustment step. Leucine, the antioxidants, and epinephrine bitartrate were dissolved consecutively into the aqueous phase. Since Vitamin E is not soluble in water, it was dissolved in the organic phase. Sodium tartrate was added to the aqueous phase to raise the pH of the mixture to 4.30.

For each antioxidant different loading levels were chosen. The final composition of each powder is reported in Table H. Two controls (i.e., ID A and ID N as shown in Table H) were made which contained no antioxidants. The total content of antioxidants in each formulation did not exceed 2% by weight.

TABLE H

Composition of Antioxidant Containing Dry Powders (% w/w).

| ID | Antioxidants: Sodium Metabisulfite | EDTA | Vitamin E | Epinephrine Bitartrate | Leucine | Sodium Tartrate |
|---|---|---|---|---|---|---|
| A | 0 | 0 | 0 | 15.7 | 71.4 | 12.9 |
| B | 2 | 0 | 0 | 15.0 | 68.4 | 14.6 |
| C | 0 | 0 | 2 | 15.3 | 69.7 | 13.0 |
| D | 0 | 1 | 1 | 15.3 | 69.7 | 13.0 |
| E | 2 | 0 | 0 | 15.2 | 69.4 | 13.3 |
| F | 1 | 0 | 1 | 15.2 | 69.2 | 13.7 |
| G | 1.33 | 0.33 | 0.33 | 15.1 | 68.9 | 14.0 |
| H | 0 | 2 | 0 | 15.3 | 69.7 | 13.0 |
| I | 1 | 1 | 0 | 15.2 | 69.4 | 13.3 |
| J | 0.67 | 0.67 | 0.67 | 15.2 | 69.2 | 13.7 |
| K | 0 | 2 | 0 | 15.3 | 69.7 | 13.0 |
| L | 1 | 1 | 0 | 15.2 | 69.4 | 13.3 |
| M | 0.33 | 1.33 | 0.33 | 15.2 | 69.4 | 13.3 |
| N | 0 | 0 | 0 | 15.7 | 71.7 | 12.6 |
| O | 0 | 0 | 2 | 15.4 | 70.2 | 12.3 |
| P | 0.33 | 0.33 | 1.33 | 15.4 | 70.2 | 12.3 |

Twenty milligrams of powder was placed into a 4 mL amber scintillation vial at 15% RH. The vial was tightly capped with a Teflon cap and placed inside an oven at 40° C. or 50° C. The powder sample was stored at approximately 15% RH.

Samples were analyzed immediately ($T_0$) and after 0.5, 1, 1.5, 2, 4 weeks at 50° C. and after 1, 2, 3, 4 and 8 weeks at 40° C. At each timepoint, two individually vialed samples were removed from the oven and analyzed (i.e., n=2). HPLC analysis of epinephrine integrity was performed as described above.

Dry powders containing either no antioxidants, disodium EDTA, sodium metabisulfite, Vitamin E, or a combination thereof, at various concentrations as shown in Table H were analyzed as a function of time and storage condition. Table I contains stability data for powders stored at 50° C./15% RH immediately following preparations ($T_0$) and after 0.5, 1, 1.5, 2, and 4 weeks. Table J contains the stability data for powders stored at 40° C./15% RH immediately following preparations ($T_0$) and after 1, 2, 3, 4 and 8 weeks.

TABLE I

Summary of the total content of epinephrine in powders stored at 50° C./15% RH.

| | Percent Epinephrine | | | | | | | | | | | |
|---|---|---|---|---|---|---|---|---|---|---|---|---|
| | Time 0 | | 0.5 Weeks | | 1 Week | | 1.5 Weeks | | 2 Weeks | | 4 Weeks | |
| ID | n = 1 | n = 2 | n = 1 | n = 2 | n = 1 | n = 2 | n = 1 | n = 2 | n = 1 | n = 2 | n = 1 | n = 2 |
| A | 99.72 | 99.78 | 99.39 | 99.48 | 98.98 | 99.01 | 98.99 | 99.02 | 98.60 | 98.64 | 96.52 | 97.34 |
| B | 99.80 | 99.78 | 99.56 | 99.56 | 99.35 | 99.29 | 99.31 | 99.46 | 99.11 | 99.09 | 98.85 | 98.75 |
| C | 99.73 | 99.80 | 99.59 | 99.60 | 99.33 | 99.35 | 99.38 | 99.31 | 98.91 | 99.07 | 97.21 | 97.34 |
| D | 99.78 | 99.81 | 99.60 | 99.55 | 99.29 | 99.36 | 99.28 | 99.32 | 99.02 | 99.09 | 97.66 | 97.26 |
| E | 99.80 | 99.77 | 99.62 | 99.64 | 99.44 | 99.43 | 99.49 | 99.46 | 99.27 | 99.30 | 98.45 | 98.25 |
| F | 99.80 | 99.78 | 99.43 | 99.49 | 98.37 | 98.9 | 98.57 | 98.55 | 98.90 | 99.51 | 94.61 | 93.98 |
| G | 99.80 | 99.81 | 99.50 | 99.55 | 99.26 | 99.35 | 99.09 | 99.39 | 99.59 | 99.60 | 98.48 | 98.24 |
| H | 99.82 | 99.80 | 99.54 | 99.50 | 99.03 | 99.11 | 99.16 | 99.23 | 99.43 | 99.48 | 98.07 | 99.07 |
| I | 99.77 | 99.78 | 99.59 | 99.60 | 99.37 | 99.28 | 99.55 | 99.54 | 98.97 | 99.14 | 99.07 | 98.85 |
| J | 99.78 | 99.77 | 99.63 | 99.65 | 99.43 | 99.63 | 99.46 | 99.51 | 99.30 | 99.54 | 98.21 | 98.32 |
| K | 99.79 | 99.81 | 99.49 | 99.46 | 99.22 | 99.32 | 99.32 | 99.28 | 99.38 | 99.22 | 97.82 | 97.83 |
| L | 99.79 | 99.80 | 99.49 | 99.55 | 99.19 | 99.28 | 99.23 | 99.43 | 99.58 | 99.56 | 97.97 | 98.59 |
| M | 99.79 | 99.82 | 99.74 | 99.77 | 99.68 | 99.68 | 99.70 | 99.67 | 99.61 | 99.64 | 99.16 | 99.22 |
| N | 99.81 | 99.80 | 99.40 | 99.47 | 99.09 | 99.12 | 99.06 | 99.13 | 98.78 | 99.10 | 97.16 | 97.74 |
| O | 99.81 | 99.80 | 99.64 | 99.51 | 99.21 | 99.22 | 99.20 | 99.33 | 98.85 | 99.11 | 96.93 | 95.74 |
| P | 99.77 | 99.79 | 99.64 | 99.61 | 99.47 | 99.48 | 99.56 | 99.52 | 99.36 | 99.28 | 99.04 | 98.08 |

TABLE J

Summary of the total content of epinephrine in powders stored at 40° C./15% RH.

| | Percent Epinephrine | | | | | | | | | | | |
|---|---|---|---|---|---|---|---|---|---|---|---|---|
| | Time 0 | | 0.5 Weeks | | 1 Week | | 1.5 Weeks | | 2 Weeks | | 4 Weeks | |
| ID | n = 1 | n = 2 | n = 1 | n = 2 | n = 1 | n = 2 | n = 1 | n = 2 | n = 1 | n = 2 | n = 1 | n = 2 |
| A | 99.72 | 99.78 | 99.62 | 99.58 | 99.35 | 99.32 | 99.12 | 99.06 | 98.85 | 98.88 | 98.10 | 98.03 |
| B | 99.80 | 99.78 | 99.74 | 99.74 | 99.60 | 99.55 | 99.43 | 99.62 | 99.42 | 99.33 | 98.95 | 99.25 |
| C | 99.73 | 99.80 | 99.81 | 99.81 | 99.71 | 99.74 | 99.65 | 99.34 | 99.15 | 99.27 | 98.65 | 98.65 |
| D | 99.78 | 99.81 | 99.77 | 99.74 | 99.69 | 99.69 | 99.33 | 99.39 | 99.22 | 99.17 | 98.77 | 98.60 |
| E | 99.80 | 99.77 | 99.81 | 99.80 | 99.73 | 99.72 | 99.70 | 99.68 | 99.33 | 99.48 | 99.02 | 99.04 |
| F | 99.80 | 99.78 | 99.52 | 99.48 | 99.64 | 99.37 | 99.00 | 99.71 | 98.41 | 98.74 | 97.75 | 97.79 |
| G | 99.80 | 99.81 | 99.79 | 99.75 | 99.63 | 99.61 | 99.34 | 99.72 | 99.36 | 99.18 | 99.18 | 99.47 |
| H | 99.82 | 99.80 | 99.68 | 99.71 | 99.52 | 99.49 | 99.68 | 99.42 | 98.79 | 99.39 | 98.91 | 99.03 |
| I | 99.77 | 99.78 | 99.75 | 99.80 | 99.75 | 99.72 | 99.64 | 99.62 | 99.21 | 99.56 | 99.31 | 98.77 |
| J | 99.78 | 99.77 | 99.82 | 99.79 | 99.78 | 99.8 | 99.73 | 99.72 | 99.53 | 99.51 | 99.53 | 99.11 |
| K | 99.79 | 99.81 | 99.73 | 99.68 | 99.62 | 99.62 | 99.65 | 99.29 | 99.21 | 99.22 | 98.91 | 98.61 |
| L | 99.79 | 99.80 | 99.70 | 99.73 | 99.64 | 99.7 | 99.65 | 99.43 | 99.07 | 99.29 | 98.44 | 99.33 |
| M | 99.79 | 99.82 | 99.82 | 99.82 | 99.79 | 99.8 | 99.73 | 99.74 | 99.71 | 99.69 | 99.44 | 99.47 |
| N | 99.81 | 99.80 | 99.71 | 99.71 | 99.56 | 99.56 | 99.24 | 99.21 | 99 | 99.18 | 98.49 | 98.67 |
| O | 99.81 | 99.80 | 99.74 | 99.73 | 99.47 | 99.45 | 99.34 | 99.42 | 99.24 | 99.44 | 98.56 | 98.77 |
| P | 99.77 | 99.79 | 99.73 | 99.76 | 99.69 | 99.76 | 99.63 | 99.66 | 99.53 | 99.47 | 99.08 | 99.10 |

The data demonstrates good spray drying reproducibility with epinephrine levels around 99.79% with a very low deviation from replicate samples at $T_0$ for all the powders tested. As seen in Table I, all antioxidants used in combination provided good protection against degradation of epinephrine at 50° C. and 15% RH. When used together, sodium metabisulfite, EDTA, and Vitamin E provided added stability when compared to a control containing no antioxidants. The combination of 0.34% sodium metabisulfite, 1.34% EDTA, and 0.34% Vitamin E provided the best overall protection. This combination showed epinephrine levels of 99.19% after 4 weeks at 50° C. and 15% RH. The two controls showed epinephrine levels of 96.93% and 97.45%. Therefore, this combination afforded about 2% greater stability after 4 weeks at 50° C. and 15% RH. A strong dependence on EDTA can also be seen from the data at 50° C. and 15% RH; formulations containing no EDTA generally performed worse than those containing some EDTA in combination. Particle formulations containing only EDTA as an antioxidant showed low impurities when stored at 50° C. and 15% RH.

As seen in Table J, all antioxidants used in combination provided good protection against degradation of epinephrine at 40° C. and 15% RH. When used together, sodium metabisulfite, EDTA, and vitamin E provide added stability when compared to a control containing no antioxidants. An optimum combination of 0.34% sodium metabisulfite, 1.34% EDTA, and 0.34% Vitamin E provided the best protection overall. This combination showed epinephrine levels of 99.45% after 8 weeks at 40° C. and 15% RH. The two controls showed epinephrine levels of 98.12% and 98.58%. Therefore, this optimum combination afforded about 1% greater stability at this condition after 8 weeks at 40° C. and 15% RH. A strong dependence on EDTA can also be seen from the data at 40° C. and 15% RH. Formulations containing no EDTA generally performed worse than those containing some EDTA in combination. Also, formulations containing only EDTA as an antioxidant showed low impurities at this condition.

Using this data it was possible to model the space surrounding these antioxidant combinations in order to predict the combination of antioxidants that would provide the best stability. Using the data from 50° C. and 15% RH at 4 weeks, a statistically significant model was found. From this model a combination of 0.65% Na metabisulfite, 0.92% EDTA, and 0.43% Vitamin E was predicted to have 99.23% purity after 4 weeks at 50° C. and 15% RH.

EXAMPLE 12

This example describes the pharmacokinetic (PK) and pharmacodynamic (PD) profile following pulmonary administration of a dry powder containing epinephrine compared to intramuscularly injected epinephrine. Rats were single-dosed with a dry powder having the composition of Formulation I and prepared as in Example 1 (nominal dose=25.8 mg), dosed using an intratracheal insufflation technique, insufflated with room air as a placebo control, or injected with a solution of epinephrine given intramuscularly (25.8 mg/ml; nominal dose=12.9 mg). Blood samples were taken from the rats via jugular catheters at time points 0, 2.5, 5, 10, and 20 minutes following dosing. Measurements of heart rate were also made at the same time points.

Animals. Male Sprague Dawley rats were obtained from Taconic Farms (Germantown, N.Y.). At the time of use, the animals weighed between 450 and 550 grams. The animals were in good health upon arrival and remained so until use; no clinical signs of illness were observed at any time. They were housed two per cage while on study in accordance to NIH guidelines in standard plastic shoebox cages. The animals were allowed to acclimate to their surroundings for at least one-week prior to use. The light/dark cycle was 12/12 hours. The temperature in the animal room was ambient room temperature of approximately 19° C. (66° F.). The ambient humidity in the animal rooms was approximately 23% on the day of the study. The animals were allowed free access to food and water. The food was Lab Diet-Rodent Chow #5010 (PMI Nutrition International, Inc., Brentwood, Mo.). The water was from a clean tap source.

Dose Administration. The powder was delivered to the lungs of rats by an insufflation technique. The insufflator device was from PennCentury (Philadelphia, Pa.). The delivery tube of the insufflator was inserted intratracheally through the mouth until the tip of the tube was about a centimeter from the carina (first bifurcation). The amount of epinephrine delivered to the lungs was approximately 300 micrograms irrespective of the animal's body weight. The volume of dry powder used to deliver the powder from the sample chamber was 3 mL, which was achieved from a charged syringe. The syringe was recharged and discharged two more times for a total of three discharges per powder dose in order to decrease or eliminate powder residues in the sample chamber.

Study Design. The jugular vein of animals used in pharmacokinetics studies was catheterized with PE90 on the day before the dosing and sampling was performed. A total of six animals were used in this study. For anesthesia (catheter placement and powder dosing), a mixture of ketamine (25 mg), xylazine (3 mg), and acepromazine (0.2 mg) was injected intraperitoneally (IP) into each animal. The rats were placed on a heating pad after catheter placement to recover. After powder dosing, the rats were placed back in their respective cages. Identification numbers assigned to the rats were written on their tails as well as on the cage cards. Blood was taken and heart rate was measured using a pulse oximeter attached to the right hind limb of the rats at time 0, 2.5, 5.0, 10.0, and 20.0 minutes. The blood samples were collected by syringe from the jugular vein catheter. The blood was carefully ejected into EDTA coated tubes, mixed and then centrifuged for 5 minutes at 14,000 g to separate the plasma from the cells. Plasma was placed into clean microfuge tubes and stored refrigerated until received at the laboratory. Samples were stored at 2-8° C. if analysis was performed within 24 hours, or at −80° C. if analysis would occur later than 24 hours.

Plasma Epinephrine Extraction Method. Epinephrine was extracted from the plasma using the ESA Plasma Catecholamine Analysis Kit. First, an epinephrine standard solution was prepared by diluting the provided epinephrine stock solution to the desired concentration (4, 8, 20, 40, and 100 ng/mL). Second, an internal standard spiking solution of DHBA was prepared by diluting the provided DHBA stock solution to a concentration of 10 ng/mL. 50 mL of the internal standard solution were then added to all the extraction tubes. 200 mL of the plasma sample or the epinephrine standard were also added into the extraction tubes. The tubes were capped, mixed by inversion, and rocked on a mechanical rocker for 10 minutes. The caps were taken off and washed with the provided Wash Solution in order not to lose any material from the tubes. The bottom cap was then removed and the tubes were placed on a vacuum extraction manifold. The vacuum was turned on and all fluid was sucked out of the tubes. The tubes were filled with the Wash Solution and the vacuum was turned back on to remove all fluid. The tubes were filled with the Wash Solution again and the above step was repeated. The remainder of the fluid was forced out of the tubes by applying positive pressure to the tops with a modified extraction bulb. The tubes were capped again at the bottom and 200 _L of the Eluting Solution were added. The tubes were capped at the top and vortexed for 10 minutes at speed of 3. Both caps were removed and an eluent was collected by applying positive pressure to the tops of the tubes with the modified extraction bulb. The eluent was then injected directly onto the column.

HPLC Method for Extracted Serum Samples. The samples were assayed by high performance liquid chromatography (HPLC) using a Waters Symmetry C18 5-_m column (150-mm×4.6-mm ID). The column and the samples were kept at room temperature during the run. The mobile phase was prepared from 4% methanol and 96% aqueous solution (10.5 g/L citric acid, 20 mg/L EDTA, 20 mg/L 1-octanesulfonic acid sodium salt monohydrate). Injection volume was 50 microliters and the samples were passed through the column at a flowrate of 1 mL/min. Detection was performed using an electrochemical detector. The voltage was set to 350 mV across the conditioning cell, to 50 mV across the first analytical electrode, and to −300 mV across the second analytical electrode.

Calculation of Epinephrine Concentration. The epinephrine standards were used to construct a standard curve. After the extraction procedure, the concentrations of the standards were 1, 2, 5, 10, and 25 ng/mL (calculated based on the change in volume during the extraction procedure). An internal standard having the concentration of 2.5 ng/mL was also present in the solution. The standards were run on the HPLC column and the areas of the epinephrine and internal standard peaks were determined. The ratio of the epinephrine peak area and the internal standard peak area was calculated and plotted against the known concentration of the epinephrine standards. A straight line was fitted through the data. The standard curve was used to calculate the concentration of epinephrine in the samples based on the ratio of the peak areas of the epinephrine peak and the internal standard peak. The percent recovery of the internal standards was also calculated from the peak area of the internal standard in the sample as compared to the peak area of the internal standard when injected in buffer.

Figure 4A:
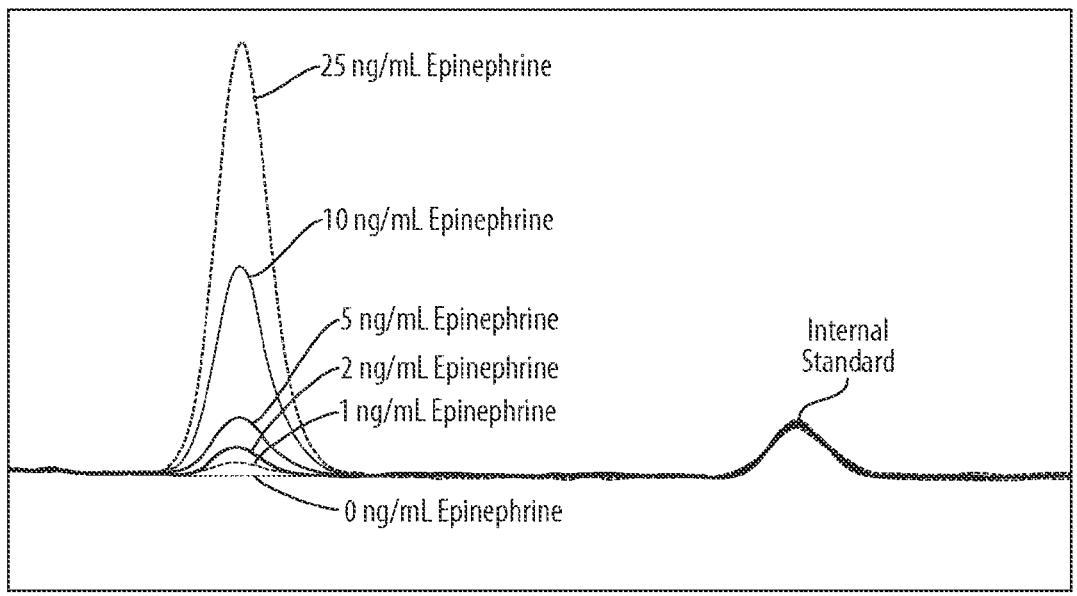
FIGS. 4A and 4B.
Figure 4B:
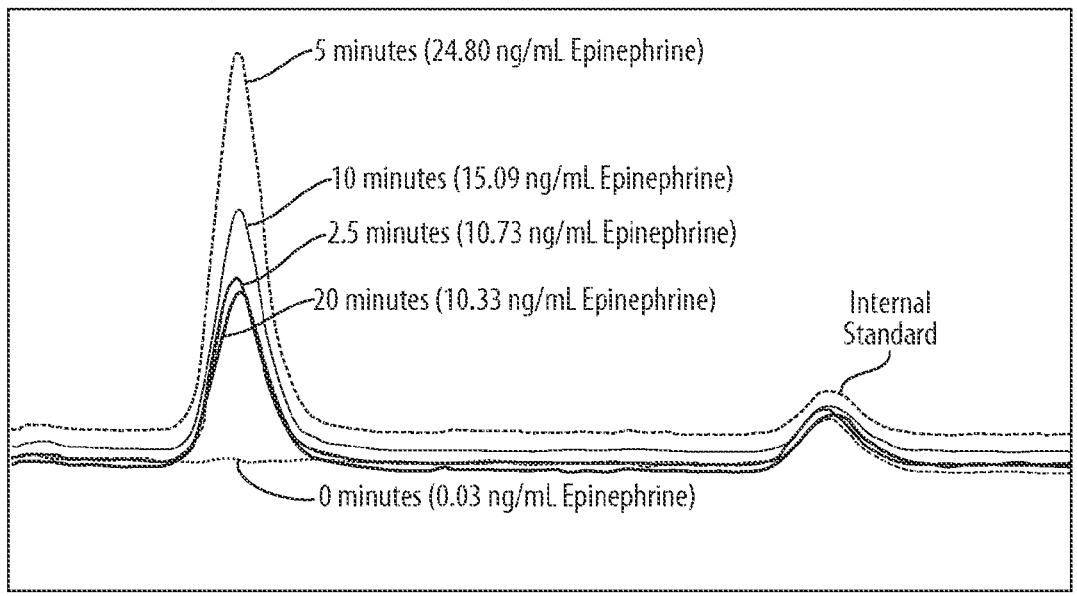

Pharmacokinetics. The blood obtained from the animals was separated into plasma. Epinephrine was extracted from the plasma using a ESA Plasma Catecholamine Analysis Kit. The concentration of epinephrine was then determined by high performance liquid chromatography (HPLC). The method worked very well as can be seen from the clean sample chromatograms in FIG. 4.

Figure 5:
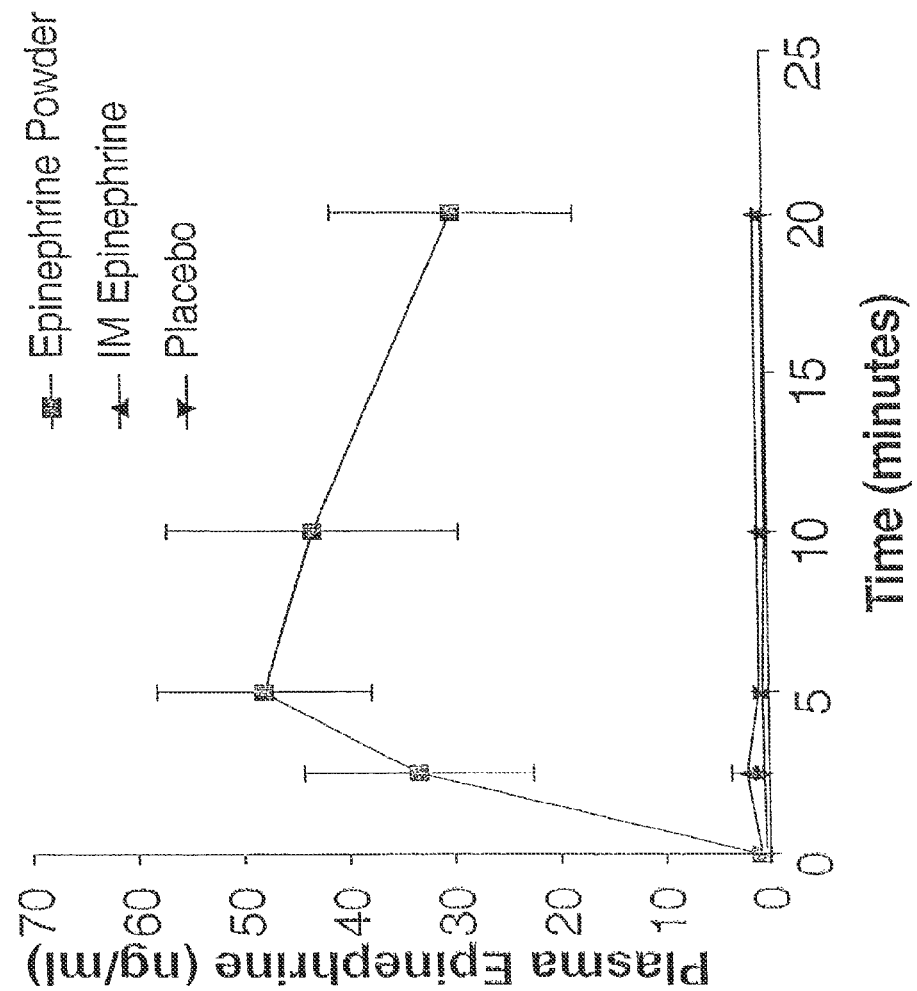
FIG. 5. Levels of plasma epinephrine (ng/mL) following placebo treatment, pulmonary insufflation of the dry powder epinephrine powder, and intramuscular injection of epinephrine as a function of time in minutes.

FIG. 5 shows the plasma epinephrine data from all treatment groups. Plasma epinephrine concentrations increased rapidly after pulmonary administration of powder, with a $T_{MAX}$ of 5.0 minutes and a $C_{MAX}$ of 48.01 ng/mL. Epinephrine levels were headed back to baseline by 20 minutes following dosing. Plasma epinephrine levels were very low and not significantly different from room air controls in animals injected intramuscularly (IM) with epinephrine in solution. In comparison with literature on inhalation of liquid aerosol epinephrine, the bioavailability of epinephrine is higher with a dry powder formulation. Humans dosed with 20 puffs of aerosol adrenaline at 0.15 milligrams/puff (0.06 mg/kg) achieved peak plasma concentrations of 2.5 ng/mL. Mellem, H., et al., "Faster and More Reliable Absorption of Adrenaline by Aerosol Inhalation then by Subcutaneous Injection," *Br. J. Clin. Pharmacol.*, 6:677-81 (1991). In contrast, insufflation of dry powder epinephrine (1.0 mg/kg) resulted in peak plasma concentrations of 48 ng/mL. Taking into account the variations in dosing methods (10% deposition by inhalation, 50% by insufflation), the dry powder formulation appears to have 4-5 times greater bioavailability than a liquid aerosol. The lack of significant plasma epinephrine measurements in intramuscularly injected animals was surprising based on human data. However, human injection is typically subcutaneous versus intramuscular injection in the rat. The rat intramuscular injection may have significantly altered the rate of uptake so that by twenty minutes, significant intravenous levels of epinephrine had not yet been achieved. This hypothesis is evidenced by the late rise in heart rate observed in IM-dosed animals described below.

Figure 6:
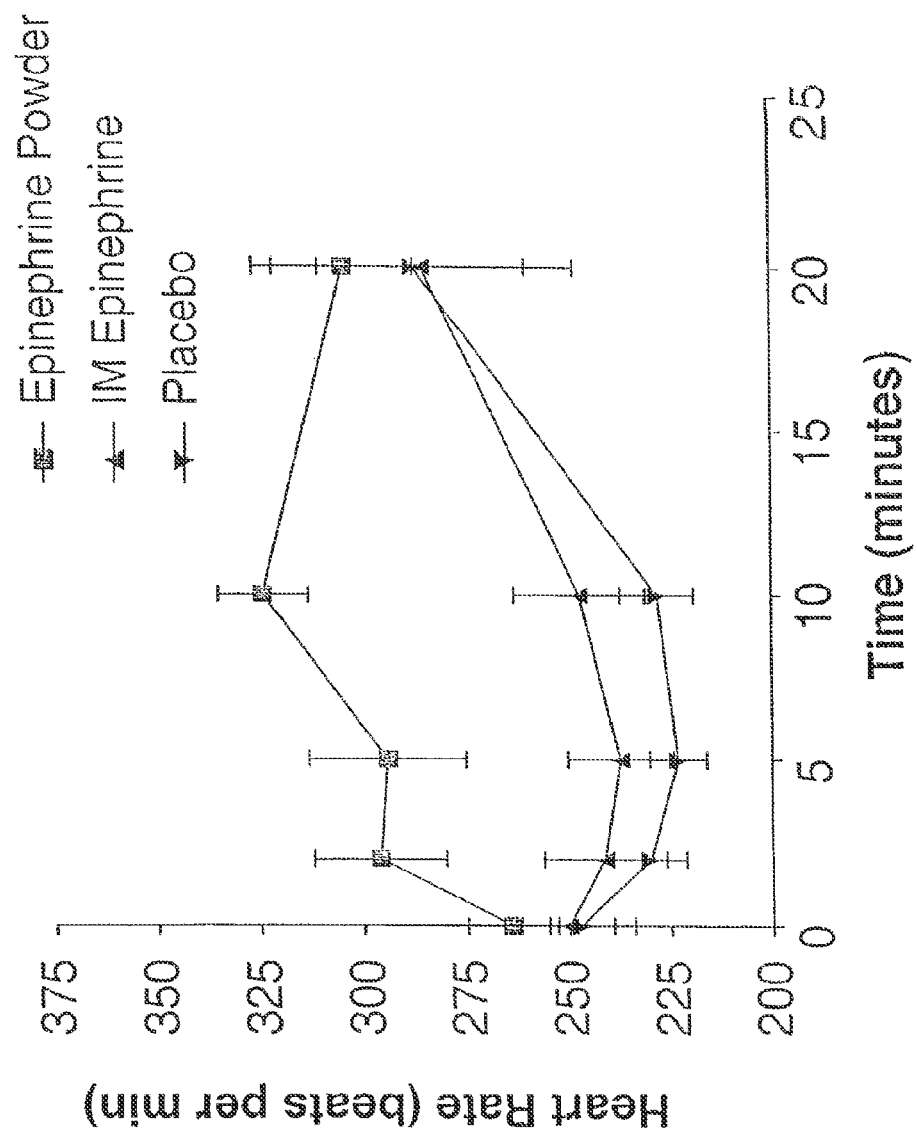
FIG. 6. Rat heart rate (beats per minute) following placebo treatment, pulmonary insufflation of dry powder epinephrine powder and intramuscular injection of epinephrine as a function of time in minutes.

Pharmacodynamics. FIG. 6 shows the change in heart rate following dosing with epinephrine. Heart rate increased rapidly in animals administered epinephrine by pulmonary insufflation. At ten minutes post-insufflation, heart rate reached a maximum of 324 beats per minute (+60 over baseline). Placebo and IM-injected animals did not exhibit a significant increase in heart rate compared to baseline. In fact, the heart rate was observed to decrease over the first 10 minutes. The anesthetic cocktail used during the insufflation contained xylazine, an alpha$_2$-adrenergic agonist. Therefore, the decrease in heart rate observed in the placebo and IM-injected animals may have been related to the anesthesia. Changes in heart rate may not have been observed at up to 20 minutes in animals given epinephrine by intramuscular injection because biologically effective levels of epinephrine had not yet been achieved. One animal intramuscularly injected with epinephrine was observed out to 40 minutes following dosing. Heart rate in this animal started to rise between 15 and 20 minutes post-dosing but did not significantly increase until 25 minutes following dosing (up to 340 beats/minute). This increase was still evident at 40 minutes following dosing. Therefore, the lack of a significant pharmacodynamic response in animals given IM epinephrine versus insufflated epinephrine was not surprising.

EXAMPLE 13

This example describes in vivo experiments conducted in rats to evaluate and compare three different dry powder epinephrine formulations (i.e., Formulations VII, IX and X). Powders were prepared using the procedures of Examples 3 and 7. The powders were delivered to the lungs by an insufflation technique. The insufflator device used for administration of powders to rat lungs was from PennCentury (Philadelphia, Pa.). The delivery tube of the insufflator was inserted intratracheally through the mouth until the tip of the tube was about a centimeter from the carina (first bifurcation). The amount of epinephrine weighed out to be delivered to the lungs was approximately 10 micrograms (i.e., 1.0 mg powder) irrespective of the animal's body weight. The volume of air used to deliver the powder from the sample chamber was 3 mL, which was achieved from a charged syringe. The syringe was recharged and discharged two more times for a total of three discharges per powder dose in order to decrease or eliminate powder residues in the sample chamber.

The jugular vein of animals used in pharmacokinetics studies was catheterized with PE90 on the day before the dosing and sampling was performed. A total of 18 animals were used in this study, 6 for each treatment group. For anesthesia (catheter placement and powder dosing), a anesthesia cocktail of ketamine (30 mg) and xylazine (4 mg) was injected intraperitoneally (IP) into each animal. The rats were placed on a heating pad after catheter placement to recover. After powder dosing, the rats were placed back in their respective cages.

Blood samples were collected by syringe from the jugular vein catheter. The blood was carefully ejected into EDTA coated tubes, mixed and then centrifuged for 1 minute at 14,000×g to separate the plasma from the cells. Plasma samples were placed into clean microfuge tubes and frozen with dry ice within two minutes of collection and kept frozen until received at the laboratory. Samples were stored at −20° C. until analysis.

Quantification of epinephrine was performed by using the RAT-CAT®-RIA (Catalog #017-RA616/100) from ALPCO Diagnostics. Briefly, adrenaline is extracted using a cis-diol-specific affinity gel and acylated to N-acyladrenaline and then converted enzymatically during the detection procedure into N-acylmetanephrine. The assay procedure follows the basic principle of radioimmunoassays, involving competition between a radioactive and a non-radioactive antigen for a fixed number of antibody binding sites. The amount of $^{125}$I-labelled antigen bound to the antibody is inversely proportional to the analyte concentration of the sample. When the reaction is in equilibrium, the antibody bound radioactivity is precipitated with a second antibody in the presence of polyethylene glycol. The precipitate is counted in a gamma counter. Quantification of unknown samples is achieved by comparing their activity with a reference curve prepared with known standards. Controls as supplied with the kit were run along with the samples.

Figure 7:
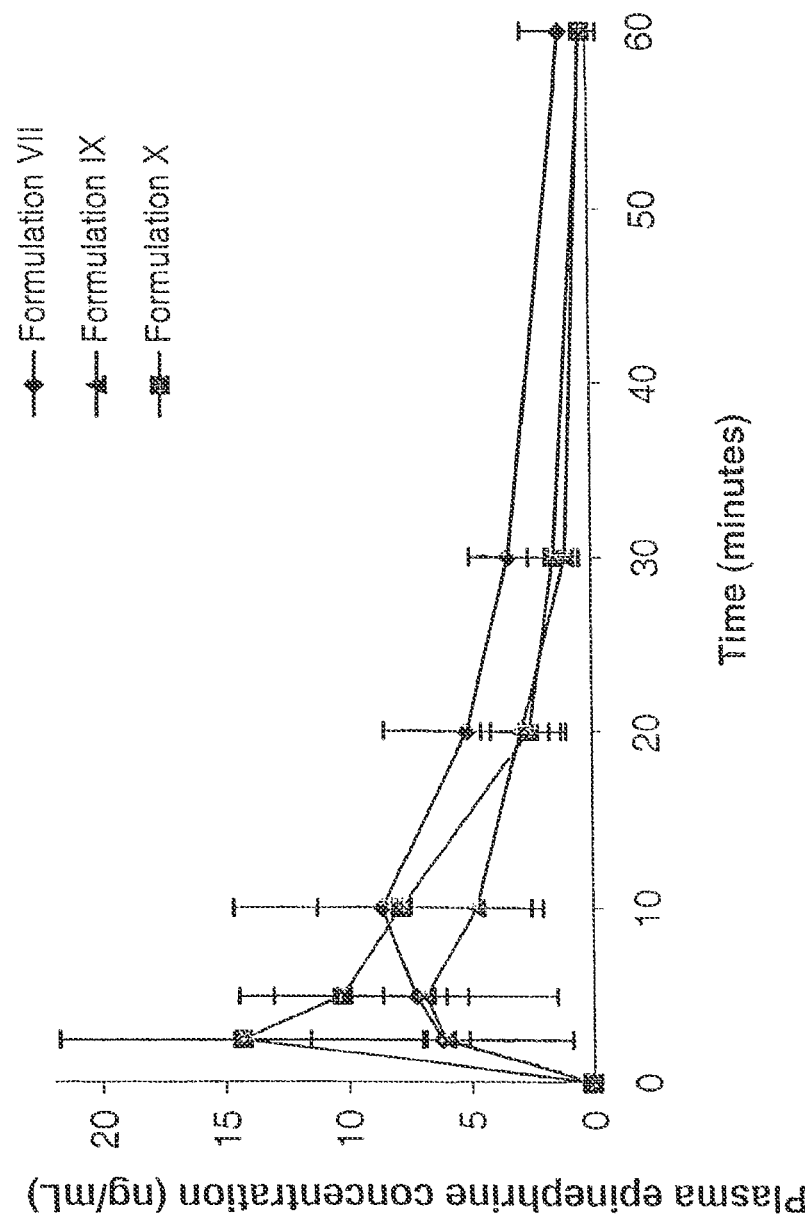
FIG. 7. Rat blood plasma epinephrine concentrations (ng/mL) as a function of time (in minutes) after intratracheal insufflation administration of dry powder epinephrine Formulations VII, IX, and X (Mean+SD).

Table K summarizes the results of the pharmacokinetics (PK) analysis including $C_{MAX}$, $T_{MAX}$, and $AUC_{LAST}$ (Area Under the Curve from baseline to the last measurable value). FIG. 7 shows the plasma epinephrine concentrations over time in graphical form. Plasma concentrations increased rapidly for all formulations and reached mean $C_{MAX}$ values of 7-14 ng/mL at a mean $T_{MAX}$ of 3-10 minutes.

TABLE K

Summary of PK analysis results (data presented as mean ± SD)

| Formulation | $C_{MAX}$ (ng/mL) | $T_{MAX}$ (minutes) | $AUC_{LAST}$ (ng min/mL) |
|---|---|---|---|
| VII (n = 6) | 9.9 ± 6.5 | 9.6 ± 6.0 | 222.5 ± 151.4 |
| IX (n = 6) | 7.1 ± 1.5 | 5.0 ± 2.7 | 128.4 ± 46.4 |
| X (n = 6) | 14.3 ± 7.4 | 3.3 ± 1.3 | 187.9 ± 90.7 |

EXAMPLE 14

The following example describes a pharmacokinetic (PK) study conducted in dogs to evaluate the PK and pharmacodynamic (PD) effects of dry powder epinephrine Formulation VII. Dry powders were prepared using the procedure of Example 3.

Six Beagle dogs were administered a nominal dose of 100 mg epinephrine dry powder epinephrine Formulation VII. For comparison, the same six dogs were administered 100 mg of epinephrine solution taken from a pediatric EPIPEN® and injected IM into the rear thigh through a 20 gauge needle using a 1 mL syringe. Blood samples were collected prior to dosing, immediately after dosing, and 2.5, 5, 10, 30, 45, 60 and 120 minutes after dosing. Epinephrine concentration in the drug plasma was analyzed by Covance Labs, Inc. (Vienna, Va.). In addition, each dog was implanted with a radiotelemetry device to continuously monitor cardiac function and changes in blood pressure.

Figure 8:
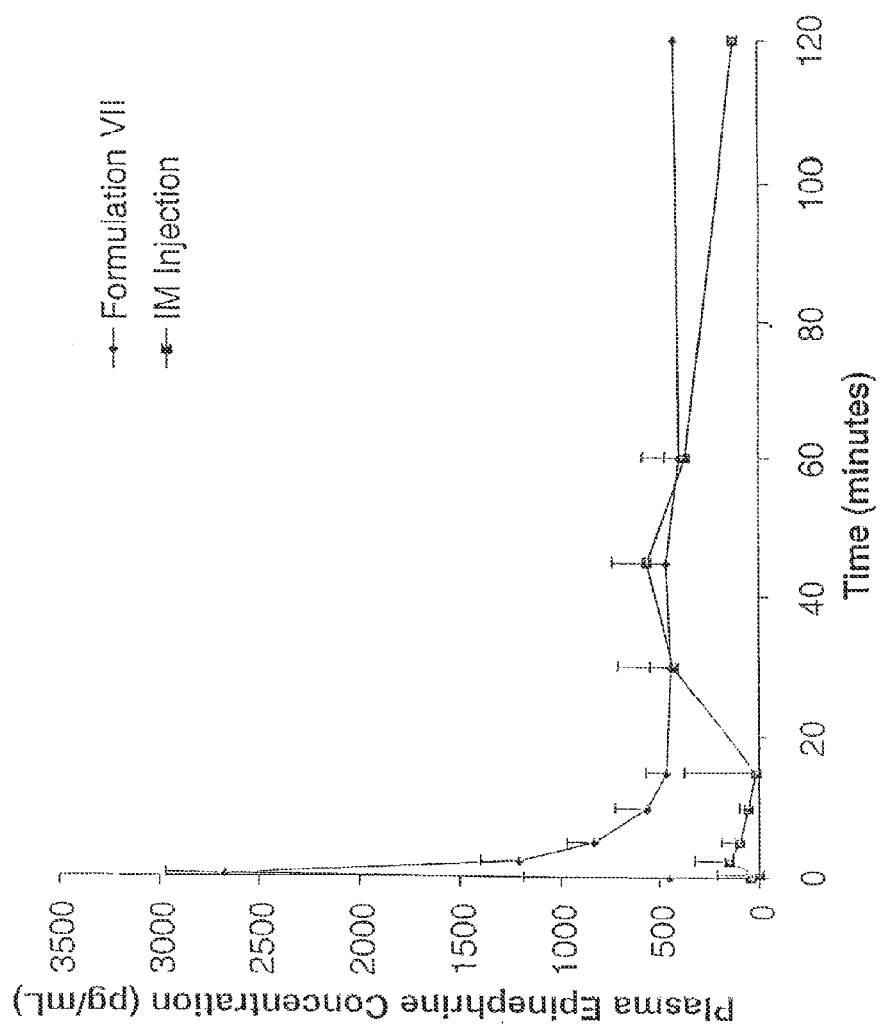
FIG. 8. Plasma epinephrine concentrations (pg/mL) versus time (in minutes) after inhalation of dry powder epinephrine Formulation VII or IM administration of epinephrine in Beagle dogs (Mean+SD).

Plasma concentrations of epinephrine increased rapidly following pulmonary delivery of dry powder-Epinephrine with a mean $C_{MAX}$ of 2,672 pg/mL. The $T_{MAX}$ and $C_{MAX}$ were observed immediately after inhalation (See Table L and FIG. 8). In contrast, mean $C_{MAX}$ after IM dosing was 647 pg/mL, with a longer mean $T_{MAX}$ of 38 minutes.

TABLE L $C_{MAX}$ and $T_{MAX}$ for Dry Powder Epinephrine and Injected Epinephrine in Beagle Dogs

| Test Article | Mean Dose(mg) | $C_{MAX}^1$ (pg/mL) | $T_{MAX}^1$ (min) |
|---|---|---|---|
| Formulation VII (n = 6) | 64[2] | 2672 (729) | IAD[3] |
| IM Injection of EPIPEN ® Contents(n = 6) | 100 | 647 (265) | 38 (8) |

[1]Data presented as mean (std dev)
[2]Inhaled doses of epinephrine were estimated based on pre-study validation of the dosing system which included determining the percent of the nominal dose deposited on a filter at the end of the endotracheal tube.
[3]IAD = Immediately After Dosing Dry powder epinephrine Formulation VII did not cause an increase in heart rate after dosing while heart rates were elevated (i.e., peak rate of 150 beats per minute) in two of the six dogs following IM administration of the pediatric EPIPEN® formulation. The absence of an increase in heart rate in most dogs was probably a consequence of the propofol anesthesia, administered to dogs for the inhalation procedure and prior to IM administration of epinephrine. Blood pressure (i.e., systolic, diastolic and mean arterial pressures) decreased following inhalation of dry powder epinephrine in all treated dogs. The IM administration of epinephrine caused a transient decline in blood pressure followed by variable slight increases in blood pressure. Differences observed in blood pressure responses between the inhaled and IM routes of administration were likely related to the amount of anesthesia the dogs received, with the dogs receiving more propofol for the inhalation procedure.

Spontaneously occurring ventricular premature beats (VPB) recorded prior to each dosing period were observed in two dogs. Both inhalation of dry powder epinephrine Formulation VII and IM epinephrine increased the incidence of VPB in these two animals during the 30-minute period after dosing; no ventricular arrhythmias were observed in any other dog.

EXAMPLE 15

The following example describes a clinical study evaluating inhaled dry powder porous particles containing epinephrine (Formulation VII, as described in Table A). The study was a Phase I, randomized, double blind, placebo-controlled, dose escalation study of the safety, tolerability and pharmacokinetics (PK) of single doses of dry powder epinephrine in healthy male subjects. Dry powder epinephrine (i.e, Formulation VII) was administered across a range of doses to evaluate the PK profile of inhaled dry powder epinephrine in comparison to injection (i.e., using either a standard IM injection using a vial and syringe or an EPIPEN® Autoinjector), and to identify potential dosing regimens of inhaled dry powder epinephrine for future development. Each subject (n=10) received single doses approximately one week apart of the following:

(a) Dry powder epinephrine (i.e., Formulation VII, prepared as in Example 2) at an epinephrine dose of 50 micrograms, 100 micrograms, 200 micrograms, and 400 micrograms;
(b) Placebo dry powder; and
(c) Epinephrine at a dose of 300 micrograms delivered via an autoinjector (EPIPEN®) and standard IM injection.

In addition, 8 of the 10 subjects received dry powder epinephrine (Formulation VII) at an epinephrine dose of 800 micrograms. Safety and PK information was obtained for at least 2 hours following dosing.

Initial evaluations indicated that the treatments were well tolerated, and dose escalation proceeded up to the maximum planned dose of 800 micrograms epinephrine in dry powder epinephrine form. There were no serious or severe adverse events. There were three moderate adverse events, which were regarded by the principle investigator as definitely not related to study treatment.

Figure 9:
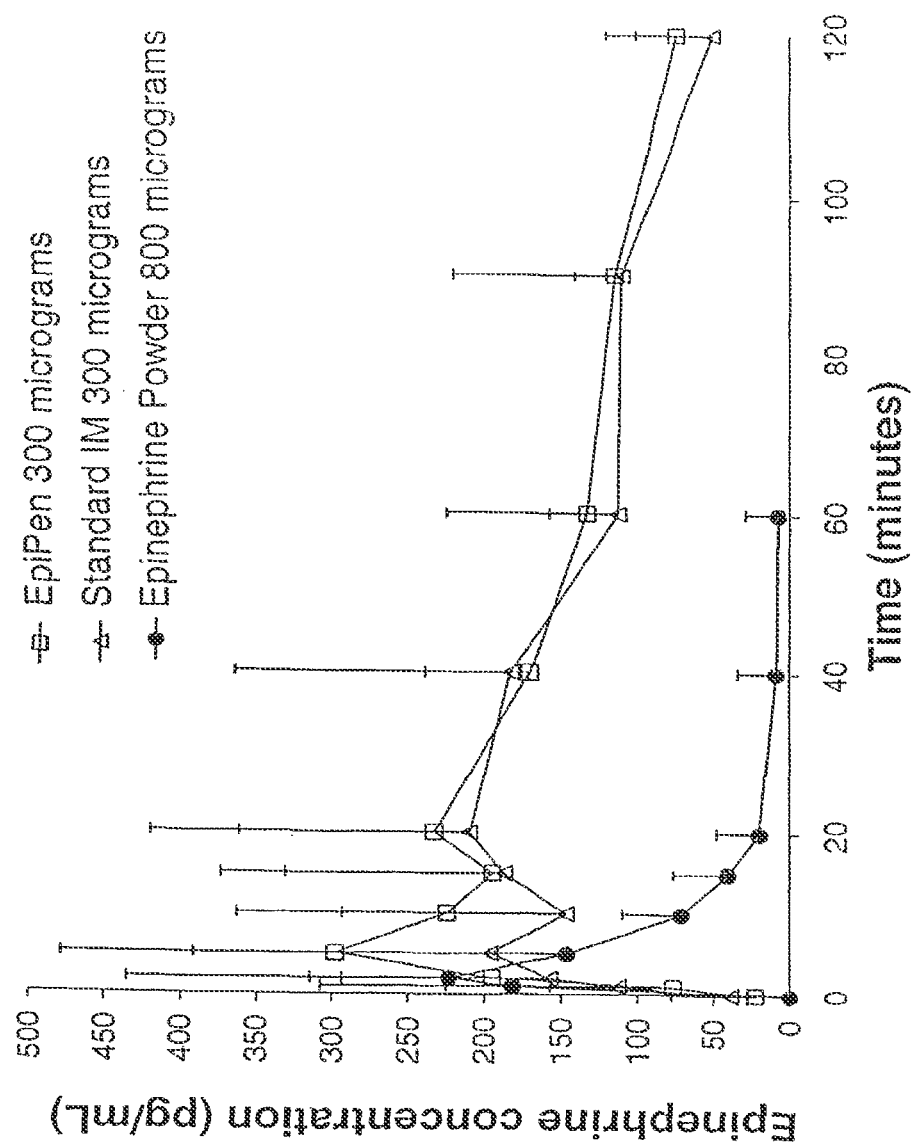
FIG. 9. Mean (SD) plasma epinephrine concentrations (pg/mL) versus time (in minutes) following dry powder epinephrine treatment or injection (i.e., standard IM and EPIPEN® Autoinjector) in humans at indicated doses.

The majority of plasma epinephrine concentrations following administration of dry powder epinephrine at doses of 50-400 micrograms, were near or below the lower limit of quantitation of the bioanalytical assay (50 pg/mL), which prevented estimation of PK parameters. More complete concentration-time profiles were observed following administration of dry powder epinephrine dosed at 800 micrograms and injections of 300 micrograms epinephrine. The mean plasma epinephrine concentration-time profiles from dry powder epinephrine dosed at 800 micrograms, EPIPEN® dose of 300 micrograms and standard IM injection dose of 300 micrograms are provided in FIG. 9.

EPIPEN® and standard IM injection provided greater systemic epinephrine exposure than dry powder epinephrine, however, there was significant variability in individual concentration profiles provided by EPIPEN® and standard IM injection. In the EPIPEN® treatment, there was evidence of two concentration peaks in many subjects, and one subject had very slow absorption. Slow absorption was also evident in several subjects in the standard IM treatment.

Figure 10:
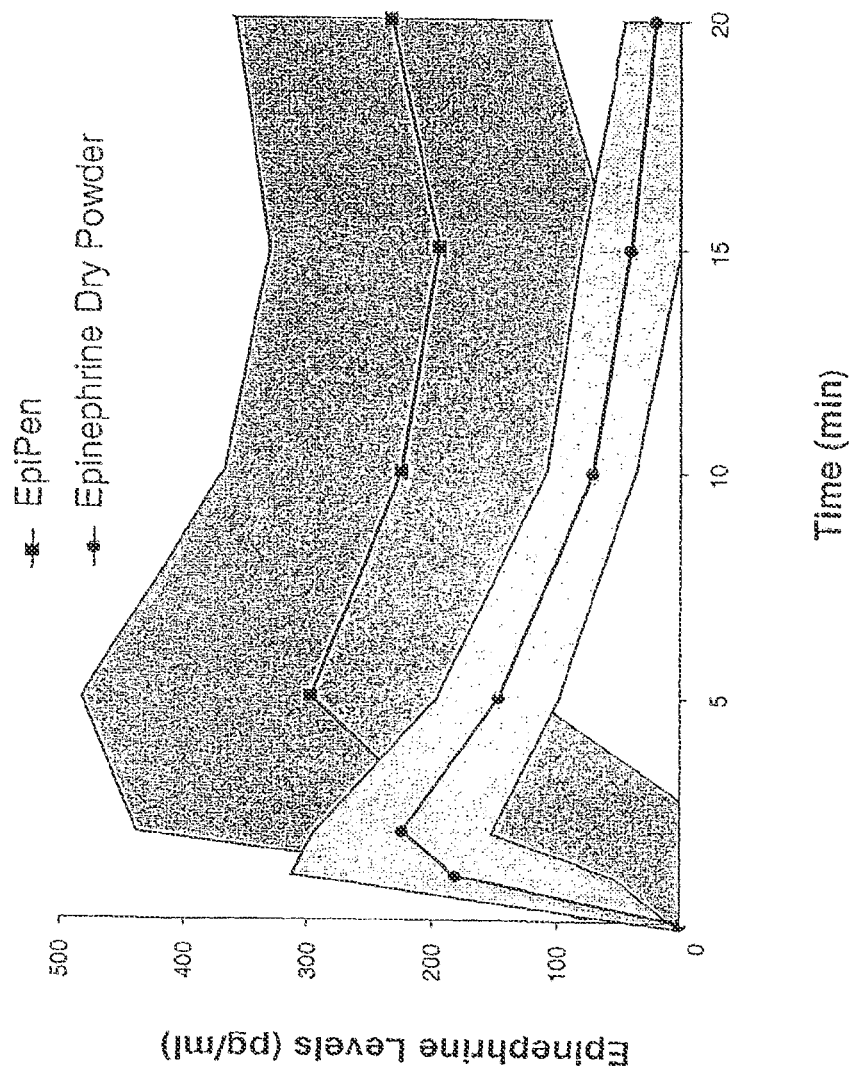
FIG. 10. Mean plasma epinephrine concentrations (pg/mL) as a function of time (in minutes) to 20 minutes post-dose following dry powder epinephrine or EPIPEN® autoinjection (shaded area represents ±SD).

Although the systemic exposure was lower following dry powder epinephrine, the PK profile over the first 20 minutes following dosing appears promising. FIG. 10 shows mean plasma epinephrine concentrations for 20 minutes post-dose for dry powder epinephrine and EPIPEN® treatments. For clarity, the standard IM treatment is not depicted on the graph, however, the variability observed was similar to that of the EPIPEN®.

With dry powder epinephrine treatment, epinephrine absorption was rapid and the inter-subject variability was lower compared to either injectable treatment. This suggests that higher doses of dry powder epinephrine may deliver a more reproducible dose than EPIPEN® or standard IM injection. Mean $C_{MAX}$ and $T_{MAX}$ estimates for dry powder epinephrine and injection treatments are provided in Table M.

TABLE M $C_{MAX}$ and $T_{MAX}$ Estimates

| Parameter | Treatment | | |
|---|---|---|---|
| | Dry powder Epinephrine (800 micrograms epinephrine) (n = 8) | EPIPEN ® 300 micrograms (n = 10) | Epinephrine 300 micrograms IM(n = 7)† |
| $C_{MAX}$(pg/mL) Mean (SD) % CV | 238 (76)32 | 397 (196)49 | 263 (174)66 |
| $T_{MAX}$(min) Median (range) | 2 (1-5) | 12.5 (2-90) | 15 (1-60) |

†Sufficient concentration data available from only 7 of 10 subjects
SD: standard deviation
% CV: % coefficient of variation Following administration of dry powder epinephrine, epinephrine was rapidly absorbed, with a median $T_{MAX}$ of 2 minutes. The largest $T_{MAX}$ value (5 minutes) was reported in one subject; the remaining 7 subjects reported $T_{MAX}$ values less than or equal to 2 minutes. In contrast, administration of epinephrine via EPIPEN® resulted in a median $T_{MAX}$ of 12.5 minutes, over six times the value observed with dry powder epinephrine. Half of the subjects had $T_{MAX}$ values equal to or greater than 20 minutes. In addition to being longer compared to dry powder epinephrine, $T_{MAX}$ values were more variable following EPIPEN® administration and ranged from 2 to 90 minutes. The $T_{MAX}$ following standard IM injection was similar to that observed following EPIPEN® administration. $T_{MAX}$ was longer (i.e., median $T_{MAX}$ of 15 minutes) and more variable (i.e., a range of 1-60 minutes) than for dry powder epinephrine treatment.

The mean $C_{MAX}$ following dry powder epinephrine dosed at 800 micrograms was comparable to that observed following standard 300 microgram IM injection (238 pg/mL versus 263 pg/mL), however, the variability was lower (32% CV versus 66% CV). The mean in the standard IM treatment was likely influenced by 2 subjects, who reported higher $C_{MAX}$ values relative to the others in the group (405 and 595 pg/mL compared to 220 pg/mL or less). The mean $C_{MAX}$ following dry powder epinephrine dosed at 800 micrograms was lower than that observed for the 300 microgram EPIPEN® (238 pg/mL versus 397 pg/mL). Again, reduced variability was observed compared to EPIPEN® (32% CV versus 49% CV).

Figure 11:
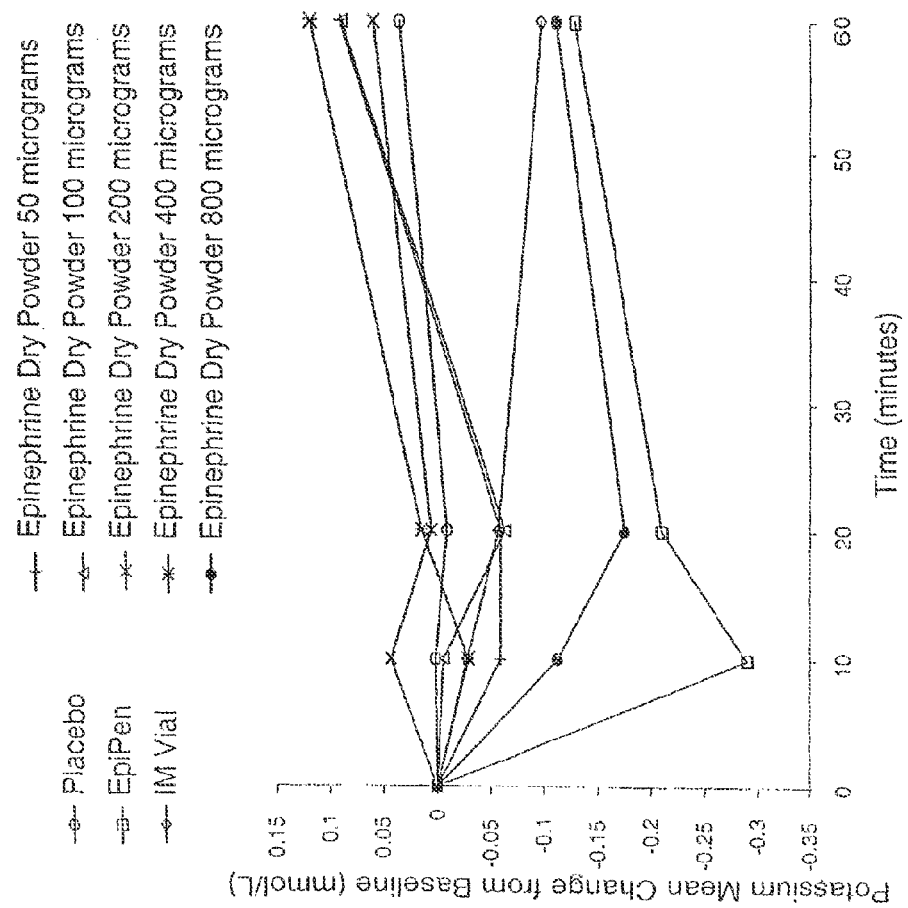
FIG. 11. Potassium mean change from baseline (mmol/L) versus time (in minutes) following dry powder epinephrine administered at indicated doses or epinephrine injection (standard IM and EPIPEN® at 300 microgram doses).

In a preliminary pharmacodynamic (PD) analysis, plots of parameter changes over time were produced. The shapes of the curves for the different epinephrine routes of administration suggest the relationship between epinephrine concentration and effect is not direct for all PD markers. For example, shown in FIG. 11 are the potassium mean changes from baseline for the dry powder epinephrine and IM injections. These data indicate EPIPEN® produced the maximal mean change from baseline at 10 minutes after dosing, similar to the time epinephrine $C_{MAX}$ occurred (i.e., median $T_{MAX}$ was 12.5 minutes). In contrast, the maximum potassium mean change from baseline for dry powder epinephrine dosed at 800 micrograms occurred later than EPIPEN® (i.e., 20 minutes post-dose), despite having reached the maximum plasma epinephrine concentration more rapidly after dosing (i.e., median $T_{MAX}$ was 2 minutes). Potassium concentrations after standard IM treatment continued to decrease through 60 minutes post-dose, even though maximum plasma concentration was reached approximately 15 minutes post-dose.

Because some pharmacological responses to epinephrine take time to develop, the observed response at any given time is not apparently related to the plasma concentration at that same time. Marked differences in epinephrine concentration-time profiles between inhaled and injected epinephrine do not directly translate into marked differences in the effect-time profiles. Therefore, despite different PK profiles, it may be possible to achieve a PD profile with dry powder epinephrine similar to that of epinephrine injection.

In summary, the results from this human study indicate that dry powder epinephrine is a promising alternative method of delivery for epinephrine. No serious safety issues resulted following the administration of single doses. Epinephrine $T_{MAX}$ was noticeably shorter following dry powder epinephrine administration compared to injection (i.e., both EPIPEN® and standard IM injection). In addition, variability in $C_{MAX}$ and $T_{MAX}$ was reduced with dry powder epinephrine relative to injection. That is, the coefficient of variation (CV) of plasma $T_{MAX}$ and $C_{MAX}$ were substantially lower with dry powder epinephrine than with injected epinephrine.

EXAMPLE 16

The following example describes a proposed human study of dry powder Formulation IX as described in Table A. The aims of this study include: 1) assessment of the safety and tolerability of dry powder epinephrine Formulation IX, 2) evaluation of the pharmacokinetic (PK) and pharmacodynamic (PD) profiles across a range of doses, and 3) identification of potential dosing regimens of inhaled dry powder epinephrine for subsequent clinical development. The initial dry powder epinephrine dose is anticipated to have borderline PD effect (i.e., less than EPIPEN®, 300 micrograms). Subsequent dry powder epinephrine dose escalation will be performed to determine a dose of inhaled epinephrine that achieves PD effects of a similar magnitude as those observed with EPIPEN®.

The design will be a eight period, single cohort, double blind, placebo and active comparator controlled, dose escalation study in ~24 healthy male and female volunteers. Subjects will be screened to exclude cardiovascular abnormalities. Screening will require a normal treadmill exercise test and Holter monitor recording.

Subjects will be administered EPIPEN® (300 micrograms) and a 300 microgram subcutaneous injection in Groups 1 and 2, respectively.

In Groups 3, 4, and 5, subjects will be administered placebo and a dose of 500 micrograms and 1000 micrograms epinephrine in dry powder Formulation IX in a double blind fashion. Subjects will be randomized to one of three treatment sequences (N=8: placebo, 500 micrograms epinephrine, 1000 micrograms epinephrine; N=8: 500 micrograms, placebo, 1000 micrograms epinephrine; N=8: 500 micrograms epinephrine, 1000 micrograms epinephrine, placebo). The starting dry powder epinephrine dose was selected on the basis of the results of human studies described in Example 15. The initial 500 micrograms dose to be used as a starting dose is below the highest dose used in dry powder epinephrine (800 micrograms epinephrine) which was administered to humans and was well tolerated and demonstrated a lower level of epinephrine exposure/PD response as compared to EPIPEN® (300 micrograms). Dose escalation should allow elucidation of a dose of dry powder epinephrine that is both well tolerated and provides the desired PD response.

In Groups 6, 7, and 8 subjects will be administered 1500, 2000, and 2500 micrograms epinephrine in dry powder epinephrine, respectively. Following each administration of study drug, repeat ECG, rhythm strip, serum chemistry, hematology, urinalysis, physical exam findings, and spirometry will be obtained. Repeat plasma samples will be collected for PK analysis. Spontaneously reported adverse events will be recorded.

To assess the impact of asthma on the systemic delivery of epinephrine, a PK evaluation of dry powder epinephrine will be performed in patients with mild to moderate asthma. Two studies in asthma patients are planned, including: 1) a pilot investigation; and 2) a definitive clinical study using dry powder epinephrine and a clinical dose regimen, including use of a commercial inhaler.

Several PD parameters exist to gauge the magnitude and duration of beta agonist activities elicited by epinephrine. As shown in Table N, several of these parameters, including systolic blood pressure, correspond directly to therapeutic actions of epinephrine in the treatment of anaphylaxis. PD measurements will be included in all PK studies. As detailed in the section below, comparison of the PD profile of dry powder epinephrine versus IM epinephrine will be the primary basis for dose selection.

TABLE N

Pharmacodynamic Parameters

| Pharmacodynamic Parameters | Key Physiologic Actions of Epinephrine in the Treatment of Anaphylaxis |
|---|---|
| Systolic Blood Pressure ($\beta1 > \beta2$) | Cardiac Output($\beta1 > \beta2$) |
| Diastolic Blood Pressure($\alpha1, \beta 2$) | Increase Systemic Vascular Resistance($\alpha1, \beta2$) |
| Heart Rate($\beta1 > \beta2$) | Decrease Vascular Leakage and Tissue Edema($\beta2$) |
| QTc($\beta1 > \beta2$) | Decrease Bronchospasm($\beta2$) |
| Serum K + ($\beta2$) | Inhibit Mast Cell Degranulation*($\beta2$) |
| Serum Glucose($\beta2, \alpha2, \beta3$) | FEV1($\beta2$) |

Adapted from Goodman and Gilman's, *The Pharmacologic Basis for Therapeutics*, 10th ed. 2001, McGraw Hill, New York, Chapter 10, p 215.
*Recent in vitro studies indicate that beta agonists inhibit mast cell degranulation. Treatment with epinephrine may interfere with the inflammatory cascade by blocking the release of mast cell mediators, although the clinical relevance of these in vitro findings is uncertain. Barnes, P. J., "Effect of Beta-Agonists on Inflammatory Cells," *J. Allergy Clin. Immunol.* 104(2 Pt 2): s10-7 (1999).

Forced expiratory volume in one second ($FEV_1$) measurements will be included in studies in normal volunteers and studies in patients with asthma. The effects of dry powder epinephrine and injected epinephrine on $FEV_1$ and other spirometric parameters will be compared.

Because it is unethical and impractical to perform efficacy studies in a setting of clinical anaphylaxis, dose selection for dry powder epinephrine will utilize a PK/PD modeling approach. The goal is to identify a dose/dosing regimen of dry powder epinephrine that yields a PD profile that compares favorably to that observed following 300 micrograms of injected epinephrine.

Mathematical models (e.g., based on PD or PK/PD dose-response relationship) will be implemented in clinical trial simulation exercises and used to estimate a dose/dosing regimen of dry powder epinephrine that is expected to yield similar magnitude of effects on PD markers as administration of 300 micrograms injected epinephrine.

The dose/dosing regimen identified by PK modeling will be evaluated and compared to injected epinephrine (300 micrograms) in a clinical study. A primary objective of this study will be to confirm that the selected dry powder epinephrine dose regimen yields a PD profile similar in magnitude to that observed with injected epinephrine using criteria defined by PK/PD modeling. Assuming that the desired PK/PD profile is observed, the selected dose/dosing regimen will be propagated throughout subsequent clinical studies.

A safety assessment of dry powder epinephrine will consist of evaluations in normal volunteers, asthma, and anaphylaxis patients. All studies with dry powder epinephrine will include comprehensive evaluations of safety including adverse events, repeat vital signs, physical exams, ECG evaluations (including specific evaluations of QT interval and cardiac rhythm), serum chemistry (including glucose and potassium), and hematology. Across the clinical development program, approximately 150 subjects/patients will receive at least one administration of dry powder epinephrine. The vast majority of these patients will also receive an administration of an injected comparator.

Both the safety and efficacy of epinephrine are mechanism-based relating to alpha and beta adrenergic agonism. As noted above, PK/PD modeling will be performed with a variety of parameters including systolic and diastolic blood pressure, serum potassium, pulmonary function, and heart rate. The intent of this analysis is to define a dose/dosing regimen of dry powder epinephrine that results in systemic adrenergic agonism to a similar magnitude to that which occurs following 300 micrograms injected epinephrine. Using this approach, the safety profile of the final dry powder epinephrine dosing regimen should be similar to injected administration of epinephrine.

EXAMPLE 17

The following example describes a human clinical study evaluating inhaled dry powder porous particles containing epinephrine (i.e., Formulation XI: 72% Leucine, 16% Epinephrine bitartrate, and 12% Sodium tartrate (%'s by weight), as described in Table A). The study was part of a Phase I, single cohort, blinded, placebo and active controlled, dose escalation study in 23 healthy male and female volunteer subjects.

Each subject (n=23) received single doses at least two days apart of the following:
 (a) placebo dry powder;
 (b) epinephrine at a dose of 300 micrograms delivered via an autoinjector (EPIPEN®); and
 (c) epinephrine at a dose of 300 micrograms delivered via standard subcutaneous (SC) injection.

Twelve subjects (i.e., n=12) received 2 doses of dry powder epinephrine (i.e., Formulation XI, prepared using the same method described in Example 8) each at a dose of 500 micrograms, separated by a 15 minute interval. Dry powder epinephrine was administered to each of the subjects at least two days after the administration of a placebo or injected epinephrine as described above. The dry powder epinephrine particles had a VMGD of 6.3 microns at 1 bar as determined by RODOS and a FPF(<3.3) of 31% measured using ACI-3 with wet screens.

Pharmacodynamic parameters, including systolic blood pressure and serum potassium levels, corresponding to therapeutic actions of epinephrine in the treatment of anaphylaxis were used as indicators of dry powder epinephrine effectiveness, e.g., to gauge the magnitude and duration of beta agonist activities elicited by epinephrine.

Epinephrine was rapidly absorbed from the dry powder epinephrine formulation, with maximal plasma concentrations occurring at about 1 minute following inhalation. In general, dose-related changes in PD variables with rapid onset were observed following administration of the dry powder epinephrine formulation. Adverse events consistent with alpha and beta-adrenergic agonism (e.g., palpitations, tremor and pallor) appeared to be dose related. The majority of adverse events reflected mechanism-based effects due to alpha and beta-adrenergic stimulation.

Figure 12:
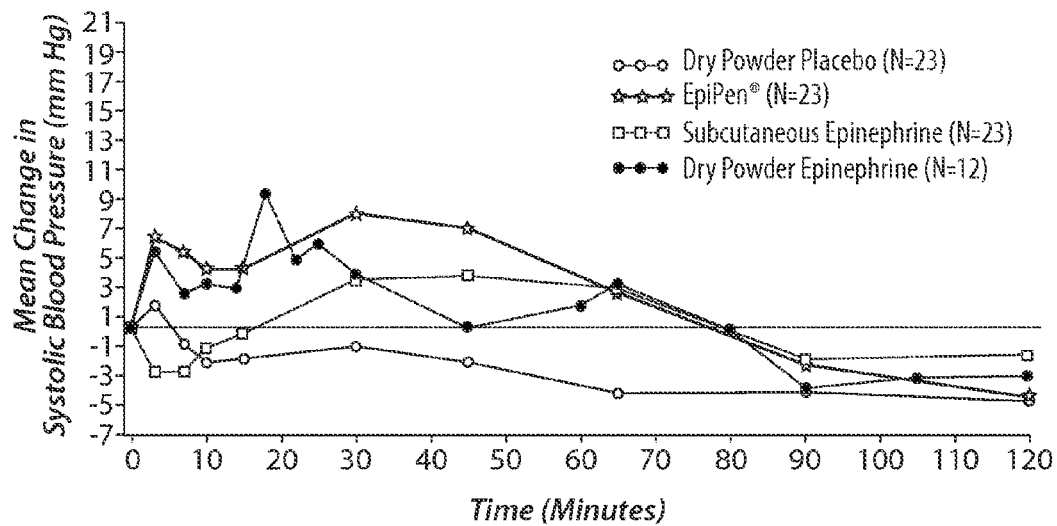
FIG. 12. Mean change in human systolic blood pressure (mm Hg) versus time (in minutes) following (1) administration of an initial dose of dry powder epinephrine (500 micrograms epinephrine) with a subsequent dose of dry powder epinephrine (500 micrograms epinephrine) at 15 minutes (n=12), (2) administration of dry powder placebo (n=23), (3) a 300 microgram subcutaneous injection of epinephrine (n=23), and (4) administration of EPIPEN® at a 300 microgram dose (n=23).
Figure 13:
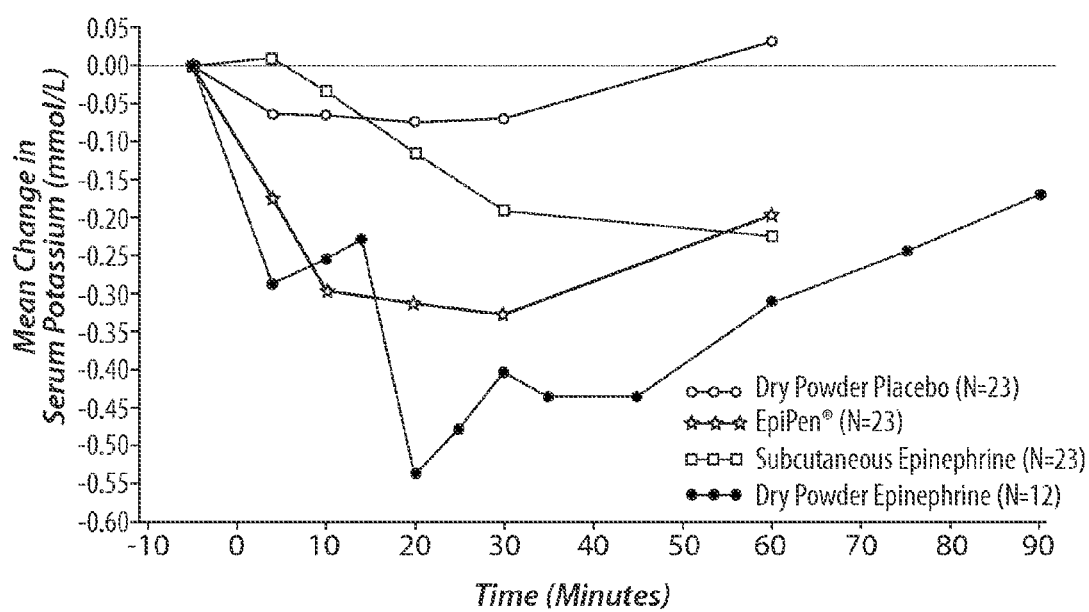
FIG. 13. Mean change in human blood serum potassium concentration (in mmol/L) versus time (in minutes) following (1) administration of an initial dose of dry powder epinephrine (500 micrograms epinephrine) with a subsequent dose of dry powder epinephrine (500 micrograms epinephrine) at 15 minutes (n=12), (2) administration of dry powder placebo (n=23), (3) a 300 microgram subcutaneous injection of epinephrine (n=23), and (4) administration of EPIPEN® at a 300 microgram dose (n=23).
Figure 14:
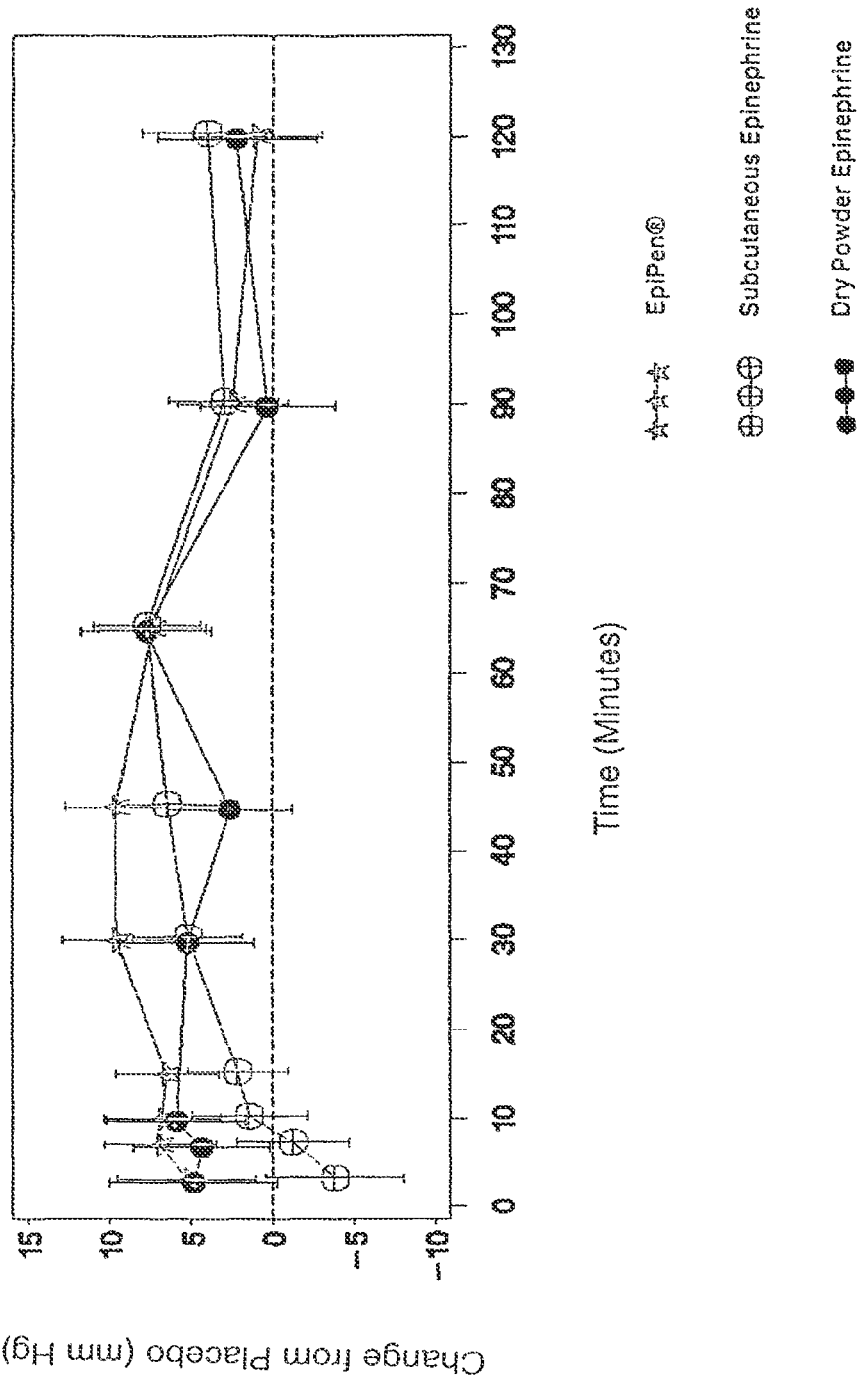
FIG. 14. Change from placebo and 95% confidence interval of human systolic blood pressure (in mm Hg) versus time (in minutes) following (1) administration of an initial dose of dry powder epinephrine (500 micrograms epinephrine) with a subsequent dose of dry powder epinephrine (500 micrograms epinephrine) at 15 minutes, (2) a 300 microgram subcutaneous injection of epinephrine, and (3) administration of EPIPEN® at a 300 microgram dose.
Figure 15:
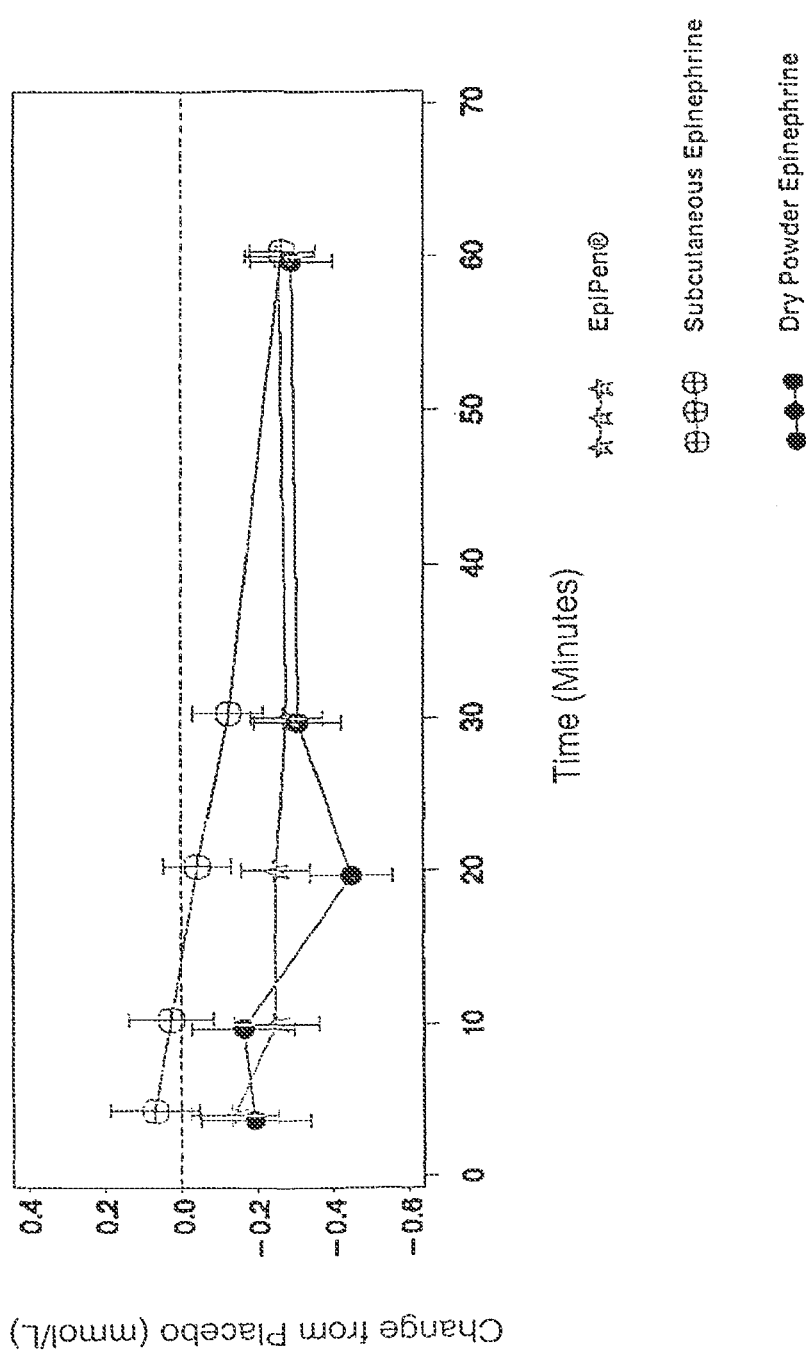
FIG. 15. Change from placebo and 95% confidence interval of human blood serum potassium concentration (in mmol/L) versus time (in minutes) following (1) administration of an initial dose of dry powder epinephrine (500 micrograms epinephrine) with a subsequent dose of dry powder epinephrine (500 micrograms epinephrine) at 15 minutes, (2) a 300 microgram subcutaneous injection of epinephrine, and (3) administration of EPIPEN® at a 300 microgram dose.

FIGS. 12 and 13 show mean changes in human systolic blood pressure (in mm Hg) and blood serum potassium concentrations (in mmol/L), respectively, versus time (in minutes) following (1) administration of an initial dose of dry powder epinephrine (500 micrograms epinephrine) with administration of a subsequent dose of dry powder epinephrine (500 micrograms epinephrine) at 15 minutes (n=12), (2) administration of dry powder placebo (n=23), (3) a 300 microgram subcutaneous injection of epinephrine (n=23), and (4) administration of EPIPEN® at a 300 microgram dose (n=23). FIGS. 14 and 15 show the change from placebo and 95% confidence interval of human systolic blood pressure (in mm Hg) and blood serum potassium concentrations (in mmol/L), respectively, versus time (in minutes) following (1) administration of an initial dose of dry powder epinephrine (500 micrograms epinephrine) with administration of a subsequent dose of dry powder epinephrine (500 micrograms epinephrine) at 15 minutes, (2) a 300 microgram subcutaneous injection of epinephrine, and (3) administration of EPIPEN® at a 300 microgram dose.

FIGS. 12 through 15 demonstrate that administration of a second dose of dry powder epinephrine (500 micrograms epinephrine) 15 minutes after an initial administration of a 500 microgram epinephrine dose via dry powder resulted in systolic blood pressure and serum potassium concentration changes that approximated or exceeded the duration and magnitude of changes observed with injectable epinephrine administration.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating a patient in need of epinephrine, the method comprising:
   administering an effective amount of substantially dry particles to the respiratory system of the patient, the particles comprising:
   (a) epinephrine, or a salt thereof wherein the epinephrine, or salt thereof, contained in the particles is amorphous; and
   (b) at least one pharmaceutically acceptable excipient.

2. The method of claim 1, wherein the epinephrine, or salt thereof, is present in the particles in an amount ranging from about 1 to about 95 weight percent.

3. The method of claim 2, wherein the epinephrine, or salt thereof, is present in the particles in an amount ranging from about 1 to about 45 weight percent.

4. The method of claim 3, wherein the epinephrine, or salt thereof, is present in the particles in an amount ranging from about 1 to about 30 weight percent.

5. The method of claim 1, wherein the particles are aerodynamically light.

6. The method of claim 1, wherein the particles are spray dried.

7. The method of claim 1, wherein the particles are amorphous.

8. The method of claim 1, wherein the pharmaceutically acceptable excipient contained in the particles is amorphous.

9. The method of claim 1, wherein the pharmaceutically acceptable excipient contained in the particles is crystalline.

10. The method of claim 1, wherein the particles are administered via inhalation.

11. The method of claim 10, wherein the particles comprise at least about 50 micrograms of epinephrine and are administered in a single inhalation.

12. The method of claim 11, wherein the particles comprise about 250 micrograms to about 5 milligrams of epinephrine and are administered in a single inhalation.

13. The method of claim 1, wherein the particles are administered to the respiratory system via a breath activated inhaler.

14. The method of claim 13, wherein the particles are administered to the respiratory system in a single breath activated step.

15. The method of claim 1, wherein a first portion of the particles is deposited in the airways of the respiratory system and a second portion of the particles is deposited to the alveoli region of the lungs.

16. The method of claim 1, wherein administering an effective amount of particles includes delivering a portion of the particles to the alveoli region of the lungs.

17. The method of claim 1, wherein administering an effective amount of particles includes delivering a portion of the particles to the upper airways.

18. The method of claim 1, wherein the epinephrine is released from the particles and acts systemically.

19. A method for treating a patient in need of epinephrine, the method comprising:
   administering an effective amount of substantially dry particles to the respiratory system of the patient, the particles comprising:
   (a) epinephrine, or a salt thereof wherein the epinephrine, or salt thereof is crystalline; and
   (b) at least one pharmaceutically acceptable excipient.

20. A method for treating a patient in need of epinephrine, the method comprising:
   administering an effective amount of substantially dry particles to the respiratory system of the patient, the particles comprising:
   (a) epinephrine, or a salt thereof; and
   (b) at least one pharmaceutically acceptable excipient wherein the excipient is amorphous.

21. A method for treating a patient in need of epinephrine, the method comprising:
   administering an effective amount of substantially dry particles to the respiratory system of the patient, the particles comprising:
   (a) epinephrine, or a salt thereof; and
   (b) at least one pharmaceutically acceptable excipient wherein the excipient is crystalline.

22. A method for treating a patient in need of epinephrine, the method comprising:
   administering an effective amount of substantially dry particles to the respiratory system of the patient, the particles comprising:
   (a) epinephrine, or a salt thereof; and
   (b) at least one pharmaceutically acceptable excipient wherein the epinephrine is released from the particles in a sustained manner.

23. A method for treating a patient in need of epinephrine, the method comprising:
   administering an effective amount of substantially dry particles to the respiratory system of the patient, the particles comprising:
   (a) epinephrine, or a salt thereof; and
   (b) at least one pharmaceutically acceptable excipient wherein the particles are amorphous.

24. A method for treating a patient in need of epinephrine, the method comprising:
   administering an effective amount of substantially dry particles to the respiratory system of the patient, the particles comprising:
   (a) epinephrine, or a salt thereof;
   (b) at least one pharmaceutically acceptable excipient; and
   (c) leucine in an amount of from about 62 to about 82 weight percent.

* * * * *